US009540675B2

(12) United States Patent
De Forest et al.

(10) Patent No.: US 9,540,675 B2
(45) Date of Patent: Jan. 10, 2017

(54) REAGENT CARTRIDGE AND METHODS FOR DETECTION OF CELLS

(71) Applicant: GeneWeave Biosciences, Inc., Los Gatos, CA (US)

(72) Inventors: Nikol De Forest, Scotts Valley, CA (US); Werner Frei, Los Gatos, CA (US); Diego Rey, Palo Alto, CA (US); Shaunak Roy, Sunnyvale, CA (US); Soni Shukla, Santa Clara, CA (US); Ryan C. Griswold, Los Gatos, CA (US); Kenneth G. Olson, San Jose, CA (US); Bruce J. Richardson, Los Gatos, CA (US); Victor H. Yee, Castro Valley, CA (US)

(73) Assignee: GeneWeave Biosciences, Inc., Los Gatos, CA (US)

( * ) Notice: Subject to any disclaimer, the term of this patent is extended or adjusted under 35 U.S.C. 154(b) by 0 days.

(21) Appl. No.: 14/617,631

(22) Filed: Feb. 9, 2015

(65) Prior Publication Data
US 2015/0218613 A1 Aug. 6, 2015

Related U.S. Application Data

(63) Continuation-in-part of application No. 14/476,392, filed on Sep. 3, 2014, now abandoned.

(60) Provisional application No. 61/983,765, filed on Apr. 24, 2014, provisional application No. 61/939,126, filed on Feb. 12, 2014, provisional application No. 61/897,040, filed on Oct. 29, 2013.

(51) Int. Cl.
*B01L 3/00* (2006.01)
*C12Q 1/04* (2006.01)
*C12Q 1/68* (2006.01)

(52) U.S. Cl.
CPC .............. *C12Q 1/04* (2013.01); *B01L 3/502* (2013.01); *B01L 3/50825* (2013.01); *B01L 2200/16* (2013.01); *B01L 2300/042* (2013.01); *B01L 2300/044* (2013.01); *B01L 2300/047* (2013.01); *B01L 2300/049* (2013.01); *B01L 2300/0672* (2013.01); *B01L 2300/0867* (2013.01); *B01L 2400/0478* (2013.01); *B01L 2400/0683* (2013.01)

(58) Field of Classification Search
CPC ............ B01L 2200/16; B01L 2300/042; B01L 2300/044; B01L 2300/047; B01L 2300/049; B01L 2300/0672; B01L 2300/0867; B01L 2400/0478; B01L 2400/0683; B01L 3/502; B01L 3/50825; C12Q 1/04
USPC .................................. 435/287.1, 5
See application file for complete search history.

(56) References Cited

U.S. PATENT DOCUMENTS

| 3,122,420 A | 2/1964 | Rebar et al. |
| 3,826,574 A | 7/1974 | Brown, Jr. |
| 4,057,148 A | 11/1977 | Meyer et al. |
| 4,730,933 A | 3/1988 | Lohr |
| 4,861,709 A | 8/1989 | Ulitzur et al. |
| 5,086,233 A | 2/1992 | Stafford et al. |
| 5,139,745 A | 8/1992 | Barr et al. |
| 5,188,455 A | 2/1993 | Hammerstedt |
| 5,221,623 A | 6/1993 | Legocki et al. |
| 5,242,660 A | 9/1993 | Hsei |
| 5,364,591 A | 11/1994 | Green et al. |
| 5,447,687 A | 9/1995 | Lewis et al. |
| 5,447,836 A | 9/1995 | Wolber et al. |
| 5,494,646 A | 2/1996 | Seymour |
| 5,498,525 A | 3/1996 | Rees et al. |
| 5,582,969 A | 12/1996 | Pearson et al. |
| 5,645,801 A | 7/1997 | Bouma et al. |
| 5,656,424 A | 8/1997 | Jurgensen et al. |
| 5,677,124 A | 10/1997 | DuBois et al. |
| 5,730,938 A | 3/1998 | Carbonari et al. |
| 5,814,022 A | 9/1998 | Antanavich et al. |
| 5,824,468 A | 10/1998 | Scherer et al. |
| 5,858,693 A | 1/1999 | Cottingham |
| 5,912,119 A | 6/1999 | Radman et al. |

(Continued)

FOREIGN PATENT DOCUMENTS

| CA | 1094477 | * 1/1981 |
| DE | 1994/4423935 | 1/1996 |

(Continued)

OTHER PUBLICATIONS

International Search Report and Written Opinion for International Application No. PCT/US2014/023422, mailed Sep. 8, 2014, 23 pages.
Office Action for U.S. Appl. No. 14/611,902, mailed Mar. 30, 2015, 12 pages.
Dual-Glo Luciferase Assay System, Instructions for Use of Products E2920, E2940 and E2980, Technical Manual, Promega, 2011, 27 pages.
Hakamata, T. et al. (eds.), Chapter 14—Applications in Photomultiplier Tubes, Basics and Applications, Third Edition (Edition 3a), Hamamatsu Photonics K. K., 2007, 48 pages.

(Continued)

*Primary Examiner* — Janet Epps-Smith

(57) ABSTRACT

An apparatus includes a housing and an actuator. The housing, which defines a reagent volume that can receive a reagent container, can be removably coupled to a reaction chamber. The housing includes a puncturer that defines a transfer pathway in fluid communication with the reagent volume. A delivery portion of the housing defines a delivery pathway between the transfer pathway and the reaction chamber when the housing is coupled to the reaction chamber. The actuator has a plunger portion disposed within the reagent volume. An engagement portion of the actuator can be manipulated to move the plunger portion within the reagent volume to deform the reagent container. The puncturer can pierce a frangible portion of the reagent container to convey a reagent from the reagent container into the reaction chamber via the transfer pathway and/or the delivery pathway.

36 Claims, 29 Drawing Sheets

(56) References Cited

U.S. PATENT DOCUMENTS

| | | |
|---|---|---|
| 5,917,592 A | 6/1999 | Skiffington |
| 5,919,625 A | 7/1999 | DuBois et al. |
| 5,939,262 A | 8/1999 | Pasloske et al. |
| 5,965,415 A | 10/1999 | Radman et al. |
| 5,989,499 A | 11/1999 | Catanzariti et al. |
| 6,144,448 A | 11/2000 | Mitoma |
| 6,189,580 B1 | 2/2001 | Thibault et al. |
| 6,218,176 B1 | 4/2001 | Berthold et al. |
| 6,271,034 B1 | 8/2001 | Bardarov et al. |
| 6,300,061 B1 | 10/2001 | Jacobs, Jr. et al. |
| 6,326,208 B1 | 12/2001 | Denney |
| 6,451,258 B1 | 9/2002 | Malmqvist |
| 6,544,729 B2 | 4/2003 | Sayler et al. |
| 6,555,312 B1 | 4/2003 | Nakayama |
| 6,719,719 B2 | 4/2004 | Carmel et al. |
| 6,818,185 B1 | 11/2004 | Petersen et al. |
| 7,001,719 B2 | 2/2006 | Wicks et al. |
| 7,087,226 B2 | 8/2006 | Ramachandran et al. |
| 7,125,727 B2 | 10/2006 | Massaro |
| 7,160,511 B2 | 1/2007 | Takahashi et al. |
| 7,166,425 B2 | 1/2007 | Madonna et al. |
| 7,244,612 B2 | 7/2007 | Goodridge |
| 7,284,900 B2 | 10/2007 | Mayer |
| 7,364,843 B2 | 4/2008 | Peak |
| 7,695,682 B2 | 4/2010 | Chojnacki et al. |
| 7,794,656 B2 | 9/2010 | Liang et al. |
| 7,972,773 B2 | 7/2011 | Madonna et al. |
| 8,021,343 B2 | 9/2011 | Nalesso et al. |
| 8,057,756 B2 | 11/2011 | Londo et al. |
| 8,092,990 B2 | 1/2012 | Voorhees |
| 8,124,024 B2 | 2/2012 | Ching et al. |
| 8,153,119 B2 | 4/2012 | Collins et al. |
| 8,182,804 B1 | 5/2012 | Collins et al. |
| 8,216,780 B2 | 7/2012 | Smith et al. |
| 8,329,889 B2 | 12/2012 | Collins et al. |
| 8,377,398 B2 | 2/2013 | McDevitt et al. |
| 8,455,186 B2 | 6/2013 | Smith et al. |
| 8,530,178 B2 | 9/2013 | Sobek et al. |
| 8,619,257 B2 | 12/2013 | Plowman et al. |
| 8,829,473 B1 | 9/2014 | Griswold et al. |
| 2002/0001539 A1 | 1/2002 | DiCesare et al. |
| 2003/0148536 A1 | 8/2003 | Liang et al. |
| 2004/0126783 A1 | 7/2004 | Bortolin et al. |
| 2004/0214200 A1 | 10/2004 | Brown et al. |
| 2005/0003346 A1 | 1/2005 | Voorhees et al. |
| 2005/0118719 A1 | 6/2005 | Schmidt et al. |
| 2005/0155438 A1 | 7/2005 | Belgardt |
| 2005/0206895 A1 | 9/2005 | Salmelainen |
| 2005/0273869 A1 | 12/2005 | Court et al. |
| 2006/0099115 A1 | 5/2006 | Sandberg |
| 2006/0205085 A1 | 9/2006 | Handique et al. |
| 2006/0210968 A1 | 9/2006 | Goodridge |
| 2006/0257991 A1 | 11/2006 | McDevitt et al. |
| 2007/0003950 A1 | 1/2007 | Shen et al. |
| 2007/0072174 A1 | 3/2007 | Sayler et al. |
| 2007/0178450 A1 | 8/2007 | Wheeler et al. |
| 2007/0263049 A1 | 11/2007 | Preckel et al. |
| 2007/0292397 A1 | 12/2007 | McNulty et al. |
| 2008/0003564 A1 | 1/2008 | Chen et al. |
| 2008/0153096 A1 | 6/2008 | Witty et al. |
| 2008/0193946 A1 | 8/2008 | McMillan |
| 2008/0241819 A1 | 10/2008 | Smith |
| 2008/0261294 A1 | 10/2008 | Noda et al. |
| 2008/0272283 A1 | 11/2008 | Feldsine et al. |
| 2008/0286757 A1 | 11/2008 | Gaisford et al. |
| 2009/0155768 A1 | 6/2009 | Scholl et al. |
| 2009/0155838 A1 | 6/2009 | Hale |
| 2010/0028916 A1* | 2/2010 | Ambar .................. C12Q 1/34 435/7.72 |
| 2010/0055669 A1 | 3/2010 | Luque et al. |
| 2010/0112549 A1* | 5/2010 | Rey .................. G01N 33/56911 435/5 |
| 2010/0133200 A1 | 6/2010 | Gin et al. |
| 2010/0157303 A1 | 6/2010 | Ono |
| 2010/0196877 A1 | 8/2010 | Smith et al. |
| 2010/0225920 A1 | 9/2010 | Xia et al. |
| 2011/0033847 A1 | 2/2011 | Walsh et al. |
| 2011/0076672 A1 | 3/2011 | Schofield |
| 2011/0097702 A1 | 4/2011 | Voorhees |
| 2011/0117025 A1 | 5/2011 | Dacosta et al. |
| 2011/0183314 A1 | 7/2011 | Smith |
| 2012/0003630 A1 | 1/2012 | Collins et al. |
| 2012/0071342 A1 | 3/2012 | Lochhead et al. |
| 2012/0134975 A1 | 5/2012 | Hyde et al. |
| 2012/0143024 A1 | 6/2012 | Phillips et al. |
| 2012/0225423 A1 | 9/2012 | Schwoebel et al. |
| 2012/0252699 A1 | 10/2012 | Jaffrey et al. |
| 2012/0288897 A1* | 11/2012 | Ching .................. B01F 11/0071 435/91.2 |
| 2012/0328576 A1 | 12/2012 | Jayasheela et al. |
| 2013/0122549 A1 | 5/2013 | Lu et al. |
| 2014/0134656 A1 | 5/2014 | Dortet et al. |
| 2014/0272928 A1 | 9/2014 | Rey et al. |
| 2015/0104787 A1 | 4/2015 | Rey et al. |
| 2015/0132795 A1 | 5/2015 | Griswold et al. |
| 2015/0148261 A1 | 5/2015 | Frei et al. |

FOREIGN PATENT DOCUMENTS

| | | |
|---|---|---|
| DE | 1994/4423935 A1 * | 1/1996 |
| EP | 0274527 | 7/1987 |
| EP | 0168933 | 4/1993 |
| WO | WO 87/06706 | 11/1987 |
| WO | WO 94/25572 | 11/1994 |
| WO | WO 02/081679 | 10/2002 |
| WO | WO 2005/085855 | 9/2005 |
| WO | WO 2006/075996 | 7/2006 |
| WO | WO 2007/115378 | 10/2007 |
| WO | WO 2010/096584 | 8/2010 |
| WO | WO 2013/049121 | 4/2013 |
| WO | WO 2014/160418 | 10/2014 |
| WO | WO 2014/164768 | 10/2014 |

OTHER PUBLICATIONS

KeyPath MRSA/MSSA Blood Culture Test—BT, 510(k) Summary, MicroPhage, Inc., Apr. 29, 2011, 15 pages.

Lampinen, J. et al., Comparison of flash and glow ATP assays with thermo scientific varioskan flash luminometry,: Application Note: AP-MIB-VARI012-0108, Thermo Scientific, 2008, 6 pages.

Luciferase Measurements using the Clarity Luminescence Microplate Reader. Luminescence made easy. Application Note, BioTek Instruments, Inc., 2006, 5 pages.

NucliSENS EasyQ MRSA Assay, 510(k) Summary, bioMerieux, Inc., Sep. 20, 2010, 23 pages.

Ulitzur, S. et al., "Introduction of lux genes into bacteria: a new approach for specific determination of bacteria and their antibiotic susceptibility," In: Schlomerich J. et al. (eds.), Bioluminescence and Chemiluminescence New Perspectives, Chichester: John Wiley and Sons (1987), pp. 463-472.

Vandercam, B. et al., "Amplification-based DNA analysis in the diagnosis of prosthetic joint infection," Journal of Molecular Diagnostics, 10(6):537-543 (2008).

Watanabe, T. et al., "Studies on luciferase from photobacterium phosphoreum," Journal of Biochemistry, 72(3):647-653 (1972).

International Search Report and Written Opinion for International Application No. PCT/US15/27519, mailed Sep. 11, 2015, 17 pages.

European Search Report for European Application No. 14779477.0, mailed Jun. 27, 2016.

Extended European Search Report .For European Application No, 14779477.0, mailed Aug. 17, 2016.

* cited by examiner

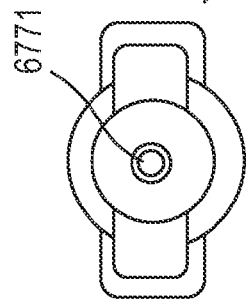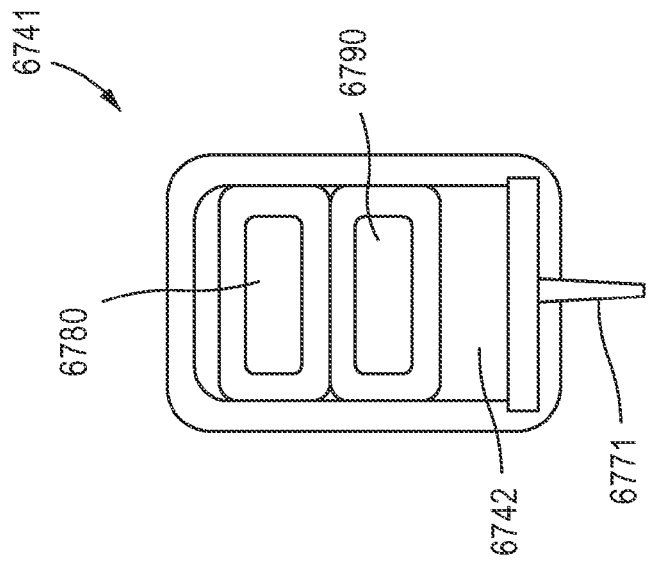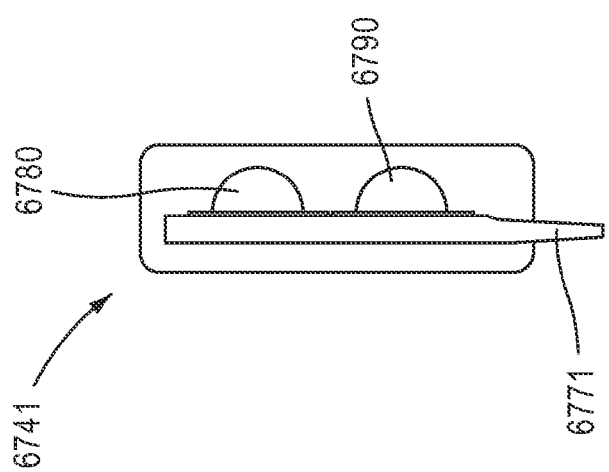

REAGENT CARTRIDGE AND METHODS FOR DETECTION OF CELLS

CROSS-REFERENCE TO RELATED APPLICATIONS

This application is a continuation-in-part of U.S. patent application Ser. No. 14/476,392, entitled "Reagent Cartridge and Methods for Detection of Cells," filed Sep. 3, 2014, which claims priority to and the benefit of U.S. Provisional Patent Application Ser. Nos. 61/983,765, entitled "Reagent Cartridge for Detection of Cells," filed Apr. 24, 2014; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, each of which is incorporated herein by reference in its entirety.

This application also claims priority to and the benefit of U.S. Provisional Patent Application Ser. Nos. 61/983,765, entitled "Reagent Cartridge for Detection of Cells," filed Apr. 24, 2014; and 61/939,126, entitled "Systems and Methods for Packaging Nucleic Acid Molecules into Non-Replicative Transduction Particles and Their Use as Cellular Reporters," filed Feb. 12, 2014, each of which is incorporated herein by reference in its entirety.

BACKGROUND

The embodiments described herein relate to systems and methods for detection of cells using engineered transduction particles. More particularly, the embodiments described herein also relate to a container and instrument within which the detection of bacteria can be performed in an integrated, closed system with walkaway functionality.

Detection of bacteria, especially drug resistant strains, is a critical step in diagnosing and limiting spread of bacterial infections. For example, MRSA is a drug-resistant version of the common *Staphylococcus aureus* bacteria that is carried by a significant portion of the population in the U.S. Most infections of MRSA occur in hospitals, and can have a high mortality rate (MRSA infections kill approximately 19,000 people in the U.S. every year). Accordingly, there is a need for efficient, accurate and rapid identification of the bacterial strains (including their phenotype and/or genotype and other molecular targets) that cause infection, such as MRSA. Particularly important is the ability to identify the bacterial phenotype and/or genotype and other molecular targets from a variety of different samples (e.g., human samples, environmental samples, plant samples, veterinary samples, food samples or the like), so that the appropriate treatment and control regimen can be started in a timely fashion.

One known method for identifying bacteria includes bacterial culture. Culturing is highly sensitive, but often takes 18 hours or more to yield a result, and is therefore not suitable for rapid diagnosis or for efficient screening purposes. Known culturing methods are often performed using systems that require highly trained personnel to perform the assay, and are therefore not suitable for use in a variety of different settings. Known culturing methods are also prone to contamination, which can result in false positives and/or misidentification of the bacteria. Moreover, known culturing methods employ specifically tailored culture protocols for identification of various bacterial species, thus testing a broad bacteria panel can rapidly elevate the cost.

Direct bacterial immunodetection, that is, detection using an antibody antigen reaction, is another method for bacterial detection. Known methods of immunodetection can produce results more quickly and at a lower cost than a culture, but are often limited by the availability of selective antibodies for the bacterial strain of interest and available antibodies are prone to cross-reactivity. Such known methods are also less sensitive than culturing, so there is often nevertheless a requirement of bacterial amplification that can lengthen the assay time.

Other known methods for detection of bacterial cells include isolation and analysis of nucleic acid such as DNA or RNA. Known methods for isolating nucleic acids from a sample often include several stringent sample preparation steps that require expensive and specialized equipment. In particular, such steps include 1) removing the proteins within a sample containing bacteria or cells by adding a protease; 2) breaking down the remaining bulk sample to expose the nucleic acids contained therein (also referred to as cell lysing); 3) precipitating the nucleic acid from the sample; 4) washing and/or otherwise preparing the nucleic acid for further analysis; 5) analyzing the nucleic acid to identify the species. After preparing the sample, known analysis methods can include polymerase chain reaction (PCR), gene sequencing, gene fingerprinting, fluorescence, immunoassay, electrochemical immunoassay, microarrays, any other suitable technique or a combination thereof. PCR has found widespread commercial usage but often requires multiple steps involving expensive reagents and instrumentation. Many known methods involving PCR are not suitable for bench top testing (e.g., they require relatively skilled personnel). Moreover, known PCR methods employ thermal cycling and/or elevated temperatures, which can increase the cost, time and/or complexity of the analysis. In addition, because nucleic acid amplification based techniques do not measure the response of a bacteria to an antibiotic, such techniques are not suitable for antibiotic susceptibility testing. Finally, because nucleic acid amplification methods lyse the sample cells, such methods cannot distinguish between live and dead cells.

Some known systems and methods for cell identification include the use of bacteriophages to identify and/or detect certain bacteria. In some known methods, phages that are tagged with a reporter molecule can be used to target and infect a specific bacterial strain. After infection, the phages can undergo a lytic cycle (i.e., break the cell wall killing the target bacteria) and/or a lysogenic cycle (i.e., replication of the phage along with the bacteria without killing the bacteria), followed by detection of the amplified progeny phage. Such known methods relying on phage detection often include limiting or complex steps. For example, some known phage detection-based methods for identification rely on phage replication (during which the bacteria can be lysed), and typically require cell culturing for facilitating this process. Some known phage detection-based methods require removal or "unbinding" of specifically bound phages from the samples using carefully metered and/or pH controlled reagents. Moreover, some known phage detection-based methods rely on careful metering of the amount of phage added and/or include opening or closing of the reaction chamber to add/remove reagents, which can lead to contamination and/or premature mixing of reagents leading to erroneous results and making the assay complex in nature.

Some known phage based systems and methods can result in undesirable and/or inconsistent delivery of reagents into a closed system. For example, some known systems and methods deliver reagents into a sample to facilitate a reaction that can be optically detected. Inconsistent and/or inaccurate delivery of such reagents can result in undesirable variability associated with the light detection, potentially false readings or the like. Some known systems employ sealed reagent containers or "blister packs" to isolate the reagents and the sample until delivery of the reagents is desired. To facilitate delivery of reagents from a blister pack, some known systems include mechanisms, such as rollers, to expel the reagent (see, e.g., WO2005/085855, FIG. 31). Other known systems include multiple puncturers to facilitate the rupture of a blister pack (see e.g., WO2007/115378, FIG. 16). Excessive "dead volume" (the volume within a blister pack after actuation that can contain the reagent), however, can result in inconsistent delivery times and/or amounts. Moreover, delivery mechanisms of known systems can produce undesired effects when the reagent is delivered (e.g., excessive splash or incomplete mixing). Thus, many known systems do not accommodate delivery of reagents associated with a flash luminescence reaction.

In addition to the above-described drawbacks regarding the use of phage-based methods, known methods do not employ automation or instrumentation for enabling a "walk away" bacteriophage identification system. For example, many known systems do not accommodate closed system handling and/or measurement of a signal that is produced by certain reporter molecules, such as for example, a flash luminescence reaction. Thus, known systems and methods require skilled personnel and intimate handling of the samples, which can increase the possibility of false positives or negatives.

Thus, a need exists for improved apparatus and methods for rapid, cost effective and facile detection and identification of bacterial species in clinical samples. In particular, a need exists for improved rupture structures and delivery paths within such systems. In addition, a need exists for improved apparatus and methods for efficient storage and transfer of clinical samples from a point of collection to a testing location.

SUMMARY

Systems and methods for detecting and/or identifying target cells (e.g., bacteria) using engineered vectors (including viral vectors) and/or transduction particles are described herein. In some embodiments, an apparatus includes a housing and an actuator. The housing, which defines a reagent volume that can receive a reagent container, can be removably coupled to a reaction chamber. The housing includes a puncturer that defines a transfer pathway in fluid communication with the reagent volume. A delivery portion of the housing defines a delivery pathway between the transfer pathway and the reaction chamber when the housing is coupled to the reaction chamber. The actuator has a plunger portion disposed within the reagent volume. An engagement portion of the actuator can be manipulated to move the plunger portion within the reagent volume to deform the reagent container. The puncturer can pierce a frangible portion of the reagent container to convey a reagent from the reagent container into the reaction chamber via the transfer pathway and/or the delivery pathway.

BRIEF DESCRIPTION OF THE DRAWINGS

FIGS. 25A-25C are a side view, a front view and a bottom view, respectively, of a housing assembly according to an embodiment.

DETAILED DESCRIPTION

Figure 1:
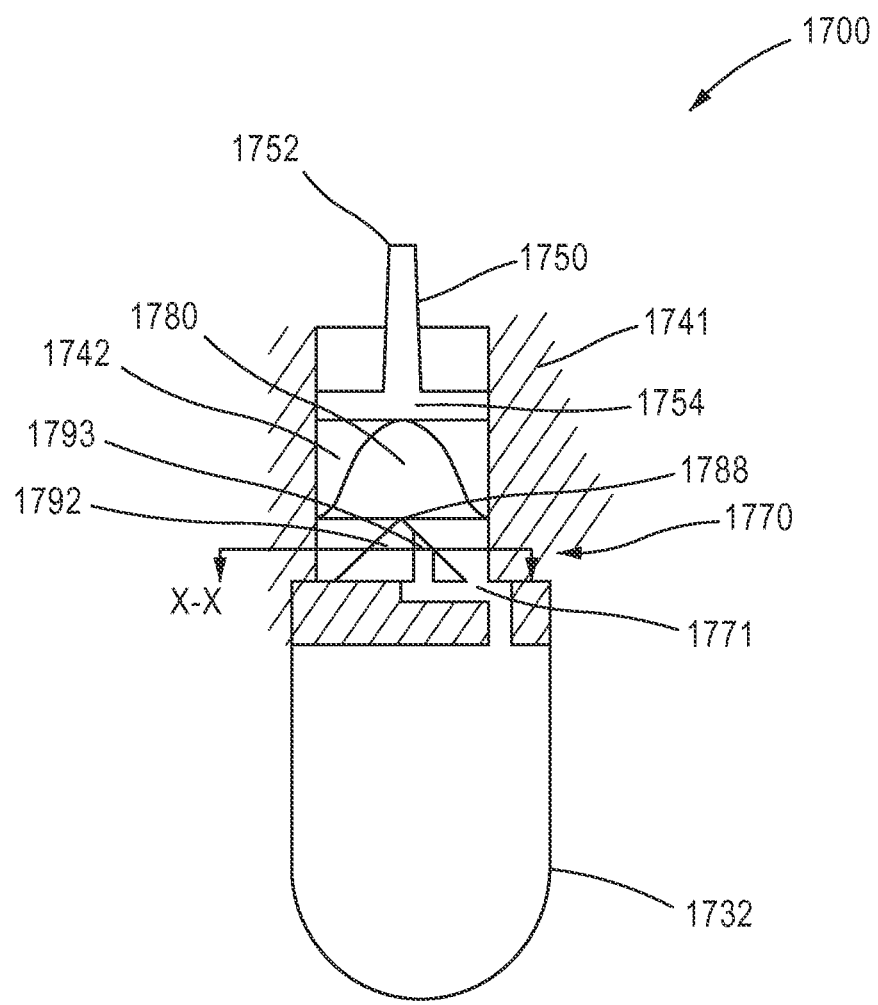
FIGS. 1-3 are schematic illustrations of a container assembly according to an embodiment, in a first configuration, second configuration and third configuration, respectively.

Systems and methods for detecting and/or identifying target cells (e.g., bacteria) using engineered vectors (including viral vectors) and/or transduction particles are described herein. In some embodiments, an apparatus includes a housing and an actuator. The housing, which defines a reagent volume that can receive a reagent container, can be removably coupled to a reaction chamber (e.g., which can contain a sample including a target cell). The reagent container can be disposed within the reagent volume, and can contain any suitable reagent or substance. For example, the reagent container can contain one or more transduction particles, a reagent formulated to react with one or more reporter molecules in a sample to enhance production of a signal or otherwise augment the signal or other assay components, tridecanal, a nutrient, an antibiotic, a lysis reagent, a sterilizing reagent and/or the like. The housing includes a puncturer that defines a transfer pathway in fluid communication with the reagent volume. A delivery portion of the housing defines a delivery pathway between the transfer pathway and the reaction chamber when the housing is coupled to the reaction chamber. In some embodiments, at least a portion of the delivery pathway can at least partially surround the puncturer. The actuator has a plunger portion disposed within the reagent volume. An engagement portion of the actuator can be manipulated to move the plunger portion within the reagent volume to deform the reagent container. The puncturer can pierce the frangible portion of the reagent container to convey a reagent from the reagent container into the reaction chamber via the transfer pathway and/or the delivery pathway.

In some embodiments, an apparatus includes a housing, a reagent container, an actuator, and a lock member. The housing can be removably coupled to a reaction chamber (e.g., which can contain a target cell). The housing defines a reagent volume and includes a delivery portion that defines a delivery pathway. The delivery pathway places the reagent volume in fluid communication with the reaction chamber when the housing is coupled to the reaction chamber. The delivery portion has a puncturer in fluid communication with the delivery pathway. The reagent container is disposed within the reagent volume of the housing and can contain any suitable reagent or substance. For example, the reagent container can contain one or more transduction particles, a reagent formulated to react with one or more reporter molecules in a sample to enhance production of a signal or otherwise augment the signal or other assay components, tridecanal, a nutrient, an antibiotic, a lysis reagent, a sterilizing reagent and/or the like. The reagent container has a frangible portion and a skirt surrounding the frangible portion. The actuator includes a plunger portion disposed within the reagent volume. The actuator can be manipulated to move the plunger portion within the reagent volume to deform the reagent container from a first configuration to a second configuration. The puncturer is configured to pierce the frangible portion of the reagent container to convey a reagent from the reagent container into the reaction chamber via the delivery pathway when the reagent container is in the second configuration. The lock member can maintain the skirt in contact with a shoulder of the delivery portion of the housing when the reagent container is in the second configuration to maintain a substantially fluid-tight seal between the skirt and the shoulder.

In some embodiments, an apparatus includes a housing, a reagent container, and an actuator. The housing can be removably coupled to a reaction chamber (e.g., which can contain a target cell). The housing includes a delivery portion that defines a delivery pathway and includes a puncturer in fluid communication with the delivery pathway. The delivery pathway places the reagent volume in fluid communication with the reaction chamber when the housing is coupled to the reaction chamber. The reagent container is disposed within the reagent volume of the housing and can contain any suitable reagent or substance. For example, the reagent container can contain one or more transduction particles, a reagent formulated to react with one or more reporter molecules in a sample to enhance production of a signal or otherwise augment the signal or other assay components, tridecanal, a nutrient, an antibiotic, a lysis reagent, a sterilizing reagent and/or the like. The reagent container includes a contact portion, a frangible portion, and a skirt surrounding the frangible portion. The actuator has a plunger portion disposed within the reagent volume. The plunger portion can correspond to one or more of the contact portion of the reagent container or the puncturer. The actuator can be manipulated to move the plunger portion within the reagent volume such that the plunger portion engages the contact portion of the reagent container to deform the reagent container from a first configuration to a second configuration. The puncturer is configured to pierce the frangible portion of the reagent container to convey a reagent from the reagent container into the reaction chamber via the delivery pathway when the reagent container is in the second configuration.

In some embodiments, a method includes disposing a sample into a reaction chamber. The reaction chamber is packaged to contain a reagent (e.g., a liquid or dry composition, such as a tablet) formulated to mix with the sample to form an assay media. One or more transduction particles associated with a cell phenotype are mixed with the sample in the reaction chamber. The one or more transduction particles are engineered to include a nucleic acid molecule formulated to cause the cell phenotype to produce one or more reporter molecules. The reagent is formulated to suppress production of the one or more reporter molecules in a portion of the cell phenotype. The reagent can include any suitable substance. For example, the reagent can include an antibiotic and/or a colorant. A first signal associated with the reagent is received. The first signal can be associated with any suitable characteristic of the reagent, such as a color of the reagent, and can therefore be used to indicate and/or confirm the presence of the reagent. The sample and the one or more transduction particles are maintained when the first signal indicates the presence of the reagent to express the one or more reporter molecules when the cell phenotype is present in the sample. A second signal associated with a quantity of the one or more reporter molecules is received. In some embodiments, a substance formulated to react with the one or more reporter molecules can be disposed into the sample to generate or enhance the second signal.

In some embodiments, a method includes receiving a container that contains a swab and a transport media. The swab includes a shaft and a collection portion constructed from non-wound material. The transport media includes a sample released from the collection portion. The collection portion can be constructed from and/or includes any suitable material of non-wound construction. For example, the collection portion can be constructed from and/or include a foam material. The transport media and the sample are transferred into a reaction chamber. The transport media is mixed in the reaction chamber with one or more transduction particles associated with a target cell. The one or more transduction particles are engineered to include a nucleic acid molecule formulated to cause the target cell to produce one or more reporter molecules. The one or more reporter molecules can include any suitable substance. For example, the one or more reporter molecules can include a bacterial luciferase, a eukaryotic luciferase, a fluorescent protein, an enzyme suitable for colorimetric detection, a protein suitable for immunodetection, a peptide suitable for immunodetection, and/or a nucleic acid that functions as an aptamer or that exhibits enzymatic activity. The mixture of the transport media and the one or more transduction particles is maintained at a temperature of at least 20 degrees Celsius for a period of about eight hours or less to express the one or more reporter molecules when the target cell is present in the sample. A signal associated with a quantity of the one or more reporter molecules can be received.

In other embodiments, the collection portion may be added to or disposed within the reaction chamber directly. In such embodiments, the collection portion may remain in the reaction chamber throughout the assay or it may be removed from the reaction chamber after the sample on the collection portion is released into the reaction chamber.

As described herein, the terms "gene," "DNA" and "nucleotide" mean the whole or a portion of the genetic sequence of the target bacteria or the vector.

As described herein, the term "plasmid" means the engineered gene, sequence and/or molecule contained within the vector that includes regulatory elements, nucleic acid sequences homologous to target genes, and various reporter constructs for causing the expression of reporter molecules within a viable cell and/or when an intracellular molecule is present within a target cell.

A "transduction particle" refers to a virus capable of delivering a non-viral nucleic acid molecule into a cell. The virus can be a bacteriophage, adenovirus, etc. A "non-replicative transduction particle" refers to a virus capable of delivering a non-viral nucleic acid molecule into a cell, but does not package its own replicated viral genome into the transduction particle. The virus can be a bacteriophage, adenovirus, etc.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

As used herein, a "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, rue, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be the reporter nucleic acid molecule itself, such as an aptamer or ribozyme.

In some embodiments, the reporter nucleic acid molecule is operatively linked to a promoter. In other aspects, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, a term referring to multiple components or portions thereof is intended to refer to a first component or a first portion thereof, and/or a second component or a second portion thereof, unless the context clearly dictates otherwise. Thus, for example, the term "puncturers" is intended to refer to a "first puncturer" and/or a "second puncturer."

As used herein, the terms "about" and "approximately" generally mean plus or minus 10% of the value stated. For example, about 0.5 would include 0.45 and 0.55, about 10 would include 9 to 11, about 1000 would include 900 to 1100.

The term "fluid-tight" is understood to encompass both a hermetic seal (i.e., a seal that is gas-impervious) as well as a seal that is liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 psig, less than about 10 psig, less than about 20 psig, less than about 30 psig, less than about 50 psig, less than about 75 psig, less than about 100 psig and all values in between. Similarly, a "substantially liquid-tight" seal includes a seal that prevents the passage of a liquid (e.g., a liquid medicament) therethrough when the seal is maintained at a constant position and is exposed to liquid pressures of less than about 5 psig, less than about 10 psig, less than about 20 psig, less than about 30 psig, less than about 50 psig, less than about 75 psig, less than about 100 psig and all values in between.

Figure 2:
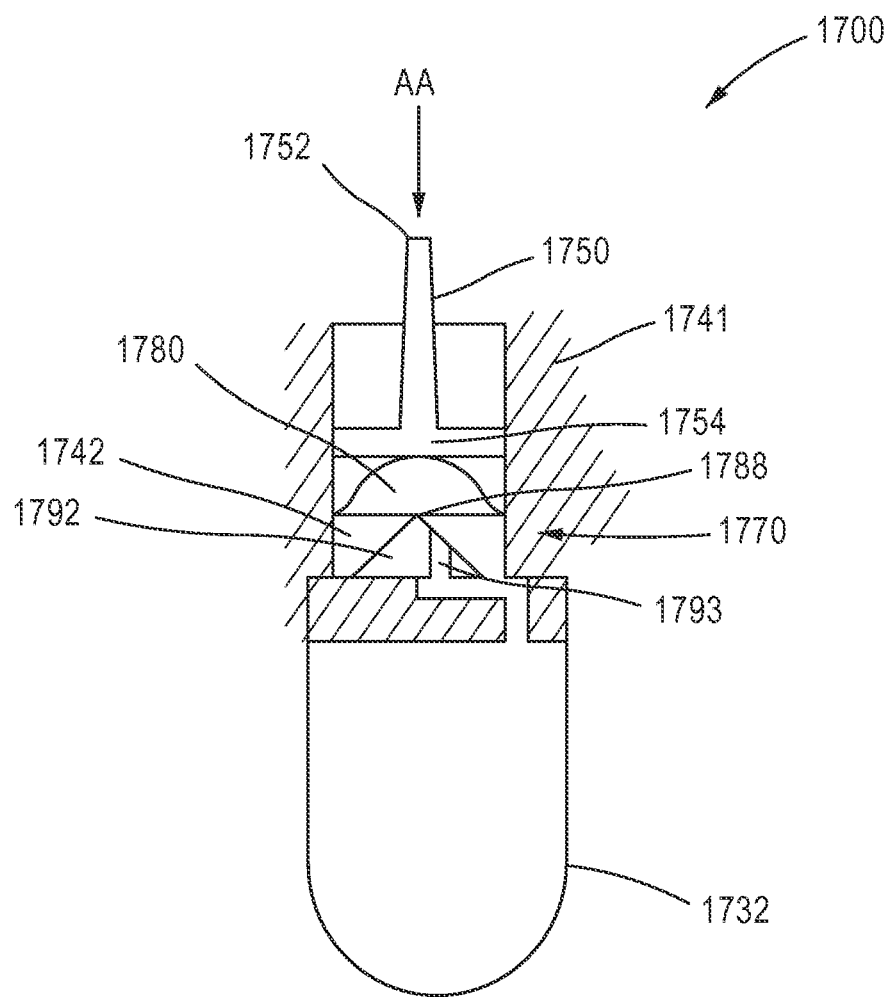
Figure 3:
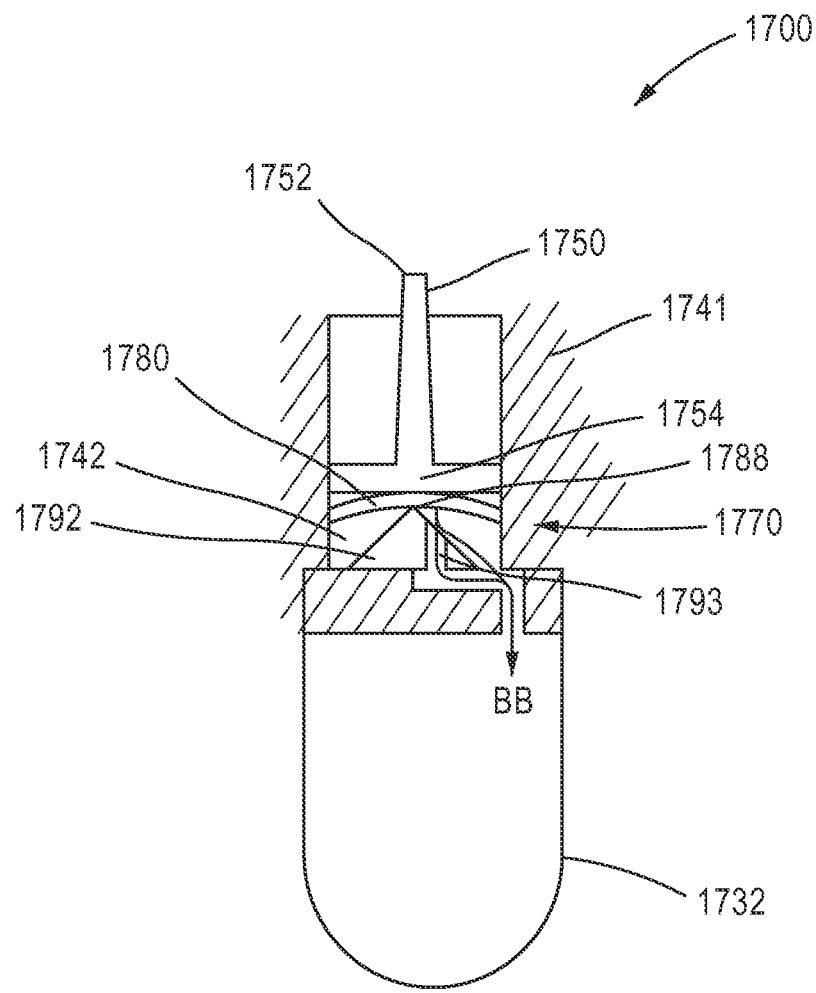

FIGS. 1-3 show a container assembly 1700 according to an embodiment in a first configuration (FIG. 1), a second configuration (FIG. 2), and a third configuration (FIG. 3). The container assembly 1700 can be used with and manipulated by any of the instruments and/or any of the components described herein and in U.S. patent application Ser. No. 13/802,461, entitled "Systems and Methods for Detection of Cells using Engineered Transduction Particles," ("the '461 application") which is incorporated herein by reference in its entirety. In this manner, the container assembly 1700 and any of the container assemblies described herein can be used to detect and/or identify target cells (e.g., bacteria) within a sample according to any of the methods described herein or in the '461 application. For example, in some embodiments, the container assembly 1700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 1700 is used in methods of cell identification and/or detection that do not involve removal of contents from the container assembly 1700, separation of the contents within the container assembly 1700, washing of the contents within the container assembly 1700 and/or rinsing of the contents within the container assembly 1700.

The container assembly 1700 includes a housing 1741, an actuator 1750, and a reaction chamber 1732. The housing 1741 is removably coupled to the reaction chamber 1732. For example, in some embodiments, the housing 1741 can be threadedly coupled to the reaction chamber 1732. In other embodiments, the housing 1741 and the reaction chamber 1732 can form an interference fit to couple the housing 1741 to the reaction chamber 1732. The housing 1741 defines a reagent volume 1742 configured to receive a reagent container 1780. The housing 1741 includes a puncturer 1792 and a delivery portion 1770. In some embodiments, the housing 1741, the delivery portion 1770 and/or the puncturer 1792 can be monolithically constructed. In other embodiments, the housing 1741, the delivery portion 1770 and/or the puncturer 1792 can be formed separately and then joined together.

Figure 4:
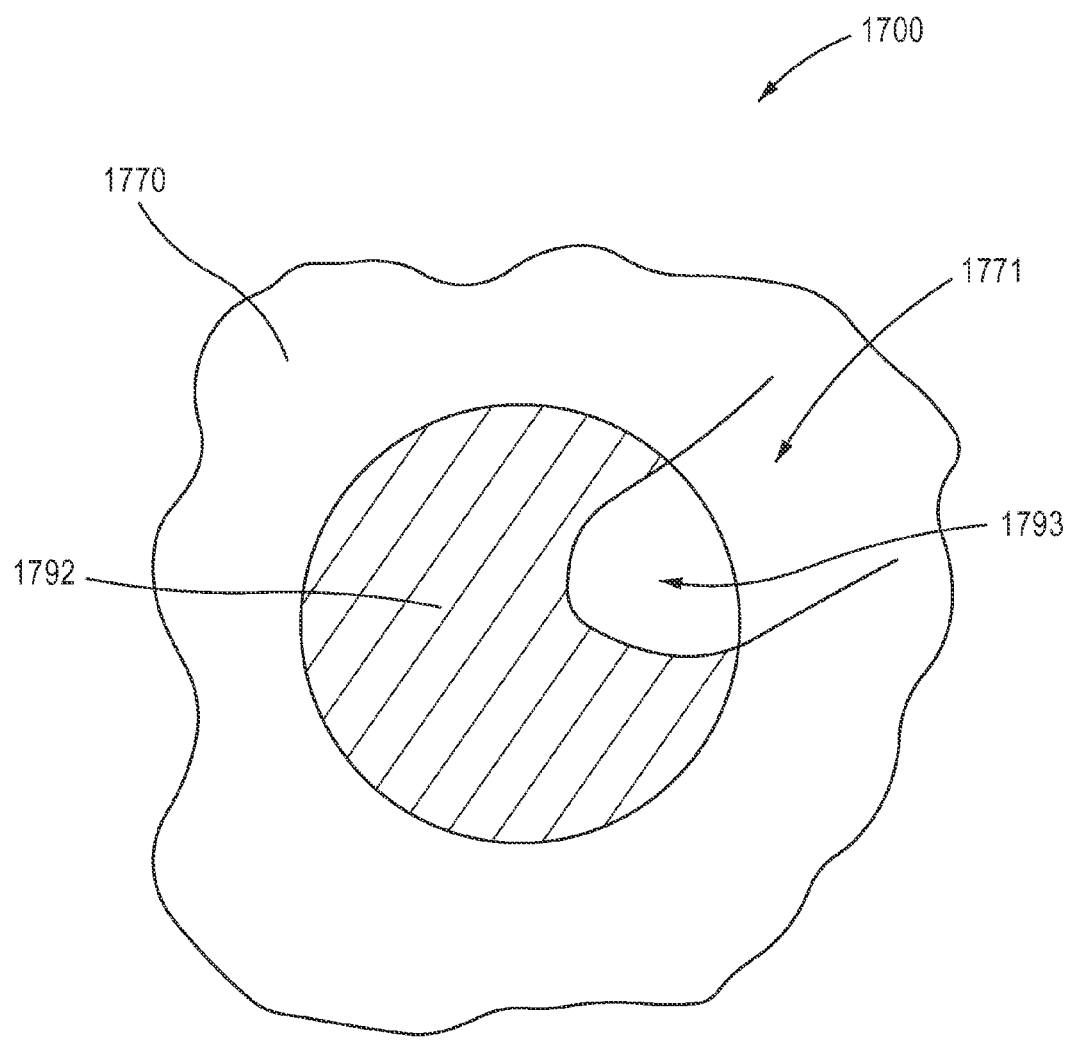
FIG. 4 is a cross-section view of a portion of the container assembly shown in FIGS. 1-3 taken along the line X-X in FIG. 1.

The puncturer 1792 is configured to pierce (e.g., rupture) a frangible portion 1788 of the reagent container 1780 to convey a reagent from the reagent container 1780 into the reaction chamber 1732. As shown in FIGS. 1-3, the puncturer 1792 includes a structure that terminates in a single sharp point configured to pierce the reagent container 1780. Moreover, the structure of the puncturer 1792 defines a transfer pathway 1793 in fluid communication with the reagent volume 1742. As shown in FIG. 4, in some embodiments, the inclusion of the transfer pathway 1793 results in a discontinuous cross-sectional shape in the puncturer 1792 (the cross-sectional view is shown below or "downstream" from the single sharp point). Thus, as described in more detail herein, when the puncturer 1792 pierces the reagent container 1780, the transfer pathway 1793 provides a pathway through which the contents of the reagent container 1780 can flow. As shown, the pathway 1793 is non-parallel to the frangible portion 1788 of the reagent container 1780. In particular, the pathway 1793 is substantially perpendicular to the frangible portion 1788 of the reagent container 1780. Said another way, the pathway 1793 is aligned with and/or parallel to the direction of motion of the actuator 1750 (see arrow AA). Moreover, the arrangement of the transfer pathway 1793 and/or the cross-sectional shape of the puncturer 1792 can limit clogging or obstructions that may result from the piercing, as well as "dead volume" after actuation, thus providing a more repeatable delivery of the contents of the reagent container 1780.

Although shown as including a single sharp point, in other embodiments, a puncture can include a sharp edge (e.g., a linear edge) and/or series of protrusions configured to pierce the reagent container. In such embodiments, for example, the structure supporting or defining each of the series of protrusions can define a transfer pathway (similar to the transfer pathway 1793).

Although shown as being a substantially linear pathway that is parallel to the frangible portion 1788, in other embodiments, the transfer pathway 1793 can have any suitable shape, direction and/or configuration, such as for example, a helical shape, a tapered shape or the like. Although the cross-sectional shape of the transfer pathway 1793 is shown in FIG. 4 as being curved and/or semi-circular, in other embodiments, the cross-sectional shape of the transfer pathway 1793 can have any suitable shape. Moreover, the shape and/or size of the transfer pathway 1793 can be variable (e.g., as a function of the distance from the puncturing tip). Although the puncturer 1792 is shown as including a single transfer pathway 1793, in other embodiments, a puncturer can define any suitable number of transfer pathways.

The delivery portion 1770 is configured to facilitate the delivery of the contents from the reagent container 1780 and/or the reagent volume 1742 into the reaction chamber 1732. Thus, as shown, the delivery portion 1770 can provide any suitable pathway and/or mechanism for delivering transduction particles and/or reagents disposed in the reagent container 1780 and/or reagent volume 1742 into the reaction chamber 1732. In particular, the delivery portion 1770 defines a delivery pathway 1771 between the transfer pathway 1793 and the reaction chamber 1732. The delivery pathway 1771 can have any suitable size and/or shape, and can accommodate any desired flow rate therethrough. For example, in some embodiments, the transfer pathway 1793 and/or the delivery pathway 1771 can accommodate any suitable flow rate, e.g., 1 ml/sec, 2 ml/sec, 3 ml/sec, 4 ml/sec, 5 ml/sec.

The actuator 1750 has a plunger portion 1754 disposed within the reagent volume 1742 and an engagement portion 1752. The engagement portion 1752 of the actuator 1750 is configured to be manipulated to move the plunger portion 1754 within the reagent volume 1742 to deform the reagent container 1780. In this manner, movement of the plunger portion 1754 can urge the frangible portion 1788 of the reagent container 1780 against the puncturer 1792 to pierce and/or rupture the frangible portion 1788. The plunger portion 1754 of the actuator 1750 and a portion of the housing 1741 can collectively define a seal to fluidically and/or optically isolate the reagent volume 1742 from a volume outside of the housing 1741.

The reagent container 1780 can be completely or partially filled with any suitable reagent or substance. For example, the reagent container 1780 can contain transduction particles that include an engineered nucleic acid formulated to cause the target cell (e.g., bacteria) to produce one or more reporter molecules. In some embodiments, the reagent container 1780 can contain one or more transduction particles engineered to be incapable of replication (e.g., lytic replication, lysogenic replication). For example, in some embodiments, the reagent container 1780 can contain any of the transduction particles described herein and in U.S. Provisional Application Nos. 61/983,765, entitled "Reagent Cartridge for Detection of Cells," filed Apr. 24, 2014; 61/779,177, entitled "Non-Replicative Transduction Particles and Transduction Particle-Based Reporter Systems," filed Mar. 13, 2013; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, and International Patent Application No. PCT/US2014/026536, entitled "Non-Replicative Transduction Particles and Transduction Particle-Based Reporter Systems," filed Mar. 13, 2014, each of which is incorporated herein by reference in its entirety.

In some embodiments, the reagent container can contain a reagent formulated to react with one or more reporter molecules to generate and/or enhance production of a signal. For another example, the reagent container 1780 can include a substrate, such as tridecanal, that can interact with a reporter molecule (e.g., luciferase), to produce a measurable signal, e.g., via a luminescence reaction. For yet another example, in some embodiments, the reagent container 1780 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The reagent container 1780 can be shaped and sized to be disposed substantially inside the reagent volume 1742. The reagent container 1780 can be constructed from materials that are substantially impermeable to and/or substantially chemically inert from the substance contained therein (e.g., transduction particle, substrate, antibiotics, buffers, surfactants, or any other reagent that can be used with the detection assay) and the outside environment. At least a portion of the reagent container 1780 (e.g., the frangible portion 1788) can be constructed from a material (e.g., polymer film, such as any form of polypropylene) having certain temperature characteristics such that the desired properties and integrity are maintained over a certain temperature. For example, in some instances, it can be desirable to store the reagent container 1780 containing reagent and/or substrate in a refrigerated condition. In some embodiments, a portion of the reagent container 1780 can be constructed from bi-axially oriented polypropylene (BOP). In some embodiments, a portion of the reagent container 1780 can be constructed from aluminum. In some embodiments, a portion of the reagent container 1780 can be constructed from polyvinyl chloride (PVC), ethylene vinyl alcohol (EVOH), polyethylene (PE) and/or polychlorotrifluoroethene (PCTFE or PTFCE).

The reaction chamber 1732 is configured to contain a sample and/or other reagents, and can be formed from any suitable material, for example, glass, plastic (e.g., polypropylene), acrylic, etc. In some embodiments, the reaction chamber 1732 can be formed from a lightweight, rigid and/or inert material. At least a portion of the reaction chamber 1732 (e.g., the distal end portion) can be at least partially transparent to allow viewing, optical access and/or detection of the internal volume of the reaction chamber 1732. In some embodiments, the distal end portion of the reaction chamber 1732 can be polished to promote optimal transmission of light therethrough. Although shown as being shaped as a cylinder with a rounded bottom, in other embodiments, the reaction chamber 1732 can have any other suitable shape, e.g., square, rectangular, oval, polygonal, elliptical, conical, etc. For example, in some embodiments, the reaction chamber 1732 can have a substantially flat bottom. In some embodiments, the reaction chamber 1732 can have a diameter of 12 mm and a height of 75 mm. In some embodiments, the container assembly 1700 can be provided with one or more solutions/reagents in liquid and/or dried form (e.g., bacterial nutrient solution, buffers, surfactants, transduction particle, colorants and/or antibiotics), predisposed within the reaction chamber 1732. In some instances, the reaction chamber 1732 can contain any suitable reagent and/or substance. For example, in some embodiments, the reaction chamber 1732 can contain one or more transduction particles, a reagent formulated to react with one or more reporter molecules in a sample to generate and/or enhance production of a signal, a nutrient, an antibiotic, a lysis reagent, a sterilizing reagent, a colorant and/or the like.

As shown in FIG. 1, the container assembly 1700 is in a first configuration. In the first configuration, the actuator 1750 is positioned such that the reagent container 1780 disposed within the housing 1741 is substantially undeformed. Similarly stated, the actuator 1750 is positioned such that it does not cause puncturer 1792 to pierce the reagent container 1780. Thus, the container assembly 1700 is in a "ready" state when in the first configuration. In some embodiments, the container assembly 1700 can include a safety mechanism (not shown) to prevent and/or limit movement of the actuator 1750 relative to the housing 1741 until desired by the operator.

To actuate the container assembly 1700, a force is applied to the engagement portion 1752 of the actuator 1750, thus causing the actuator 1750 to move as shown by the arrow AA in FIG. 2. As shown in FIG. 2, the container assembly 1700 is in a second (or "intermediate") configuration. In the second configuration, the actuator 1750 is positioned such that the reagent container 1780 is partially deformed. Similarly stated, the actuator 1750 is positioned such that at least a portion of the force is transferred to the reagent container 1780. As such, at least a portion of the reagent container 1780 becomes deformed. In some instances, in the second configuration, the puncturer 1792 can at least partially pierce a portion (e.g., the frangible portion 1788) of the reagent container 1780, thereby placing the internal volume of the reagent container 1780 in fluid communication with the transfer pathway 1793 and/or the delivery pathway 1771.

As shown in FIG. 3, the container assembly 1700 is in a third (or "deployed") configuration. In the third configuration, the actuator 1750 is positioned such that the reagent container 1780 is substantially deformed. Similarly stated, the actuator 1750 is positioned such that at least a portion of the force is transferred to the reagent container 1780. In such a configuration, the puncturer 1792 has pierced the reagent container 1780 (e.g., the frangible portion 1788), such that the contents of the reagent container have substantially exited the reagent container 1780 and entered the delivery portion 1770 and/or the reaction chamber 1732 via the transfer pathway 1793, as shown by the arrow BB.

In use, the actuator 1750 (e.g., the engagement portion 1752) is manipulated to move the plunger portion 1754 within the housing 1741 such that the plunger portion 1754 engages a contact portion (not identified in FIGS. 1-3) of the reagent container 1780 to partially deform the reagent container 1780 from the first configuration to the second configuration. As the plunger portion 1754 engages the contact portion of the reagent container 1780, the puncturer 1792 pierces a portion of the reagent container 1780 (e.g., a frangible portion 1788) to convey a reagent from the reagent container 1780 into the reaction volume 1742, the delivery portion 1770, and/or the reaction chamber 1732, at least in part via the transfer pathway 1793. From the second configuration to the third configuration, the actuator 1750 is manipulated to move the plunger portion 1754 within the housing 1741 such that the plunger portion 1754 engages a contact portion of the reagent container 1780 to deform the reagent container 1780 from the second configuration to the third configuration. As the reagent container 1780 deforms from the second configuration to the third configuration, substantially all of its contents (e.g., a reagent) is conveyed from the reagent container 1780 into the reaction volume 1742, the delivery portion 1770, and/or the reaction chamber 1732, such that "dead volume" in the reagent container 1780 is limited. In this manner, substantially repeatable delivery of the contents from the reagent container 1780 to the reaction chamber 1732 can be obtained. For example, in some embodiments, a deformation of a first reagent container at a first time and a deformation of a second reagent container at a second time after the first time can be substantially similar, thereby allowing for substantially all of the contents to be transferred from the reagent container 1780 at the first time and the second time. Moreover, this arrangement can limit clogging or obstructions that may result from the piercing of the reagent container 1780, thus providing a more repeatable delivery of the contents of the reagent container 1780.

Figure 5:
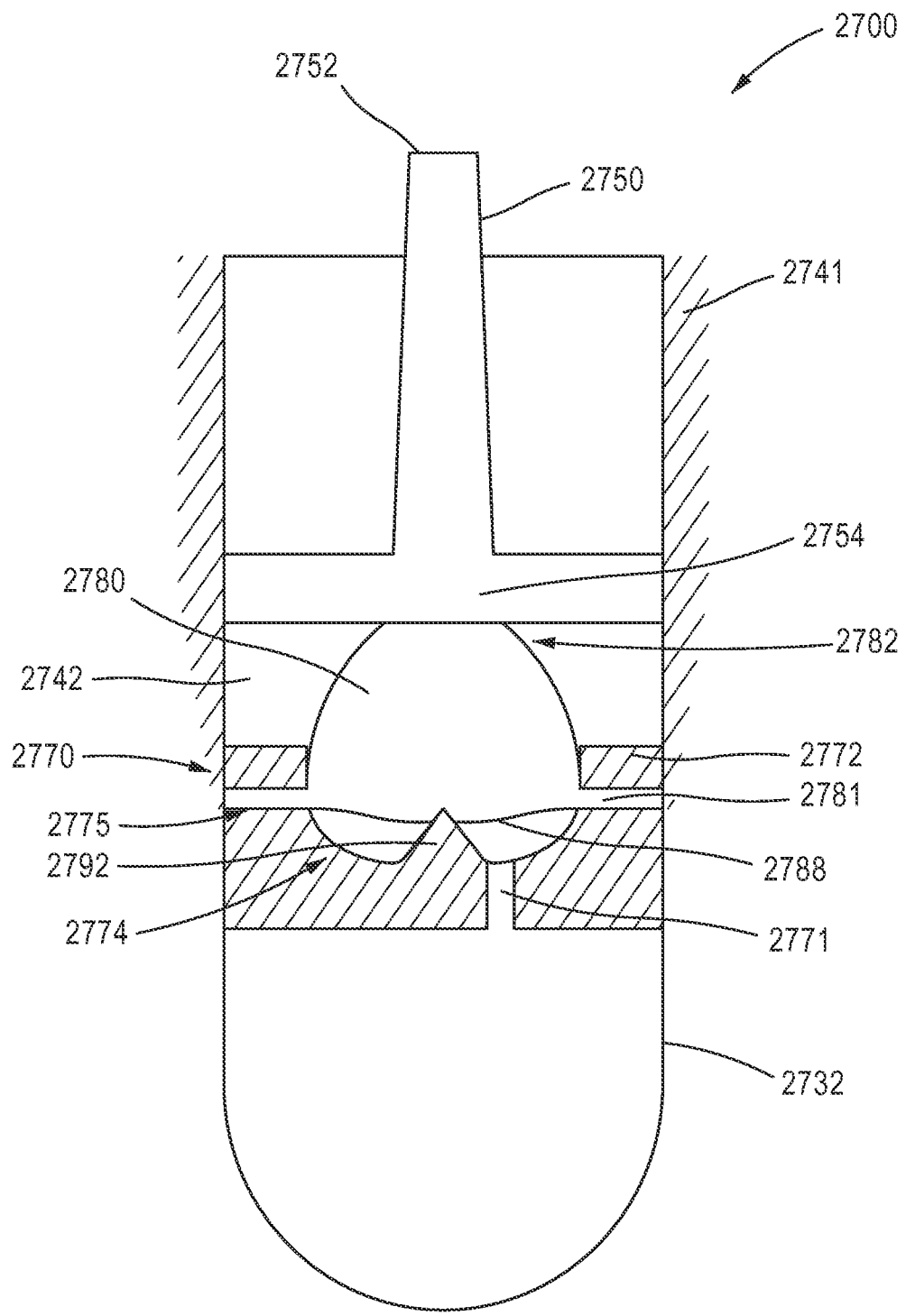
FIG. 5 is a schematic illustration of a container assembly according to an embodiment.

FIG. 5 shows a container assembly 2700 according to an embodiment. The container assembly 2700 can be used with and manipulated by any of the instruments and/or any of the components described herein and in the '461 application, which is incorporated herein by reference in its entirety. In this manner, the container assembly 2700 and any of the container assemblies described herein can be used to detect and/or identify target cells (e.g., bacteria) within a sample according to any of the methods described herein or in the '461 application. For example, in some embodiments, the container assembly 2700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 2700 is used in methods of cell identification and/or detection that do not involve removal of contents from the container assembly 2700, separation of the contents within the container assembly 2700, washing of the contents within the container assembly 2700 and/or rinsing of the contents within the container assembly 2700.

The container assembly 2700 includes a housing 2741, a reaction chamber 2732, a reagent container 2780, an actuator 2750, and a lock member 2772. The housing 2741 is removably coupled to the reaction chamber 2732. For example, in some embodiments, the housing 2741 can be threadedly coupled to the reaction chamber 2732. In other embodiments, the housing 2741 and the reaction chamber 2732 can form an interference fit to couple the housing 2741 to the reaction chamber 2732. The housing 2741 defines a reagent volume 2742 and includes a delivery portion 2770. The delivery portion 2770 includes a puncturer 2792. In some embodiments, the housing 2741, the delivery portion 2770, and/or the puncturer 2792 can be monolithically constructed. In other embodiments, the housing 2741, the delivery portion 2770, and/or the puncturer 2792 can be formed separately and then joined together.

The delivery portion 2770 is configured to facilitate the delivery of the contents from the reagent container 2780 and/or the reagent volume 2742 into the reaction chamber 2732. Thus, as shown, the delivery portion 2770 can provide any suitable pathway and/or mechanism for delivering contents disposed in the reagent container 2780 and/or reagent volume 2742 into the reaction chamber 2732. In particular, the delivery portion 2770 defines a delivery pathway 2771 between the reagent volume 2742 and the reaction chamber 2732. The delivery pathway 2771 can have any suitable size and/or shape, and can accommodate any desired flow rate therethrough. For example, in some embodiments, the delivery pathway 2771 can accommodate any suitable flow rate, e.g., 1 ml/sec, 2 ml/sec, 3 ml/sec, 4 ml/sec, 5 ml/sec. Moreover, the shape and/or size of the delivery pathway 2771 can be variable. Although the delivery portion 2770 is shown as including a single delivery pathway 2771, in other embodiments, a delivery portion can define any suitable number of delivery pathways.

Moreover, the delivery portion 2770 (and any of the delivery portions described herein) can include any suitable features, such as the delivery pathway 2771, surface geometry, surface coating or the like. For example, as shown, the delivery portion 2770 includes a concave surface 2774. In this manner, the delivery portion 2770 can facilitate the delivery of the contents from the reagent container 2780 and/or the reagent volume 2742 into the reaction chamber 2732. For example, the contents of the reagent container 2780 can be transferred along (e.g., based at least in part on gravitational force) the concave surface of the delivery portion 2770 and into the reaction chamber 2732 via the delivery pathway 2771. In other embodiments, however, the delivery portion 2770 need not have a concave surface.

The puncturer 2792 of the delivery portion 2770 is configured to pierce (e.g., rupture) a frangible portion 2788 of the reagent container 2780 to convey a reagent from the reagent container 2780 into the reaction chamber 2732. Thus, the puncturer 2792 can include any sharp point, sharp edge and/or series of protrusions configured to pierce the reagent container 2780. In some embodiments, the arrangement of and/or the shape of the puncturer can limit clogging and/or obstructions that may result from the piercing, thus providing a more repeatable delivery of the contents of the reagent container 2780. For example, in some embodiments, the puncturer 2792 can define one or more transfer pathways, similar to those shown and described herein (e.g., in FIGS. 1-3). Thus, the puncturer 2792 is in fluid communication with the delivery pathway 2771 of the delivery portion 2770. In this manner, and as described in more detail herein, the puncturer can facilitate the transfer of the contents of the reagent container 2780 to the reaction chamber 2732.

The reagent container 2780 can be completely or partially filled with any suitable reagent or substance. For example, the reagent container 2780 can contain transduction particles that include an engineered nucleic acid formulated to cause the target cell (e.g., bacteria) to produce one or more reporter molecules. In some embodiments, the reagent container 2780 can contain one or more transduction particles engineered to be incapable of replication (e.g., lytic replication, lysogenic replication). For example, in some embodiments, the reagent container 2780 can contain any of the transduction particles described herein and in U.S. Provisional Application Nos. 61/983,765, entitled "Reagent Cartridge for Detection of Cells," filed Apr. 24, 2014; 61/779,177, entitled "Non-Replicative Transduction Particles and Transduction Particle-Based Reporter Systems," filed Mar. 13, 2013; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, and International Patent Application No. PCT/US2014/026536, entitled "Non-Replicative Transduction Particles and Transduction Particle-Based Reporter Systems," filed Mar. 13, 2014, each of which is incorporated herein by reference in its entirety.

In some embodiments, the reagent container 2780 can contain a reagent formulated to react with one or more reporter molecules to enhance production of a signal. For another example, the reagent container 2780 can include a substrate, such as tridecanal, that can interact with a reporter molecule (e.g., luciferase), to produce a measurable signal, e.g., via a luminescence reaction. For yet another example, in some embodiments, the reagent container 2780 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The reagent container 2780 can be shaped and sized to be disposed substantially inside the reagent volume 2742. The reagent container 2780 can be constructed from materials that are substantially impermeable to and/or substantially chemically inert from the substance contained therein, e.g., transduction particle, substrate, antibiotics, buffers, surfactants, or any other reagent that can be used with the detection assay. At least a portion of the reagent container 2780 (e.g., the frangible portion 2788) can be constructed from a material (e.g., polymer film, such as any form of polypropylene) having certain temperature characteristics such that the desired properties and integrity are maintained over a certain temperature. For example, in some instances, it can be desirable to store the reagent container 2780 containing reagent and/or substrate in a refrigerated condition. In some embodiments, a portion of the reagent container 2780 can be constructed from bi-axially oriented polypropylene (BOP). In some embodiments, a portion of the reagent container 2780 can be constructed from aluminum. In some embodiments, a portion of the reagent container 2780 can be constructed from polyvinyl chloride (PVC), ethylene vinyl alcohol (EVOH), polyethylene (PE) and/or polychlorotrifluoroethene (PCTFE or PTFCE).

The reagent container 2780 has a skirt 2781 and a frangible portion 2788. The skirt 2781 surrounds at least a portion of the frangible portion 2788. As shown, the skirt 2781 is disposed between the lock member 2772 and a shoulder portion 2775 of the delivery portion 2770 of the housing 2741. In this manner, and as discussed in further detail herein, the skirt 2781 can be secured (e.g., grabbed, grasped, held, pinched, interference fitted, etc.) at least in part by the lock member 2772. As such, the skirt 2781 can provide a securement function such that a position of the reagent container 2780 can be substantially maintained during use. The skirt 2781 can be any suitable size and/or shape, and can include any suitable surface design (e.g., smooth, rough and/or the like). For example, in some embodiments, the skirt 2781 can be sized and/or shaped to correspond to a portion of the lock member 2772.

The actuator 2750 has a plunger portion 2754 disposed within the reagent volume 2742 and an engagement portion 2752. The engagement portion 2752 of the actuator 2750 is configured to be manipulated to move the plunger portion 2754 within the reagent volume 2742 to deform the reagent container 2780 from a first configuration to a second configuration (the second configuration is not shown in FIG. 5). In this manner, movement of the plunger portion 2754 can urge the frangible portion 2788 of the reagent container 2780 against the puncturer 2792 to pierce and/or rupture the frangible portion 2788. Thus, as described in more detail herein, when the puncturer 2792 pierces the reagent container 2780, the delivery pathway 2771 provides a pathway through which the contents of the reagent container 2780 can flow (e.g., when in the second configuration). The plunger portion 2754 of the actuator 2750 and a portion of the housing 2741 can collectively define a seal to fluidically and/or optically isolate the reagent volume 2742 from a volume outside of the housing 2741.

As described above, the lock member 2772 is configured to maintain at least a portion of the skirt 2781 of the reagent container 2780 in contact with the delivery portion 2770 (e.g., the shoulder 2775 of the delivery portion 2770) of the housing 2741. Moreover, the portion of the skirt 2781 and the shoulder 2775 can form a substantially fluid-tight seal, thus reducing and/or eliminating backflow of the reagent within the reagent container 2780 during use. In this manner, by maintaining the position of the skirt 2781 relative to the delivery portion 2770, the lock member 2772 can facilitate maintaining the substantially fluid-tight seal between the skirt 2781 and the shoulder 2775 of the delivery portion 2770. In addition, the lock member 2772 can limit movement of the reagent container 2780 relative to the delivery portion. In particular, the lock member 2772 can limit movement when the reagent container 2780 is deformed from a first configuration to a second configuration. In this manner, in use, the lock member 2772 can limit and/or prevent undesired movement of the reagent container 2780, thereby providing for substantial repeatable delivery of the contents from the reagent container 2780 to the reaction chamber 2732. Similarly stated, the reagent container 2780 can be held in a preferable position (e.g., stabilized) when in the first configuration and/or the second configuration.

The lock member 2772 can be any suitable size and/or shape. For example, in some embodiments, the lock member 2772 can be sized and/or shaped to correspond to (e.g., by shape, size, surface design, texture, etc.) a portion of the skirt 2781 of the reagent container 2780. In this manner, the lock member 2772 and the skirt 2781 can cooperatively function to substantially maintain the reagent container 2780 in a desired position relative to the delivery portion 2770.

Figure 6:
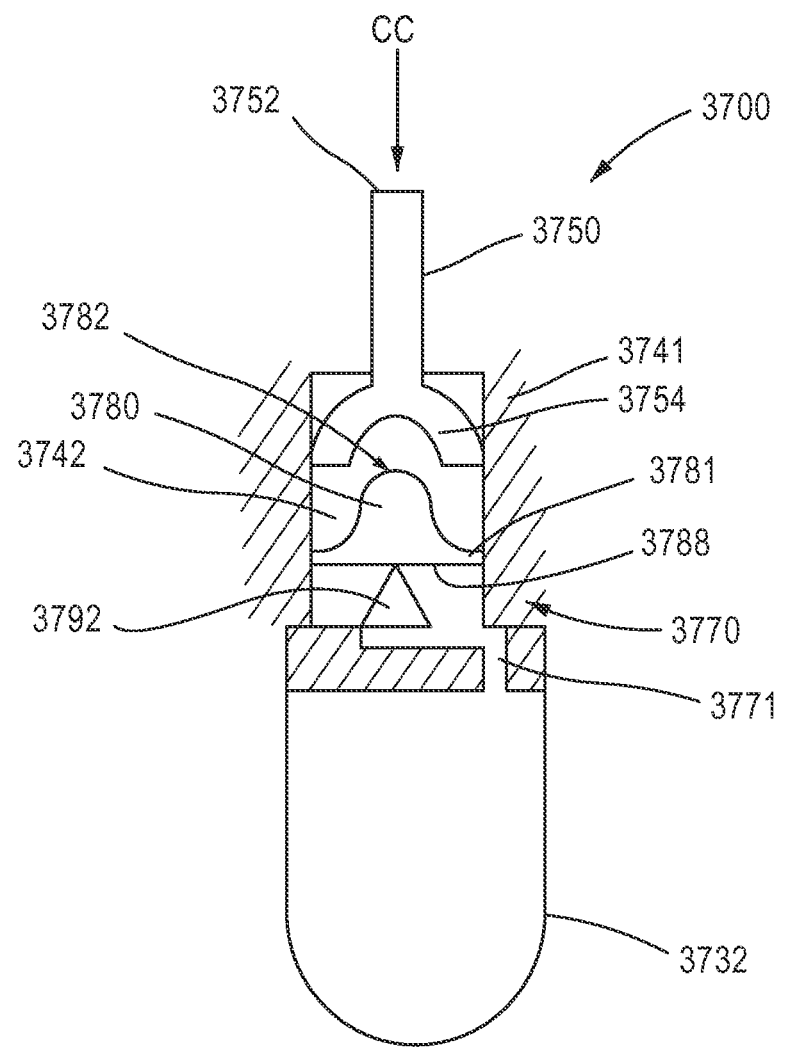
FIGS. 6 and 7 are schematic illustrations of a container assembly according to an embodiment, in a first configuration and second configuration, respectively.
Figure 7:
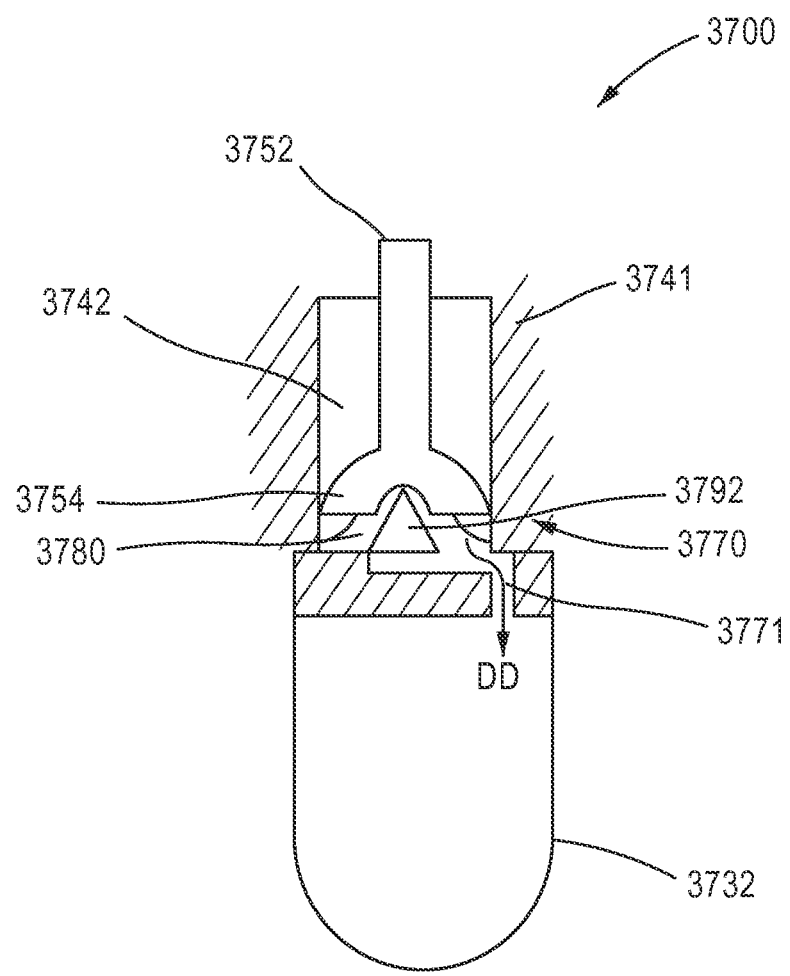

FIGS. 6 and 7 show a container assembly 3700 according to an embodiment in a first configuration (FIG. 6) and a second configuration (FIG. 7). The container assembly 3700 can be used with and manipulated by any of the instruments and/or any of the components described herein and in the '461 application, which is incorporated herein by reference in its entirety. In this manner, the container assembly 3700 and any of the container assemblies described herein can be used to detect and/or identify target cells (e.g., bacteria) within a sample according to any of the methods described herein or in the '461 application. For example, in some embodiments, the container assembly 3700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 3700 is used in methods of cell identification and/or detection that do not involve removal of contents from the container assembly 3700, separation of the contents within the container assembly 3700, washing of the contents within the container assembly 3700 and/or rinsing of the contents within the container assembly 3700.

The container assembly 3700 includes a housing 3741, a reaction chamber 3732, a reagent container 3780, and an actuator 3750. The housing 3741 is removably coupled to the reaction chamber 3732. For example, in some embodiments, the housing 3741 can be threadedly coupled to the reaction chamber 3732. In other embodiments, the housing 3741 and the reaction chamber 3732 can form an interference fit to couple the housing 3741 to the reaction chamber 3732. The housing 3741 defines a reagent volume 3742 and includes a delivery portion 3770. The delivery portion 3770 includes a puncturer 3792. In some embodiments, the housing 3741, the delivery portion 3770, and/or the puncturer 3792 can be monolithically constructed. In other embodiments, the housing 3741, the delivery portion 3770, and/or the puncturer 3792 can be formed separately and then joined together.

The delivery portion 3770 is configured to facilitate the delivery of the contents from the reagent container 3780 and/or the reagent volume 3742 into the reaction chamber 3732. Thus, as shown, the delivery portion 3770 can provide any suitable pathway and/or mechanism for delivering contents disposed in the reagent container 3780 and/or reagent volume 3742 into the reaction chamber 3732. For example, the contents of the reagent container 3780 can be transferred along (e.g., urged at least in part by gravitational force, force applied by the actuator 3750, surface tension forces or the like) one or more surfaces of the delivery portion 3770 and into the reaction chamber 3732. In particular, the delivery portion 3770 defines a delivery pathway 3771 between the reagent volume 3742 and the reaction chamber 3732. The delivery pathway 3771 can have any suitable size and/or shape, and can accommodate any desired flow rate therethrough. For example, in some embodiments, the delivery pathway 3771 can accommodate any suitable flow rate, e.g., 1 ml/sec, 2 ml/sec, 3 ml/sec, 4 ml/sec, 5 ml/sec. Moreover, the shape and/or size of the delivery pathway 3771 can be variable. Although the delivery portion 3770 is shown as including a single delivery pathway 3771, in other embodiments, a delivery portion can define any suitable number of delivery pathways.

The puncturer 3792 of the delivery portion 3770 is configured to pierce (e.g., rupture) a frangible portion 3788 of the reagent container 3780 to convey a reagent from the reagent container 3780 into the reaction chamber 3732. Thus, the puncturer 3792 can include any sharp point, sharp edge and/or series of protrusions configured to pierce the reagent container 3780. The arrangement of and/or the shape of the puncturer can limit clogging and/or obstructions that may result from the piercing, thus providing a more repeatable delivery of the contents of the reagent container 3780. The puncturer 3792 can place the reagent container 3780 in fluid communication with the delivery pathway 3771 of the delivery portion 3770. In this manner, and as described in more detail herein, the puncturer can facilitate the transfer of the contents of the reagent container 3780 to the reaction chamber 3732.

The reagent container 3780 can be completely or partially filled with any suitable reagent or substance. For example, the reagent container 3780 can contain transduction particles that include an engineered nucleic acid formulated to cause the target cell (e.g., bacteria) to produce one or more reporter molecules. In some embodiments, the reagent container 3780 can contain one or more transduction particles engineered to be incapable of replication (e.g., lytic replication, lysogenic replication). For example, in some embodiments, the reagent container 3780 can contain any of the transduction particles described herein and in U.S. Provisional Application Nos. 61/983,765, entitled "Reagent Cartridge for Detection of Cells," filed Apr. 24, 2014; 61/779,177, entitled "Non-Replicative Transduction Particles and Transduction Particle-Based Reporter Systems," filed Mar. 13, 2013; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, and International Patent Application No. PCT/US2014/026536, entitled "Non-Replicative Transduction Particles and Transduction Particle-Based Reporter Systems," filed Mar. 13, 2014, each of which is incorporated herein by reference in its entirety.

In some embodiments, the reagent container can contain a reagent formulated to react with one or more reporter molecules to enhance production of a signal. For another example, the reagent container 3780 can include a substrate, such as tridecanal, that can interact with a reporter molecule (e.g., luciferase), to produce a measurable signal, e.g., via a luminescence reaction. For yet another example, in some embodiments, the reagent container 3780 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The reagent container 3780 can be shaped and sized to be disposed substantially inside the reagent volume 3742. The reagent container 3780 can be constructed from materials that are substantially impermeable to and/or substantially chemically inert from the substance contained therein, e.g., transduction particle, substrate, antibiotics, buffers, surfactants, or any other reagent that can be used with the detection assay. At least a portion of the reagent container 3780 (e.g., the frangible portion 3788) can be constructed from a material (e.g., polymer film, such as any form of polypropylene) having certain temperature characteristics such that the desired properties and integrity are maintained over a certain temperature. For example, in some instances, it can be desirable to store the reagent container 3780 containing reagent and/or substrate in a refrigerated condition. In some embodiments, a portion of the reagent container 3780 can be constructed from bi-axially oriented polypropylene (BOP). In some embodiments, a portion of the reagent container 3780 can be constructed from aluminum. In some embodiments, a portion of the reagent container 3780 can be constructed from polyvinyl chloride (PVC), ethylene vinyl alcohol (EVOH), polyethylene (PE) and/or polychlorotrifluoroethene (PCTFE or PTFCE).

The reagent container 3780 has a skirt 3781, a contact portion 3782 and a frangible portion 3788. The skirt 3781 surrounds at least a portion of the frangible portion 3788. The skirt 3781 can be any suitable size and/or shape, and can include any suitable surface design (e.g., smooth, rough and/or the like). In some embodiments, the skirt 3781 and the delivery portion 3771 can form a substantially fluid-tight seal to minimize dead volume during use.

As described below, the contact portion 3782 of the reagent container 3780 is configured to contact the plunger portion 3754 of the actuator 3750. The contact portion can be any suitable size and/or shape. For example, in some embodiments, the contact portion 3782 can be sized and/or shaped to correspond to the actuator 3750. In other embodiments, the contact portion 3782 can include one or more stress concentration risers, perforations or the like to facilitate deformation of the contact portion 3782 and/or the reagent container 3780 in a desired manner. For example, in some embodiments, the contact portion 3782 can include geometric features and/or material properties to facilitate deformation of the reagent container 3780 in a particular direction and/or manner to minimize dead volume during use.

Figure 8:
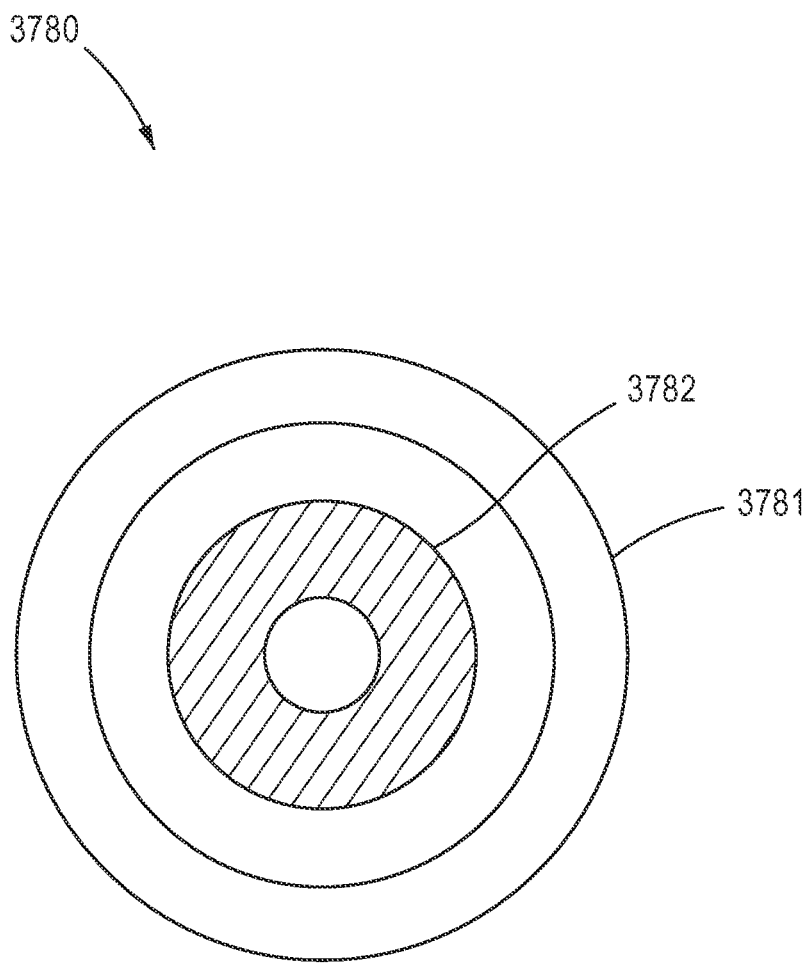
FIG. 8 is a top view of a portion of the container assembly shown in FIGS. 6 and 7.
Figure 9:
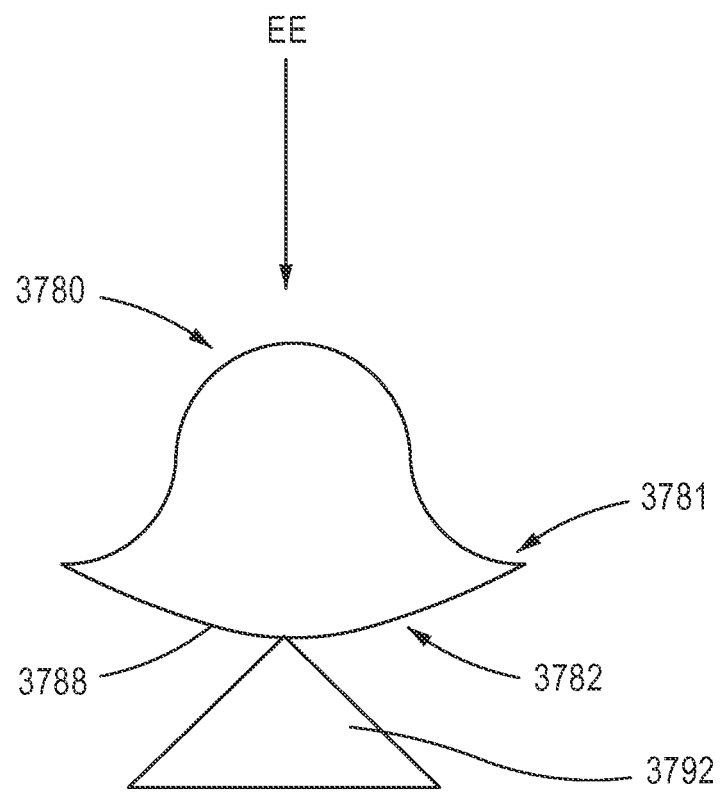
FIG. 9 is a schematic illustration of a portion of the container assembly shown in FIGS. 6 and 7 being deformed in response to an applied force.

For example, as shown in FIG. 9, in some embodiments, the contact portion 3782, the skirt 3781 and/or the frangible portion 3788 can be collectively configured such that when a force is applied to the contact portion 3782 (as shown by the arrow EE), the frangible portion 3788 will bulge outwardly to produce a convex shape. In some embodiments, the delivery portion 3770 of the housing 3741 can include a concave surface (not shown in FIGS. 6-9) that corresponds to the deformed or "bulged" shape of the frangible portion during use. In this manner, the deformed portion of the reagent container 3780 can be matingly received within the delivery portion 3770 of the housing to minimize dead volume, facilitate repeatable delivery of reagents or the like.

As shown in FIG. 8, in some embodiments, the contact portion 3782 can be an annular ring. In this manner, the contact portion 3782 can be configured to mate with the plunger portion 3754 of the actuator 3750 substantially uniformly across an area defined by the annular ring, resulting in minimization of dead volume and repeatable conveyance of the contents of the reagent container 3780 to the reaction chamber 3732. Although shown to have a constant width, in other embodiments, the annular ring can be any suitable size or shape (e.g., circular, oval, rectangular etc.). For example, in some embodiments, the annular ring can have varying dimensions (e.g., varying ring width). In this manner, the contact portion 3782 and the plunger portion 3754 can cooperatively function to suitably mate, resulting in repeatable delivery of the contents of the reagent container 3780 from the reagent container 3780.

The actuator 3750 has a plunger portion 3754 disposed within the reagent volume 3742, and an engagement portion 3752. The engagement portion 3752 of the actuator 3750 is configured to be manipulated to move the plunger portion 3754 within the reagent volume 3742 to deform the reagent container 3780 from a first configuration (FIG. 6) to a second configuration (FIG. 7). Similarly stated, the plunger portion 3754, in response to the manipulation of the engagement portion 3752 of the actuator 3750, can engage the contact portion 3782 of the reagent container 3780 to deform the reagent container 3780 from the first configuration to the second configuration. In this manner, movement of the plunger portion 3754 can urge the frangible portion 3788 of the reagent container 3780 against the puncturer 3792 to pierce and/or rupture the frangible portion 3788. Thus, as described in more detail herein, when the puncturer 3792 pierces the reagent container 3780, the delivery pathway 3771 provides a pathway through which the contents of the reagent container 3780 can flow (e.g., when in the second configuration).

In some embodiments, the plunger portion 3754 of the actuator 3750 and a portion of the housing 3741 can collectively define a seal to fluidically and/or optically isolate the reagent volume 3742 from a volume outside of the housing 3741. Moreover, the plunger portion 3754 can any suitable size and/or shape. For example, the plunger portion 3754 can be shaped and/or sized to correspond to the contact portion 3782 of the reagent container 3780 and/or to the puncturer 3792. Further to this example, as shown, the plunger portion 3754 has a curved shape configured to matingly engage with a curved shape of the contact portion 3782 of the reagent container 3780. In this manner, the plunger portion 3754, the contact portion 3782, and/or the puncturer 3792 can mate together and/or cooperatively function to limit dead volume (e.g., dead volume within the delivery portion 3770). Minimizing dead volume allows for repeatable conveyance of the contents of the reagent container 3780 to the reaction chamber 3732, and repeatable piercing of the reagent container 3780 (e.g., repeatable blister burst).

As shown in FIG. 6, the container assembly 3700 is in a first configuration. In the first configuration, the actuator 3750 is positioned such that the reagent container 3780 disposed within the housing 3741 is substantially undeformed. Similarly stated, the actuator 3750 is positioned such that it does not cause puncturer 3752 to pierce the reagent container 3780. Thus, the container assembly 3700 is in a "ready" state when in the first configuration. In some embodiments, the container assembly 3700 can include a safety mechanism (not shown) to prevent and/or limit movement of the actuator 3750 relative to the housing 3741 until desired by the operator.

To actuate the container assembly 3700, a force is applied to the engagement portion 3752 of the actuator 3750, thus causing the actuator 3750 to move as shown by the arrow CC in FIG. 6. As shown in FIG. 7, the container assembly 3700 is in a second configuration. In the second configuration, the actuator 3750 is positioned such that the reagent container 3780 is substantially deformed. Similarly stated, the actuator 3750 is positioned such that at least a portion of the force is transferred to the reagent container 3780. In such a configuration, the puncturer 3792 has pierced the reagent container 3780 (e.g., the frangible portion 3788), such that the contents of the reagent container have substantially exited the reagent container 3780 and entered the delivery portion 3770 and/or the reaction chamber 3732, as shown by the arrow DD.

In use, the actuator 3750 (e.g., the engagement portion 3752) is manipulated to move the plunger portion 3754 within the housing 3741 such that the plunger portion 3754 engages a contact portion of the reagent container 3780 to partially deform the reagent container 3780 from the first configuration to the second configuration. As the plunger portion 3754 engages the reagent container 3780, the puncturer 3792 pierces a portion of the reagent container 3780 (e.g., a frangible portion 3788) to convey a reagent from the reagent container 3780 into the reaction volume 3742, the delivery portion 3770, and/or the reaction chamber 3732. From the first configuration to the second configuration, the actuator 3750 is manipulated to move the plunger portion 3754 within the housing 3741 such that the plunger portion 3754 engages a contact portion of the reagent container 3780 to deform the reagent container 3780. As the reagent container 3780 deforms, substantially all of its contents (e.g., a reagent) is conveyed from the reagent container 3780 into the reaction volume 3742, the delivery portion 3770, and/or the reaction chamber 3732, such that "dead volume" in the reagent container 3780 is limited. In this manner, substantially repeatable delivery of the contents from the reagent container 3780 to the reaction chamber 3732 can be obtained. For example, in some embodiments, a deformation of a first reagent container at a first time and a deformation of a second reagent container at a second time after the first time can be substantially similar, thereby allowing for substantially all of the contents to be transferred from the reagent container 3780 at the first time and the second time. Moreover, this arrangement can limit clogging or obstructions that may result from the piercing of the reagent container 3780, thus providing a more repeatable delivery of the contents of the reagent container 3780.

Figure 10:
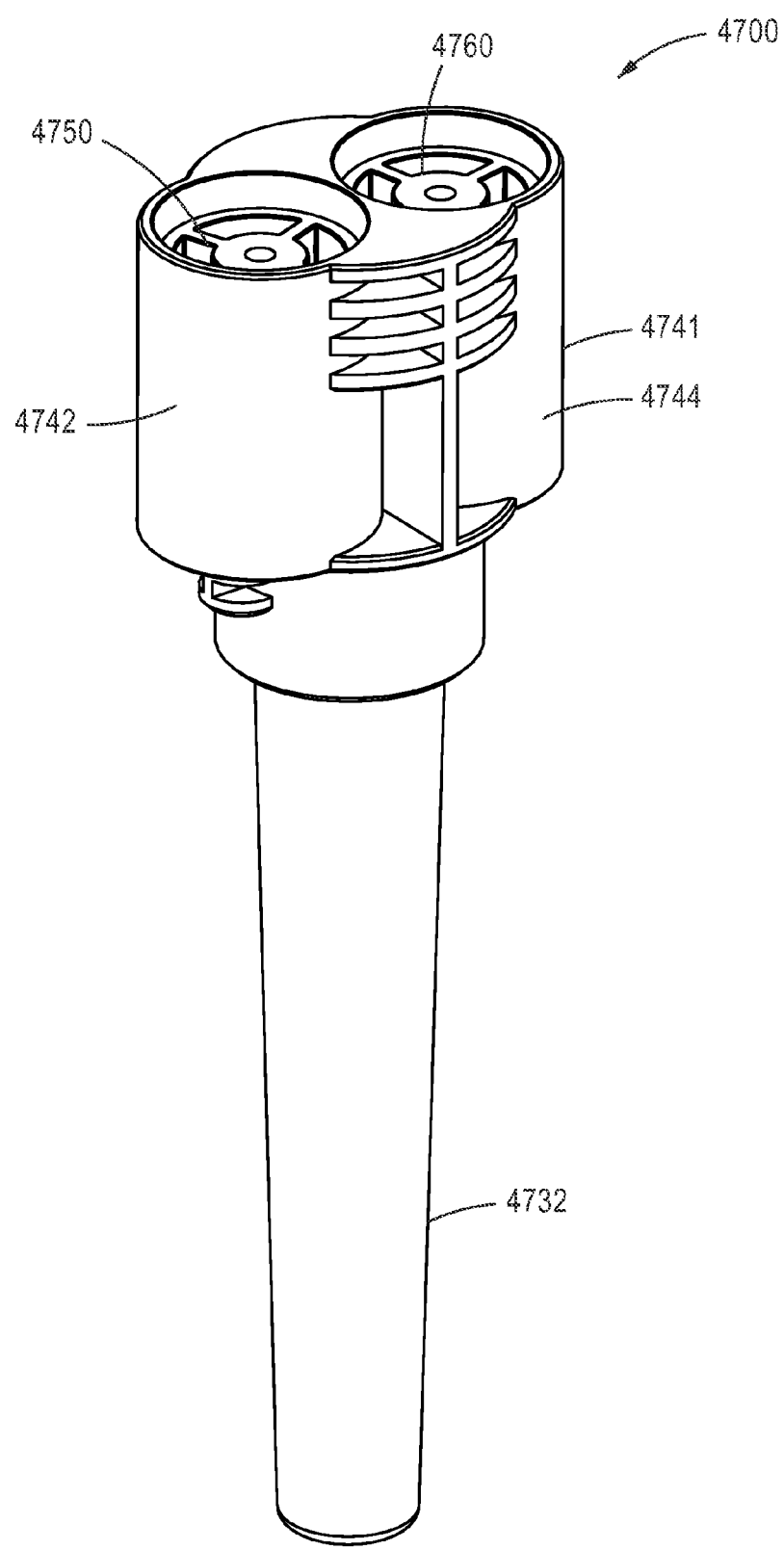
FIGS. 10 and 11 show a perspective view and an exploded view, respectively, of a container assembly 4700, according to an embodiment.
Figure 11:
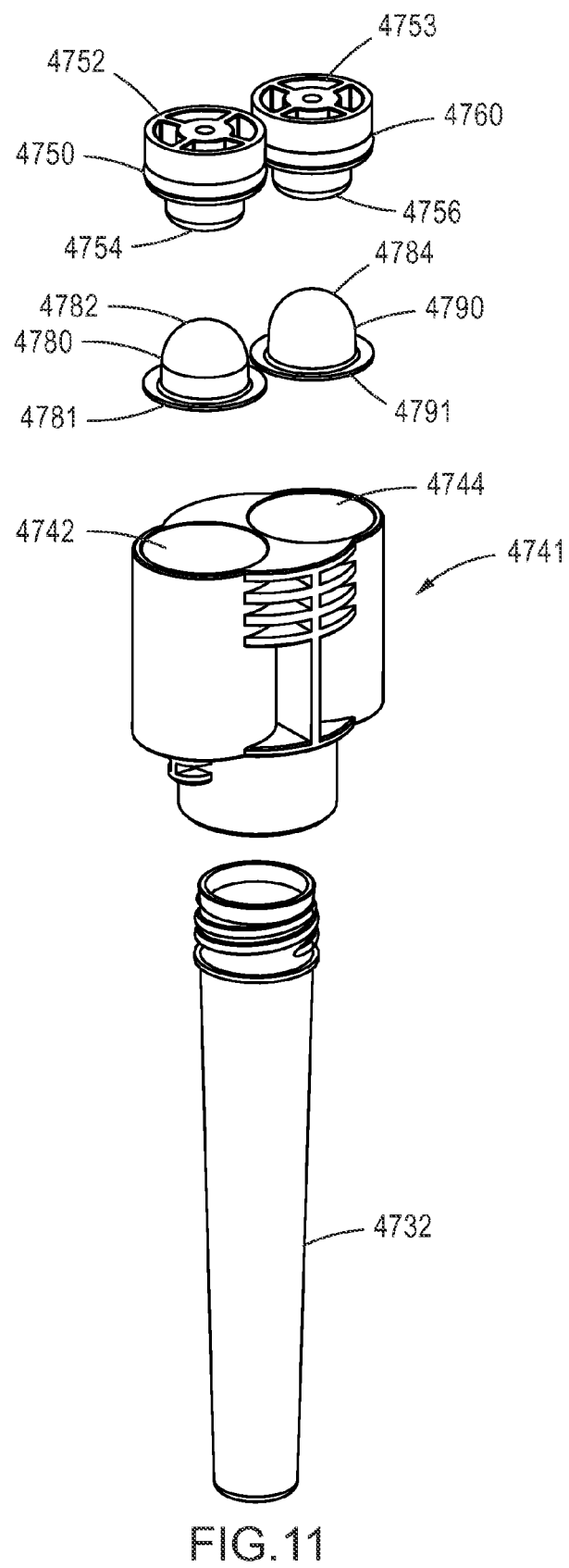

Although the container assemblies 1700, 2700 and 3700 are shown as including only one reagent container, in other embodiments, a housing and/or container assembly can include any suitable number of reagent containers. For example, FIGS. 10 and 11 show a perspective view of a container assembly 4700 and an exploded view of the container assembly 4700, respectively, according to an embodiment. The container assembly 4700 can be used with and manipulated by any of the instruments and/or any of the components described herein and in U.S. patent application Ser. No. 13/802,461, entitled "Systems and Methods for Detection of Cells using Engineered Transduction Particles," which is incorporated herein by reference in its entirety. In this manner, the container assembly 4700 and any of the container assemblies described herein can be used to detect and/or identify target cells (e.g., bacteria) within a sample according to any of the methods described herein or in the '461 application. For example, in some embodiments, the container assembly 4700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 4700 is used in methods of cell identification and/or detection that do not involve removal of contents from the container assembly 4700, separation of the contents within the container assembly 4700, washing of the contents within the container assembly 4700 and/or rinsing of the contents within the container assembly 4700.

The container assembly 4700 includes a housing 4741, a first actuator 4750, a second actuator 4760, and a reaction chamber 4732. The assembly of the housing 4741, the first actuator 4750, the first reagent container 4780, the second actuator 4760 and the second reagent container 4790 can be referred to as a "cap assembly" or "reagent assembly." The housing 4741 (and/or the cap assembly) is removably coupled to the reaction chamber 4732. For example, as shown in FIG. 10, the housing 4741 can be threadedly coupled to a proximal portion of the reaction chamber 4732. In other embodiments, the housing 4741 and the reaction chamber 4732 can form an interference fit to couple the housing 4741 to the reaction chamber 4732. Thus, the housing 4741 (or cap assembly) can be stored separately from and/or spaced apart from the reaction chamber 4732. In this manner, a user can then dispose a sample into the reaction chamber 4732 in accordance with the methods described herein (and in the '461 application, which is incorporated herein by reference in its entirety), and can then assembly the housing 4741 (or cap assembly) to the reaction chamber 4732 (or "tube") and complete the steps for cell identification, as described herein.

The housing 4741 defines a first reagent volume 4742 configured to receive a first reagent container 4780 and a second reagent volume 4744 configured to receive a second reagent container 4790. The housing 4741 includes a first puncturer 4792, a second puncturer 4794, a first delivery portion 4770, and a second delivery portion 4772. In some embodiments, the housing 4741, the first delivery portion 4770, the second delivery portion 4772, the first puncturer 4792, and/or the second puncturer 4794 can be monolithically constructed. In other embodiments, the housing 4741, the first delivery portion 4770, the second delivery portion 4772, the first puncturer 4792, and/or the second puncturer 4794 can be formed separately and then joined together.

Figure 12:
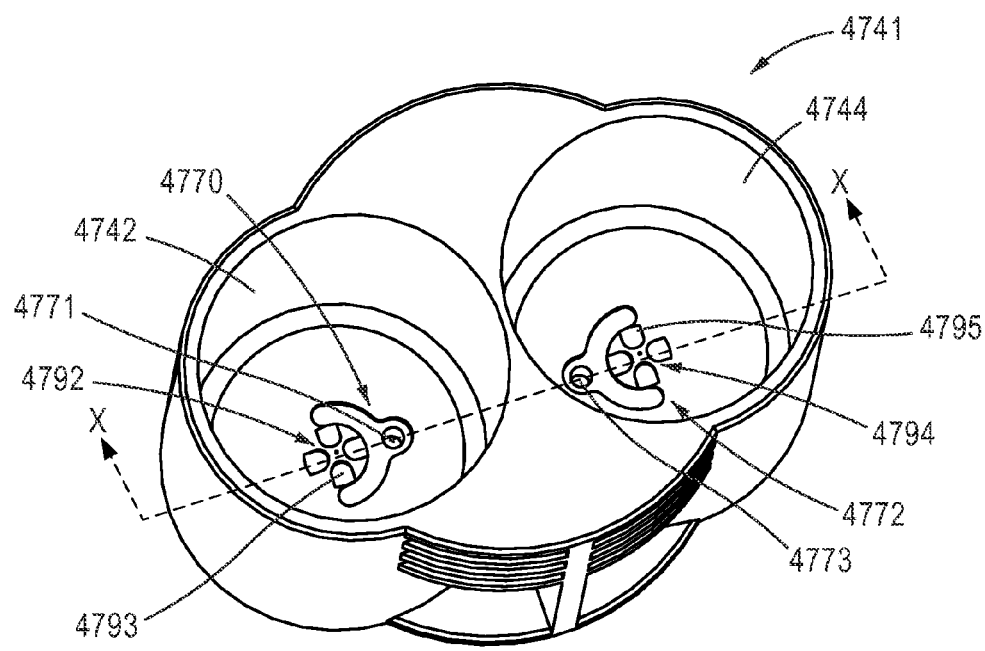
FIG. 12 is a top perspective view of a housing of the container assembly shown in FIGS. 10 and 11.
Figure 13:
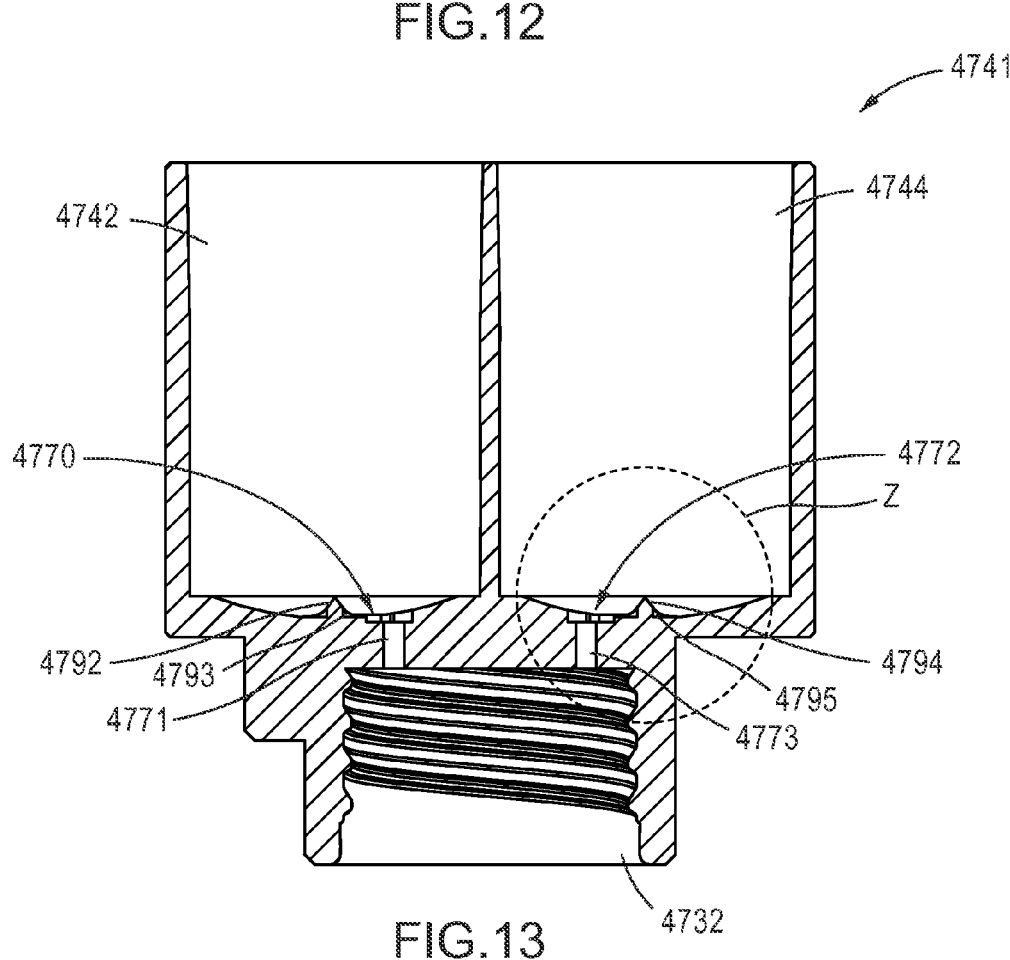
FIG. 13 is a cross-sectional view of the housing of the container assembly shown in FIGS. 10 and 11.
Figure 14:
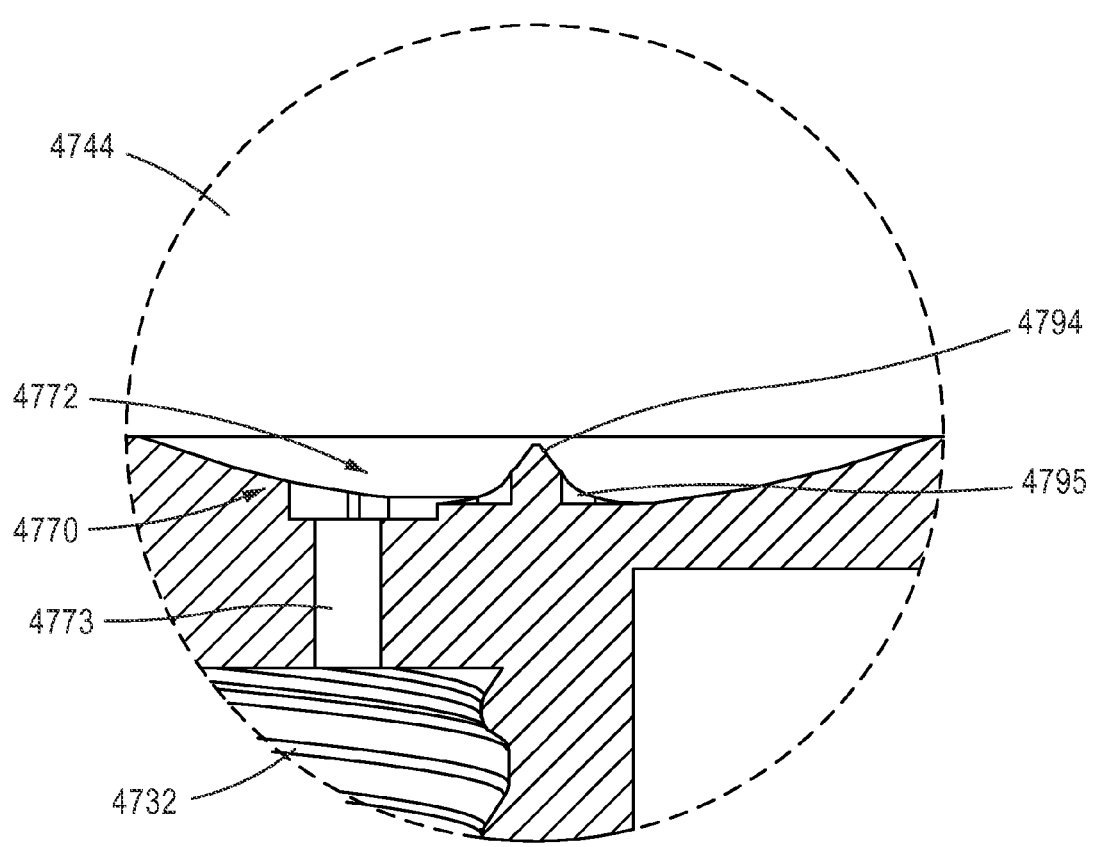
FIG. 14 is an enlarged view of the portion of the housing identified as region Z in FIG. 13.

FIGS. 12-14 show a view of an interior portion of the housing 4741, a cross-sectional side view taken along line X-X in FIG. 12, and a detailed view of the cross-sectional side view shown in FIG. 13, respectively. As shown, the housing 4741 defines a first reagent volume 4742 configured to receive the first reagent container 4780 (not shown) and a second reagent volume 4744 configured to receive the second reagent container 4790 (not shown). In addition, as shown, the first delivery portion 4770 defines a first delivery pathway 4771 in fluid communication with the first puncturer 4792. Similarly, the second delivery portion 4772 defines a second delivery pathway 4773 in fluid communication with the second puncturer 4794.

The first puncturer 4792 and/or the second puncturer 4794 are configured to pierce (e.g., rupture) the first frangible portion 4788 of the reagent container 4780 (not shown in FIG. 12) and the second frangible portion of the reagent container 4790 (not shown in FIG. 12), respectively, to convey reagent from the reagent container 4780 and/or the reagent container 4790 into the reaction chamber 4732. Thus, the puncturer 4792 and the puncturer 4794 include a sharp point, sharp edge and/or a protrusion, as shown, to pierce the reagent container 4780 and the reagent container 4790, respectively. Moreover, the first puncturer 4792 defines a first series of transfer pathways 4793 in fluid communication with the first reagent volume 4742, and the second puncturer 4794 defines a second series of transfer pathways 4795 in fluid communication with the second reagent volume 4744. In particular, each of the first series of transfer pathways 4793 and the second series of transfer pathways 4795 includes four channels spaced at approximately 90 degree intervals about the center point of the respective puncturer. Thus, as shown, the inclusion of the first series of transfer pathways 4793 and/or the second series of transfer pathways 4795 produces a discontinuous cross-sectional shape in the first puncturer 4792 and the second puncturer, respectively 4794. When the first puncturer 4792 pierces the first reagent container 4780, the first series of transfer pathways 4793 provides pathways through which the contents of the reagent container 4780 can flow. Similarly, when the second puncturer 4794 pierces the second reagent container 4790, the second series of transfer pathways 4795 provides pathways through which the contents of the reagent container 4790 can flow. Moreover, the arrangement of the first series of transfer pathways 4793, the second series of transfer pathways 4795, the cross-sectional shape of the first puncturer 4792, and/or the cross-sectional shape of the second puncturer 4794 can limit clogging or obstructions that may result from the piercing, thus providing a more repeatable delivery of the contents of the first reagent container 4780 and/or the second reagent container 4790.

As shown, the puncturer 4792 and/or the puncturer 4794 are disposed along and/or aligned with an axial centerline of the reagent volume 4742 and the reagent volume 4744, respectively. Similarly stated, the puncturer 4792 and the puncturer 4794 are centered with respect to the reagent container 4780 and the reagent container 4790, respectively. Such a configuration promotes repeatable, substantially complete delivery of the contents from the reagent container 4780 and/or the reagent container 4790, as described herein. In other embodiments, however, the puncturer 4792 and/or the puncturer 4794 can be offset from an axial centerline of the reagent volume 4742 and the reagent volume 4744, respectively. In such embodiments, for example, the offset can be based on a shape, size, slope, and/or configuration of the first delivery portion 4770, the second delivery portion 4772, and/or the reaction chamber 4732. For example, in some embodiments, the puncturer 4792 can be offset laterally towards a side portion of the housing 4741. Similarly, in some embodiments, the puncturer 4794 can be offset laterally towards a side portion of the housing 4741. In this manner, the contents of the reagent container 4780 and/or the reagent container 4790 can be encouraged to flow relatively close to the sidewall portion 4734, thus preventing splash and/or turbulence of the contents. Thus, in such embodiments, an offset of the puncturer 4792 and/or the puncturer 4794 can provide efficient, desirable and/or complete delivery of contents from the reagent container 4780 and the reagent container 4790, respectively.

Although the cross-sectional shapes of the first series of transfer pathways 4793 and the second series of transfer pathways 4795 are shown in FIG. 12 as being curved and/or semi-circular, in other embodiments, the first series of transfer pathways 4793 and/or the second series of transfer pathways 4795 can have any suitable shape and configuration, such as for example, a helical shape, a tapered shape and/or the like. Moreover, although the shape and/or size of the first series of transfer pathways 4793 and/or the second series of transfer pathways 4795 are shown in FIG. 13 as having a vertical orientation and a constant diameter (cross-sectional area, flow area), in other embodiments the first series of transfer pathways 4793 and/or the second series of transfer pathways 4795 can have any suitable orientation, configuration, and size. For example, in some embodiments, the first series of transfer pathways 4793 and/or the second series of transfer pathways 4795 can have varying cross-sectional (or flow) areas (e.g., as a function of the distance from the puncturing tip) and/or non-vertical orientations (e.g., sloped). In this manner, the first series of transfer pathways 4793 and/or the second series of transfer pathways 4795 can be configured to promote a controlled and/or desired flow rate of the substances flowing therethrough. Moreover, although the first series of transfer pathways 4793 and the second series of transfer pathways 4795 are each shown in FIG. 12 as defining four channels, in other embodiments, a transfer pathway can define any suitable number of transfer channels.

FIGS. 13 and 14 show a cross-sectional view and a close-up cross-sectional view, respectively, of the housing 4741 shown in FIG. 12. As shown, the first delivery pathway 4771 is in fluid communication with the first series of transfer pathways 4793, the first reagent volume 4742, and the reaction chamber 4732. Similarly, the second delivery pathway 4773 is in fluid communication with the second series of transfer pathways 4795, the second reagent volume 4744, and the reaction chamber 4732. As such, the first series of transfer pathways 4793 and the second series of transfer pathways 4795 are configured to place the reaction chamber 4732 in fluid communication with the first delivery pathway 4771 and the second delivery pathway 4773, respectively, and the reagent volume 4742 and the reagent volume 4744, respectively. In this manner, the contents of the reagent container 4780 can be conveyed from the reagent container 4780 to the reaction chamber 4732 via the reagent volume 4742, the first series of transfer pathways 4793, and/or the first delivery pathway 4771. Similarly, the contents of the reagent container 4790 can be conveyed from the reagent container 4790 to the reaction chamber 4732 via the reagent volume 4744, the second series of transfer pathways 4795, and/or the second delivery pathway 4773.

Moreover, although the housing 4741 is shown as having a first series of transfer pathways 4793 and a second series of transfer pathways 4795, in other embodiments, the housing 4741 can have (or define) any suitable number of transfer pathways and/or series of transfer pathways. Although not shown, in some embodiments, the first series of transfer pathways 4793 (or a portion thereof) and the second series of transfer pathways 4795 (or a portion thereof) can be in fluid communication with each other. For example, in some embodiments, the first series of transfer pathways 4793 and the second series of transfer pathways 4795 can be in fluid communication with each other via a transfer header pathway (not shown), wherein the transfer header pathway is in fluid communication with the reaction chamber 4732. In such embodiments, for example, the contents of the first reagent container 4780 can communicate (e.g., mix) with the contents of the second reagent container 4790 before reaching the reaction chamber 4732 or a portion thereof. Such an arrangement, in some embodiments, can promote mixing and/or minimize aeration, overspray and/or undesirable turbulence of the contents from the reagent container 4780 and/or the reagent container 4790.

Figure 16:
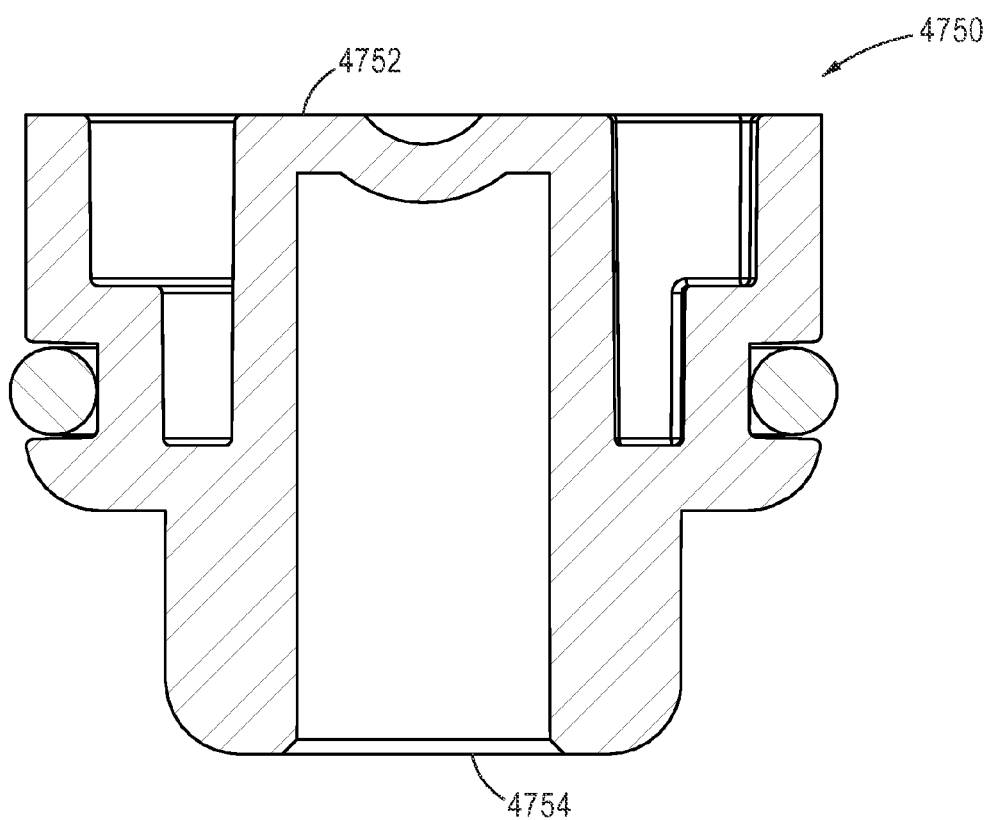
FIG. 16 is a cross-sectional view of an actuator of the container assembly shown in FIGS. 10 and 11.

Referring to FIGS. 11 and 16-18, the first actuator 4750 has a first plunger portion 4754 disposed within the first reagent volume 4742, and a first engagement portion 4752. The second actuator 4760 (not shown in FIG. 16) has a second plunger portion 4756 disposed within the second reagent volume 4744, and a second engagement portion 4753. Although the actuator shown in FIG. 16 is described herein with reference to actuator 4750 for ease of explanation, it should be understood that any feature described with reference to the first actuator 4750 can also, or alternatively, apply to the second actuator 4760, and vice-versa.

The first engagement portion 4752 of the first actuator 4750 is configured to be manipulated to move the first plunger portion 4754 within the first reagent volume 4742 to deform the first reagent container 4780. The second engagement portion 4753 of the second actuator 4760 is configured to be manipulated to move the second plunger portion 4756 within the second reagent volume 4744 to deform the second reagent container 4790. In this manner, movement of the plunger portion 4754 can urge a frangible portion 4788 of the first reagent container 4780 against the puncturer 4792 to pierce and/or rupture the frangible portion 4788. Similarly, movement of the plunger portion 4756 can urge a frangible portion 4789 of the second reagent container 4790 against the puncturer 4794 to pierce and/or rupture the frangible portion 4789. The plunger portion 4754 of the actuator 4750 and a portion of the housing 4741 can collectively define a seal to fluidically and/or optically isolate the reagent volume 4742 from a volume outside of the housing 4741. Similarly, the plunger portion 4756 of the actuator 4760 and a portion of the housing 4741 can collectively define a seal to fluidically and/or optically isolate the reagent volume 4744 from a volume outside of the housing 4741.

Moreover, although the plunger portion 4754 shown in FIG. 16 has a substantially planar surface for contacting the reagent container 4780, in other embodiments, the plunger portion 4754 can be any suitable shape, size, and/or configuration. For example, in some embodiments, the plunger portion 4754 can correspond to (e.g., share a similar shape, cooperatively function) the reagent container 4780 (e.g., the contact portion of the reagent container) and/or the puncturer 4792. For example, in some embodiments, the plunger portion 4754 can be curved (e.g., concave) so as to mate with a curved (e.g., concave) portion of the reagent container 4780. In this manner, the plunger portion 4754 and the reagent container 4780 can collectively and/or cooperatively function to limit dead volume. Moreover, such cooperation (e.g., mating) can promote repeatable delivery of the contents of the reagent container 4780. Similarly, in some embodiments, for example, the plunger portion 4754 can be curved so as to mate with a curved portion of the puncturer 4792. In this manner, the plunger portion 4754 and the puncturer 4792 can collectively and/or cooperatively function to limit dead volume. Moreover, such cooperation (e.g., mating) can promote repeatable delivery of the contents of the reagent containers 4780.

Figure 15:
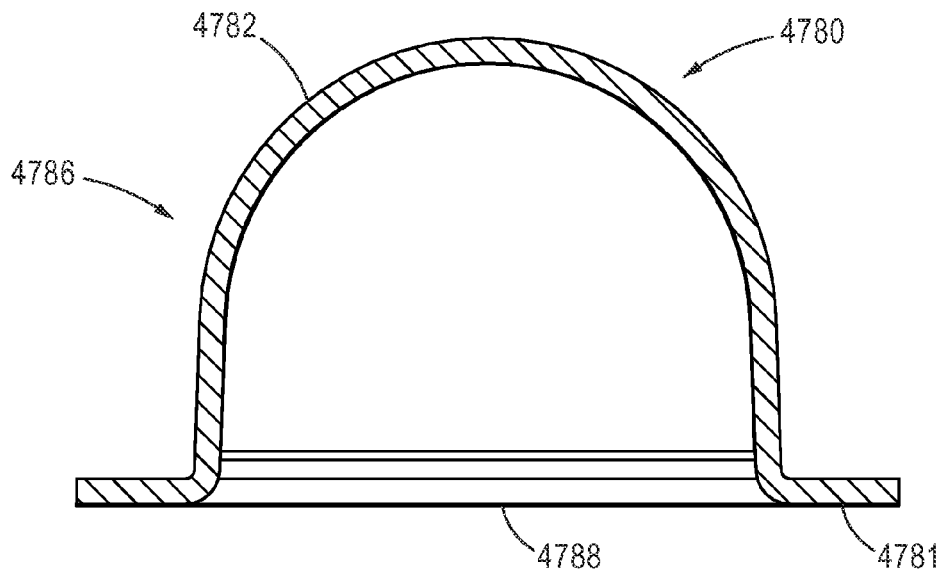
FIG. 15 is a cross-sectional view of a reagent container of the container assembly shown in FIGS. 10 and 11.

As shown in FIG. 15, the reagent container 4780 has a sidewall 4786 and a frangible portion 4788, which together define an internal volume. The internal volume can be completely or partially filled with a reagent and/or substance, as described herein. In addition, the reagent container 4780 has a skirt 4781 (referred to as a "first skirt"), a contact portion 4782 (referred to as a "first contact portion"), and a frangible portion 4788 (referred to as a "first frangible portion"). The skirt 4781 surrounds at least a portion of the frangible portion 4788. In some embodiments, the sidewall 4786 can also be frangible. The reagent container 4790 has a skirt 4791 (referred to as a "second skirt"), a contact portion 4792 (referred to as a "second contact portion"), and a frangible portion 4789 (referred to as a "second frangible portion"). The second skirt 4791 surrounds at least a portion of the second frangible portion 4789. It should be noted that although the reagent container shown in FIG. 15 is described with reference to reagent container 4780 for ease of explanation, any feature described with reference to reagent container 4780 can also, or alternatively, apply to reagent container 4790 and vice-versa.

The first skirt 4781 and/or the second skirt 4791 can be any suitable size and/or shape, and can include any suitable surface design (e.g., smooth, rough and/or the like). For example, in some embodiments, the first skirt 4781 and/or the second skirt 4791 can be sized and/or shaped to correspond to a portion of the housing 4741. The first contact portion 4782 of the reagent container 4780 and/or the second contact portion 4792 of the reagent container 4790 can be any suitable size and/or shape. For example, in some embodiments, the first contact portion 4782 and/or the second contact portion 4792 can be sized and/or shaped to correspond to the first actuator 4750 and/or the second actuator 4760, respectively. For example, in such embodiments, the first contact portion 4782 and/or the second contact portion 4792 can include a concave portion, and the first actuator 4750 and/or the second actuator 4760 can be sized and/or shaped to correspond to the concave portion of the first contact portion 4782 and/or the concave portion of the second contact portion 4792, respectively. In this manner, the reagent container 4780 and/or the reagent container 4790 can be configured to promote substantially complete dispensation of their respective contents (e.g., reagents, substances, etc.), and/or promote a preferred pathway for the contents to travel from the reagent container 4780 and/or the reagent container 4790 when the reagent container 4780 and/or the reagent container 4790 are pierced.

Figure 17:
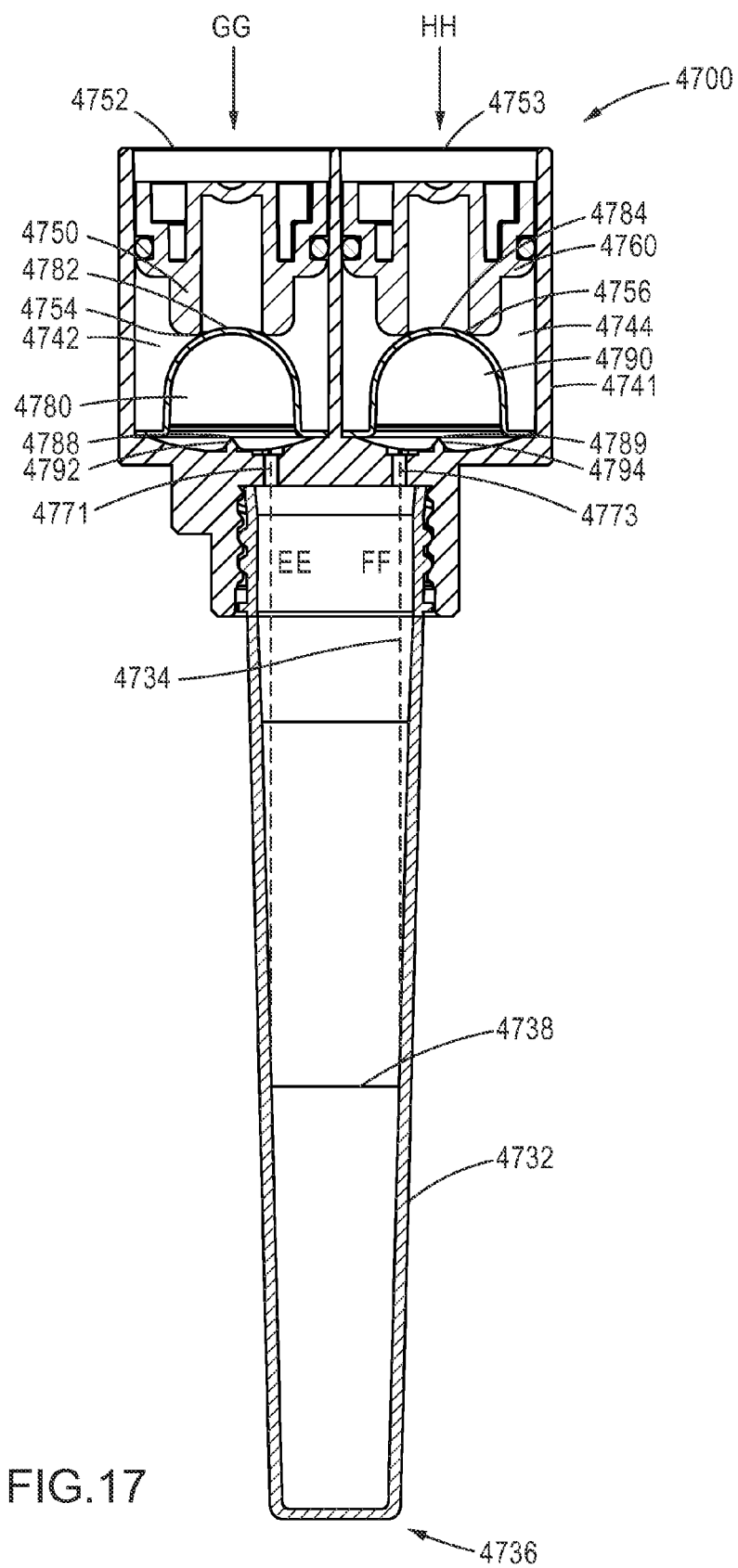
FIGS. 17 and 18 are cross-sectional views of the container assembly shown in FIGS. 10 and 11 in a first configuration and a second configuration, respectively.
Figure 18:
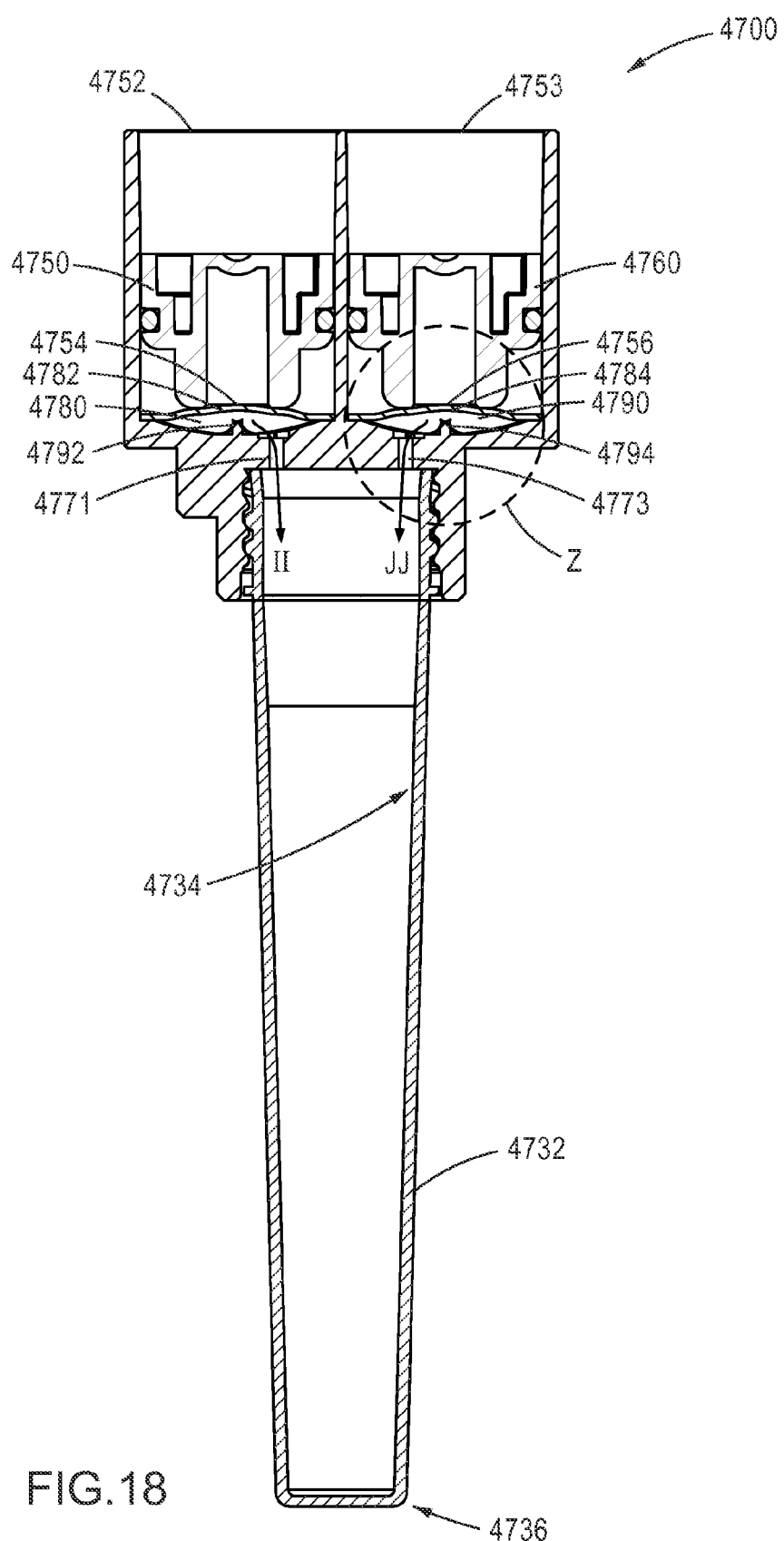

The reagent container 4780 is shaped and sized to be disposed substantially inside the first reagent volume 4742. The reagent container 4790 is shaped and sized to be disposed substantially inside the first reagent volume 4744. As best illustrated in FIGS. 17 and 18, the reagent container 4780 can be maintained in a desired position by an interference fit between the first skirt 4781 and a portion of the housing 4741. Similarly, the reagent container 4790 can be maintained in a desired position by an interference fit between the second skirt 4791 and a portion of the housing 4741. In this manner, a desired position of the reagent container 4780 and/or the reagent container 4790 can be substantially maintained relative to the housing 4741 during use.

Although the container assembly 4700 is not shown as including a lock member, in some embodiments, the container assembly 4700 can include a lock member similar to the lock member 2772 shown and described above with reference to FIG. 5. In such embodiments, the reagent container 4780 can be maintained in a desired position by the lock member (not shown) and by an interference fit between the first skirt 4781 and a portion of the housing 4741 and/or a portion of the lock member. Similarly, in such embodiments, the reagent container 4790 can be maintained in a desired position by the lock member (not shown) and by an interference fit between the second skirt 4791 and a portion of the housing 4741 and/or a portion of the lock member.

The reagent container 4780 and/or the reagent container 4790 can have any suitable size and/or volume. For example, in some embodiments, the reagent container 4780 and/or the reagent container 4790 can have an internal volume of about 400 µL when in the expanded configuration. In such embodiments, the reagent container 4780 and/or the reagent container 4790 can initially contain about 300 µL to about 350 µL (and more particularly, about 325 µL) of any of the reagents described herein. Thus, when the reagent container 4780 and/or the reagent container 4790 are in their respective expanded configurations, they have a fill percentage of about 75 percent to about 88 percent. The reagent container 4780 and/or the reagent container 4790 are configured, along with their respective plungers and portions of the housing, such that when in their respective collapsed configurations, the dispensed volume is about 250 µL to about 300 µL (and more particularly, about 285 µL). Similarly stated, when the reagent container 4780 and/or the reagent container 4790 are in their respective collapsed configurations, they have a dispensation percentage of between about 76 percent and about 92 percent.

The first reagent container 4780 and the second reagent container 4790 can be completely or partially filled with any suitable reagent or substance. In some embodiments, the first reagent container 4780 and the second reagent container 4790 can include the same contents (e.g., the same reagent). In other embodiments, the first reagent container 4780 and the second reagent container 4790 can include dissimilar contents (e.g., the first reagent container 4780 contains a first reagent and the second reagent container contains a second reagent different than the first reagent). In some embodiments, for example, the reagent container 4780 and/or the reagent container 4790 can contain transduction particles that include an engineered nucleic acid formulated to cause the target cell (e.g., bacteria) to produce one or more reporter molecules. In some embodiments, the reagent container 4780 and/or the reagent container 4790 can contain one or more transduction particles engineered to be incapable of replication (e.g., lytic replication, lysogenic replication). For example, in some embodiments, the reagent container 4780 and/or the reagent container 4790 can contain any of the transduction particles described herein and in U.S. Provisional Application Nos. 61/983,765, entitled "Reagent Cartridge for Detection of Cells," filed Apr. 24, 2014; 61/779,177, entitled "Non-Replicative Transduction Particles and Transduction Particle-Based Reporter Systems," filed Mar. 13, 2013; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, and International Patent Application No. PCT/US2014/026536, entitled "Non-Replicative Transduction Particles and Transduction Particle-Based Reporter Systems," filed Mar. 13, 2014, each of which is incorporated herein by reference in its entirety.

In some embodiments, the reagent container 4780 and/or the reagent container 4790 can contain a reagent formulated to react with one or more reporter molecules to generate and/or enhance production of a signal. For another example, the reagent container 4780 and/or the reagent container 4790 can include a luciferase substrate, such as tridecanal, that can interact with a reporter molecule (e.g., luciferase), to produce a measurable signal, e.g., via a luminescence reaction. For yet another example, in some embodiments, the reagent container 4780 and/or the reagent container 4790 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The reagent container 4780 and/or the reagent container 4790 can be constructed from any suitable materials having any suitable dimensions. The thickness of the sidewall of the reagent container 4780 and/or the reagent container 4790 can be, for example, between about 0.010 inches and 0.020 inches. Moreover, the reagent container 4780 and/or the reagent container 4790 can be constructed from materials that are substantially impermeable to and/or substantially chemically inert from the substance(s) contained therein, e.g., transduction particle, substrate, antibiotics, buffers, surfactants, or any other reagent that can be used with the detection assay. At least a portion of the reagent container 4780 (e.g., the frangible portion 4788) and/or at least a portion of the reagent container 4790 (e.g., the frangible portion 4789) can be constructed from a material (e.g., polymer film, such as any form of polypropylene) having certain temperature characteristics such that the desired properties and integrity are maintained over a certain temperature. For example, in some instances, it can be desirable to store the reagent container 4780 and/or the reagent container 4790 containing reagent and/or substrate in a refrigerated condition. In some embodiments, a portion of the reagent container 4780 and/or a portion of the reagent container 4790 can be constructed from bi-axially oriented polypropylene (BOP). In some embodiments, a portion of the reagent container 4780 and/or a portion of the reagent container 4790 can be constructed from aluminum. In some embodiments, a portion of the reagent container 4780 and/or a portion of the reagent container 4790 can be constructed from polyvinyl chloride (PVC), ethylene vinyl alcohol (EVOH), polyethylene (PE), polychlorotrifluoroethene (PCTFE or PTFCE), a pharmaceutical-grade copolymer, cyclic olefin copolymer film, Tekniflex, COC P12P, PCTFE film lamination, and/or Tekniflex VA10200.

For example, in some embodiments, the reagent container 4780 and/or the reagent container 4790 can be constructed from PVC having a laminate of polyethylene EVOH on the interior surface of the sidewalls. In this manner, the laminate can function as an oxygen barrier to preserve the reagents contained within the reagent container 4780 and/or the reagent container 4790. In some embodiments, an outer surface can include a PCTFE coating to function as a moisture barrier. In some embodiments, the frangible portion 4788 and/or the frangible portion 4789 are weld sealed to the sidewalls. Moreover, in some embodiments, the frangible portion 4788 and/or the frangible portion 4789 can be devoid of the coatings to provide sufficient "puncturability" or minimum rupture strength for repeatable operation. In other embodiments, the frangible portion 4788 and/or the frangible portion 4789 can include a lacquer coating.

The reaction chamber 4732 can be removably coupled to the housing 4741. As shown, the reaction chamber 4732 is threadedly coupled to the housing 4741. In other embodiments, however, the reaction chamber 4732 can form an interference fit to couple the reaction chamber 4732 to the housing 4741. The reaction chamber 4732 includes a sidewall portion 4734 and a distal portion (including a bottom surface) 4736, and can be any suitable chamber for containing a clinical sample (e.g., a patient sample) in a manner that permits the monitoring, identification, and/or detection of a target cell (e.g., bacteria) within the sample. In some embodiments, at least a portion of the reaction chamber 4732, such as the distal portion 4736, can be substantially transparent, for example, to allow viewing, and/or optical monitoring of the contents contained therein. In some embodiments, a portion of the reaction chamber 4732 (e.g., a distal portion) can be substantially transparent while the remainder of the reaction chamber 4732 can be substantially opaque. In this manner, the reaction chamber 4732 can be configured to convey light through the substantially transparent portion of the reaction chamber 4732, but block light at the substantially opaque portion of the reaction chamber 4732. In some embodiments, the sidewall portion 4734 of the reaction chamber 4732 can include a coating to allow for optimal transmission of light through the distal portion 4736 of the reaction chamber 4732. In some embodiments, the coating can be any suitable material configured to block and/or reflect light, for example, a label. In particular, in some embodiments, the label can be a white label to reflect light. Moreover, in some embodiments, the distal portion 4736 of the reaction chamber 4732 can be polished to promote optimal transmission of light therethrough.

FIGS. 17 and 18 show a cross-sectional side view of container assembly 4700 in a first configuration (FIG. 17) and a second configuration (FIG. 18), respectively. As shown, the distal portion 4736 of the reaction chamber 4732 includes a substantially flat bottom surface. The flat bottom surface promotes substantially uniform delivery of light therethrough. Specifically, in use, light can be transmitted through the distal portion 4736 substantially uniformly to a detector. Similarly stated, this arrangement allows a "bottom read" of the container assembly 4732 by the detector (e.g., any detector described herein and in the '461 application). Moreover, in use, such a substantially flat surface at the distal portion 4736 can result in the container assembly 4700 being placed consistently closer to and/or in contact with an optical detection window in an instrument. In this manner, such a configuration can minimize the distance in the signal path between signal production and signal detection and/or minimize an interface between mismatched dialectic mediums in the signal path, both of which can contribute to loss in signal reaching the sensor, e.g., due to light scattering and/or light refraction. Moreover, in some embodiments, for example, the flat surface can be configured to contact the optical detection window. Furthermore, as shown in FIGS. 17 and 18, the sidewall portion 4734 of reaction chamber 4732 is tapered. Similarly stated, a surface of the sidewall portion 4734 is nonparallel to a longitudinal centerline defined by the reaction chamber 4732. The tapered configuration promotes flow of contents from the reagent container 4780 and/or the reagent container 4790 along the sidewall portion 4734. As such, turbulence, splash, the production of bubbles, aeration, and/or the like, of the contents can be limited, and subsequent optical readings can be more accurate than if the sample contains such bubbles, aeration or the like. In particular, an exit portion of the first delivery pathway 4771 and an exit portion of the second delivery pathway 4773 each define an exit axis (the axis EE and the axis FF, respectively) that intersects the sidewall portion 4734 of the reaction chamber 4732, as shown in FIG. 17. Thus, in use, contents from the reagent container 4780 and/or the reagent container 4790 can flow from the first delivery pathway 4771 and/or the second delivery pathway 4773, respectively, to the sidewall portion 4734 along their respective exit axis. Moreover, as shown, the intersection of each exit axis (i.e., axis EE and axis FF) and the sidewall portion 4734 occurs above the expected fill line 4738 (or nominal fill line), thus preventing and/or limiting splashing, turbulence or the like, of the contents as the contents move from the reagent container 4780 and/or the reagent container 4790 to the reaction chamber 4732. Although the sidewall portion 4734 of reaction chamber 4732 is shown as tapered such that each exit axis intercepts the sidewall portion 4734 at a top-half portion of the reaction chamber 4732, in other embodiments, the sidewall portion 4734 can be tapered (or angled) at any suitable degree. In some embodiments, the sidewall portion 4734 can be tapered (with respect to the longitudinal centerline) by about one degree. In other embodiments, the sidewall portion 4734 can be tapered (with respect to the longitudinal centerline) by less than 5 degrees. Similarly, although the nominal fill line 4738 is illustrated to be located near a middle portion of the reaction chamber 4736, in other embodiments, the nominal fill line can be located at any suitable level (e.g., as a function an angle associated with the sidewall portion 4734 and/or either exit axis).

The reaction chamber 4732 can be constructed from any suitable material, for example, glass, plastic (e.g., polypropylene), acrylic, etc. In some embodiments, the reaction chamber 4732 can be gamma sterilizable. In some embodiments, the reaction chamber 4732 can be a commercially available container, for example a centrifuge tube, an Eppendorf® tube, a glass vial, flat-bottomed vial/tube, round bottomed vial/tube, or any other suitable container.

As shown in FIG. 17, the container assembly 4700 is in a first configuration. In the first configuration, the first actuator 4750 and the second actuator 4760 are positioned such that the reagent container 4780 and the reagent container 4790 disposed within the housing 4741 are substantially undeformed. Similarly stated, the first actuator 4750 and the second actuator 4760 are positioned such that they do not cause puncturer 4752 and puncturer 4794 to pierce the reagent container 4780 and the reagent container 4790, respectively. Thus, the container assembly 4700 is in a "ready" state when in the first configuration. In some embodiments, the container assembly 4700 can include a safety mechanism (not shown) to prevent and/or limit movement of the first actuator 4750 and/or the second actuator 4760 relative to the housing 4741 until desired by the operator.

To actuate the container assembly 4700, a force is applied to the engagement portion 4752 of the first actuator 4750, and a force is applied to the engagement portion 4753 of the actuator 4760, thus causing the first actuator 4750 and the second actuator 4760 to move as shown by the arrow GG and HH, respectively, in FIG. 17. The forces can be applied by any suitable instrument, such as those shown and described in the '461 application. The forces can be applied substantially simultaneously or at different times, in accordance with the desired assay.

More particularly, the first actuator 4750 is manipulated (e.g., at the first engagement portion 4752) to move the first plunger portion 4754 within the housing 4741 such that the first plunger portion 4754 engages the contact portion 4782 of the reagent container 4780 to partially deform the reagent container 4780 from the first configuration to the second configuration. As the first plunger portion 4754 engages the reagent container 4780, the first puncturer 4792 pierces a portion of the reagent container 4780 (e.g., the frangible portion 4788) to convey reagent from the reagent container 4780 into the first reagent volume 4742, the first delivery portion 4770, and/or the reaction chamber 4732. Similarly, the second actuator 4760 is manipulated (e.g., at the second engagement portion 4753) to move the second plunger portion 4756 within the housing 4741 such that the second plunger portion 4756 engages the second contact portion 4784 of the reagent container 4790 to partially deform the reagent container 4790 from the first configuration to the second configuration. As the second plunger portion 4756 engages the reagent container 4790, the second puncturer 4794 pierces a portion of the reagent container 4790 (e.g., the frangible portion 4789) to convey reagent from the reagent container 4790 into the second reagent volume 4744, the second delivery portion 4772, and/or the reaction chamber 4732.

Figure 19:
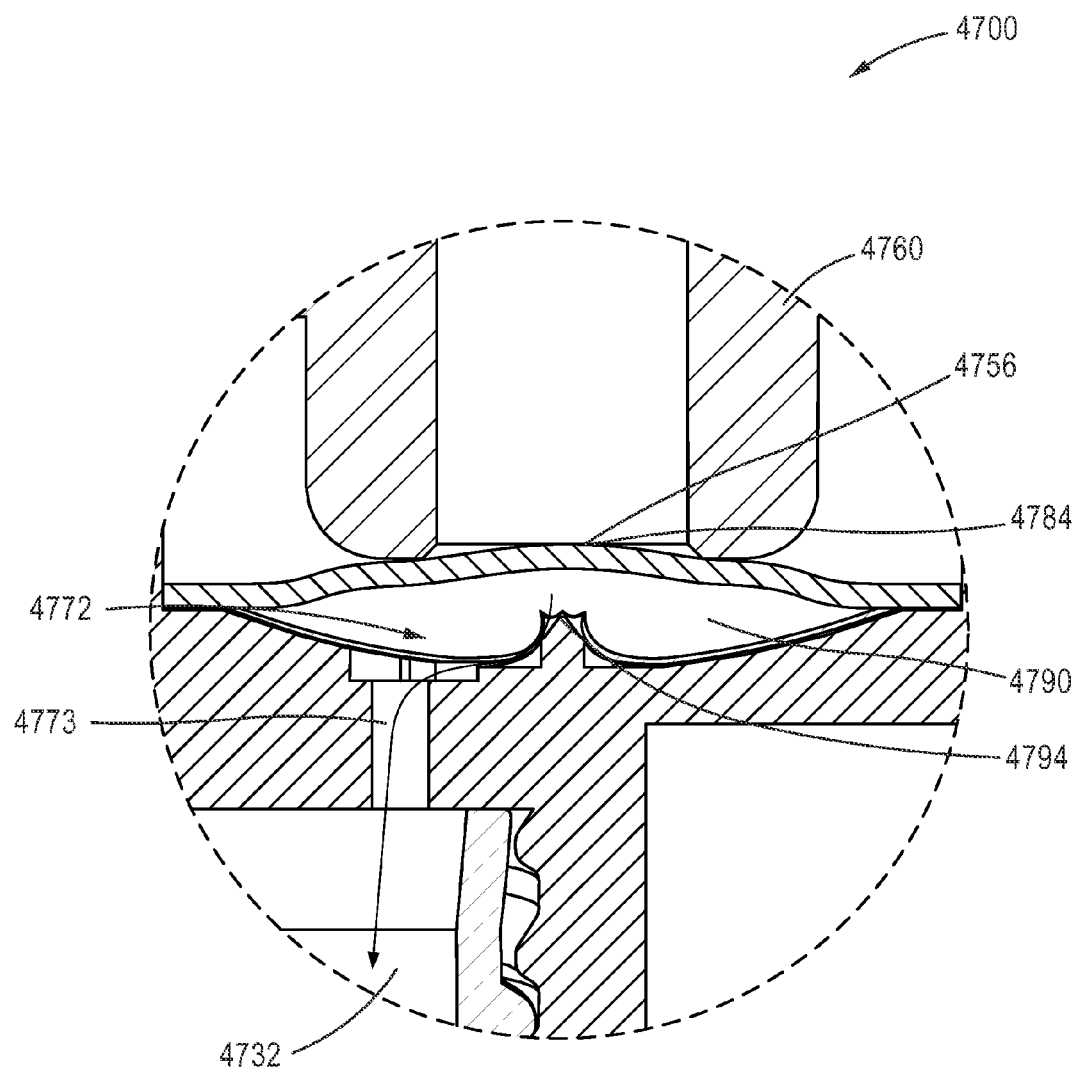
FIG. 19 is an enlarged view of the portion of the container assembly identified as region Z in FIG. 18.

As shown in FIG. 18, and in greater detail in FIG. 19, the container assembly 4700 is in a second configuration. In the second configuration, the first actuator 4750 and the second actuator 4760 are positioned such that the reagent container 4780 and the reagent container 4790 are substantially deformed and/or collapsed. Similarly stated, the first actuator 4750 and the second actuator 4760 are positioned such that at least portions of the respective forces are transferred to the first reagent container 4780 and the second reagent container 4790, respectively. In such a configuration, as shown, the first puncturer 4792 has pierced the reagent container 4780 such that a desired amount of the contents of the reagent container 4780 have substantially exited the reagent container 4780, and entered the first delivery portion 4770 and/or the reaction chamber 4732, as shown by the arrow II. Similarly, the second puncturer 4794 has pierced the reagent container 4790 such that a desired amount of the contents of the reagent container 4790 have substantially exited the reagent container 4790, and entered the second delivery portion 4772 and/or the reaction chamber 4732, as shown by the arrow JJ.

When the reagent container 4780 and/or the reagent container 4790 are deformed, a desired amount of its contents are conveyed into the reaction chamber 4732 in a manner such that "dead volume" is limited and/or substantially eliminated. As used herein the "dead volume" is the volume of reagent that is dispensed from the reagent container 4780 and/or the reagent container 4790 but that is not conveyed into reaction chamber 4732. The dead volume can include, for example, the volume of the delivery pathways and the transfer pathways. In some embodiments, the reagent container 4780 and/or the reagent container 4790 can be configured to limit the dead volume therein when the assembly 4700 is actuated. For example, in some embodiments, the contact portion 4782 and/or the contact portion 4784 can be configured, along with the corresponding engagement portions of the actuator 4750 and actuator 4760, respectively, to deform in a controlled manner that reduces the dead volume. In this manner, the reagent container 4780 and/or the reagent container 4790 can be configured to promote a consistent and/or repeatable dispensation of their contents (e.g., reagents)

In some embodiments, the cap assembly (i.e., the reagent container 4780 and/or the reagent container 4790 along with their respective plungers and portions of the housing) is configured such that the "dead volume" is between about 30 µL and about 50 µL. In some embodiments, the cap assembly is configured such that the "dead volume" about 40 µL±9 µL. By limiting the part-to-part variation in the dead volume, the accuracy of reagent delivery, and thus, the accuracy of the assay, can be improved. In some embodiments, for example, the cap assembly is configured such that the dispensed volume is about 285 µL with a coefficient of variation of about three percent.

As described herein, in some embodiments, a container assembly (e.g., container assembly 4700 or any other container assembly described herein) can contain a patient sample that potentially contains a cell (e.g., a bacteria) to be detected using the methods, instruments and/or any of the components described herein and in the '461 application, which is incorporated herein by reference in its entirety. The sample can be a human sample (e.g., a nasal swab, mucosal swab, saliva sample, blood sample, urine sample, fecal sample, tissue biopsy, bone marrow and/or cerebrospinal fluid), veterinary sample, food sample, plant sample, and/or environmental sample. In some embodiments, the sample can be a crude, raw, or otherwise substantially unprocessed sample.

Figure 20:
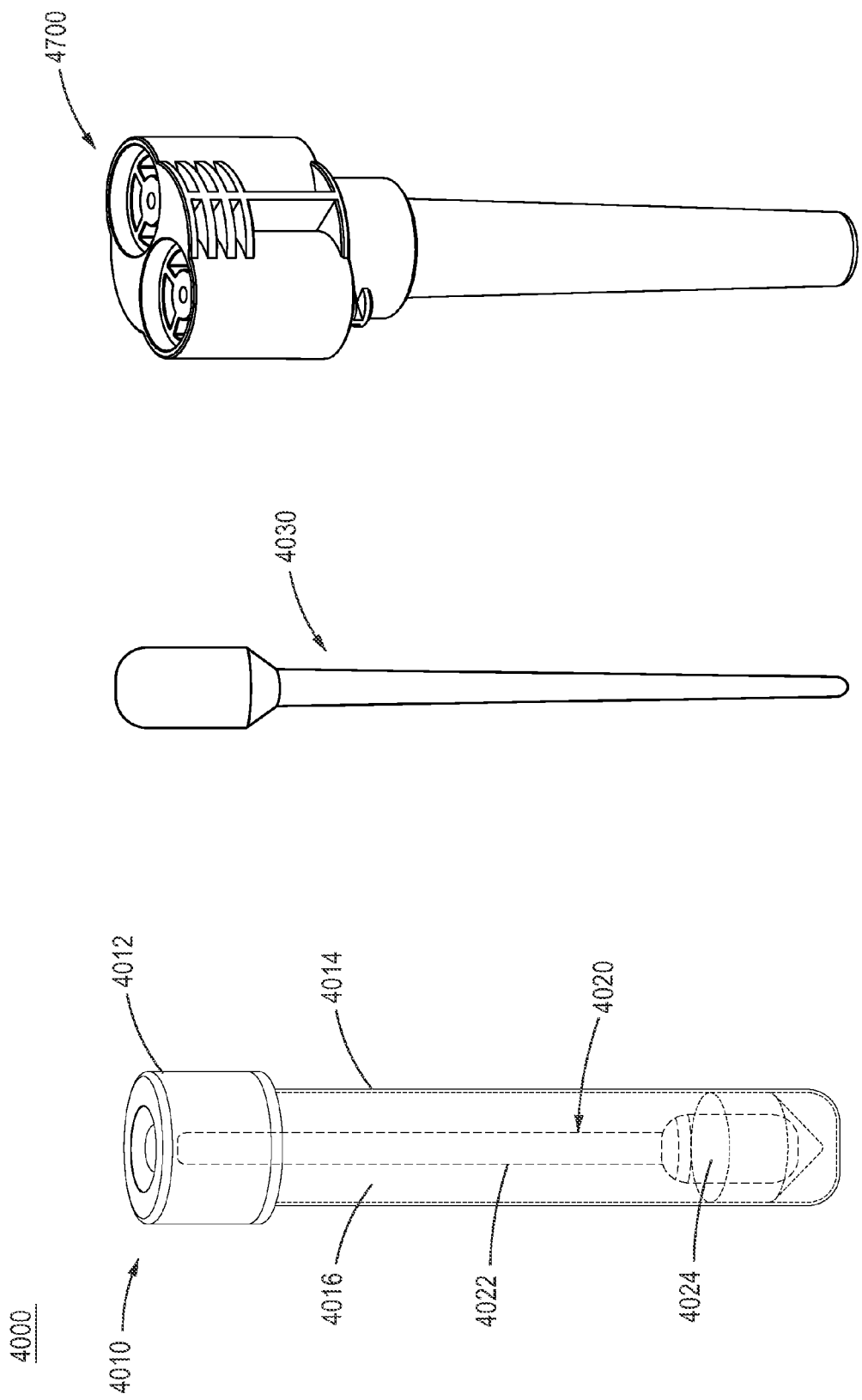
FIG. 20 is a kit, according to an embodiment, that includes the container assembly shown in FIGS. 10 and 11.

In some embodiments, a kit can be provided and/or used to perform such methods. For example, FIG. 20 illustrates a kit 4000, according to an embodiment. As shown, the kit 4000 includes a transport container assembly 4010, a transfer member 4030, and the container assembly 4700. Although shown as including the container assembly 4700, in other embodiments, a kit can include any of the container assemblies and/or cap assemblies as shown and described herein.

The transport container assembly 4010 (also referred to as the "collection assembly") includes a sample collector 4020, a transport cap 4012 and a transport chamber 4014. The transport cap 4012 is removably coupleable to the transport chamber 4014 to form a substantially fluid-tight seal. For example, in some embodiments, the transport cap 4012 can be threadedly coupled to the transport chamber 4014. In other embodiments, the transport cap 4012 and the transport chamber 4014 can form an interference fit, press fit, snap fit, and/or any other suitable fit to couple the transport cap 4012 to the transport chamber 4014.

The transport chamber 4014 can be any suitable size and/or shape, and can be constructed from any suitable material. The transport chamber 4014 defines a transport volume 4016 within which the sample can be disposed. In some embodiments, the transport chamber 4014 can include within the transport volume 4016 a transport media, solution and/or reagent (not identified in FIG. 20). The transport media can include, for example, a bacterial nutrient media, organism selective media, buffers, surfactants or any other component to facilitate growth and/or optimize the health of the patient sample (e.g., target bacteria), production of reporter molecules within the target bacteria, detection of bacteria and/or the like. In some embodiments, the transport media can include, for example, a bacterial nutrient and/or growth media (e.g., undefined medium, defined medium, differential medium, minimal media, selective media, etc.) to enable bacteria to grow and multiply, a buffer to maintain pH (e.g., Amies, PBS, HEPES, TRIS, TAPSO, Bicine, MES, MOPS, Tricine, PIPES, SSC, succinic acid, etc.) and/or a surfactant (e.g., Tween 20, Tween 80, TritonX, X-114, CHAPS, DOC, NP-40 CTAB, SDS, etc.). In some embodiments, the transport media or transport composition can be predisposed in the internal volume 4016 or it can be added after the sample is conveyed into the container. In some embodiments, the transport media can be predisposed in the transport chamber 4014, but can be selectively maintained in isolation from the sample, e.g., in a separate compartment (not shown) within the transport chamber 4014. For example, in some embodiments, the transport media can be stored in the transport cap 4012 such that the solution can be communicated to the patient sample on demand and/or in a closed-system environment.

In some embodiments, the transport media, reagent and/or composition can be tailored to enhance growth, shorten lag phase, sustain, and/or attack a particular target cell, e.g., bacterium. In some embodiments, specific versions of the solution can be employed for specific target cells and/or samples. For example, a first preparation of the solution can be tailored for nasal swab samples containing MRSA, a second preparation of the solution can be tailored for urine samples containing *E. coli*, a third preparation of the solution can be tailored for stool samples containing *C. difficile*, and the like.

The sample collector 4020 includes a shaft portion 4022 and a collection portion 4024. The shaft portion 4022 is configured to be coupled (e.g., removably or substantially permanently) to the transport cap 4012. For example, in some embodiments, the shaft portion 4022 of the sample collector 4020 can be removably coupled to the transport cap 4012 after the sample collector 4020 has been used to collect a patient sample. In other embodiments, for example, the shaft portion 4022 can remain coupled to the transport cap 4012 while the sample collector 4020 is used to collect a patient sample. In this manner, in some embodiments, a user can handle the sample collector using the transport cap, while in other embodiments, a user can handle the sample collector using the shaft portion 4022.

The sample collector 4020 can have any suitable configuration and material for collecting a patient sample. For example, in some embodiments, the sample collector 4020 can be a swab (e.g., a wound swab, a flock swab, a foam swab, etc.). Moreover, in some embodiments, the sample collector 4020 (and more specifically, the collection portion 4024) can be configured to release at least a portion of the patient sample into the transport media. In this manner, the sample collector 4020 can release a patient sample into the transport chamber 4014 for later transfer into the container assembly 4700, as described herein.

Accordingly, in some embodiments, the sample collector 4020 is configured to and/or constructed from materials formulated to maximize the sample collection efficiency and the efficiency of releasing the collected sample into the container assembly 4700 and/or reaction chamber 4732. As supported by the examples provided herein, in some situations, it has been determined that foam swabs perform better than wound and/or flocked swabs in a MRSA screen assay when the swab is transported in an assay media (e.g., via a transport chamber 4014, with an assay bead and cap 4012). In yet other instances, it has been determined that foam and/or flocked swabs perform relatively similarly, and both better than wound swabs, when the swab is transported along with the sample within the transport chamber 4014. In some instances, it has been determined that wound swabs (e.g., wound Rayon swabs) and/or Dacron swabs, although traditionally used in various sampling methods, are poor at releasing the patient sample (e.g., bacteria) into an assay. In other instances, it has been determined that flocked swabs perform better than traditional swabs (e.g., wound swabs) at releasing the patient sample but, in some instances, perform poorly in the assay. Such a poor performance, in some instances, can be mitigated by performing certain transport methods. Such transport methods can include transferring the patient sample from the patient swab to a reaction chamber (e.g., the reaction chamber 4732) without placing the patient swap in the transport chamber 4014 (e.g., transfer the patient sample via a transfer tool). In this manner, in some instances, it has been determined that flocked swabs can perform well in the assay. In further instances, it has been determined that foam swabs, while not typically used in bacterial assays, release the bacteria as well as flocked swabs and perform well in the assay.

The transfer tool 4030 can be any suitable tool used to transfer the transport media and/or sample from the transport chamber 4014 to a reaction chamber (e.g., reaction chamber 4732). For example, in some embodiments, the transfer tool 4030 can be a pipette. In other embodiments, for example, the transfer tool 4030 can be a swab. In yet further embodiments, for example, the transfer tool 4030 can be a syringe. The transfer tool 4030 can be any suitable size and shape, and can be constructed from any suitable material.

Figure 21:
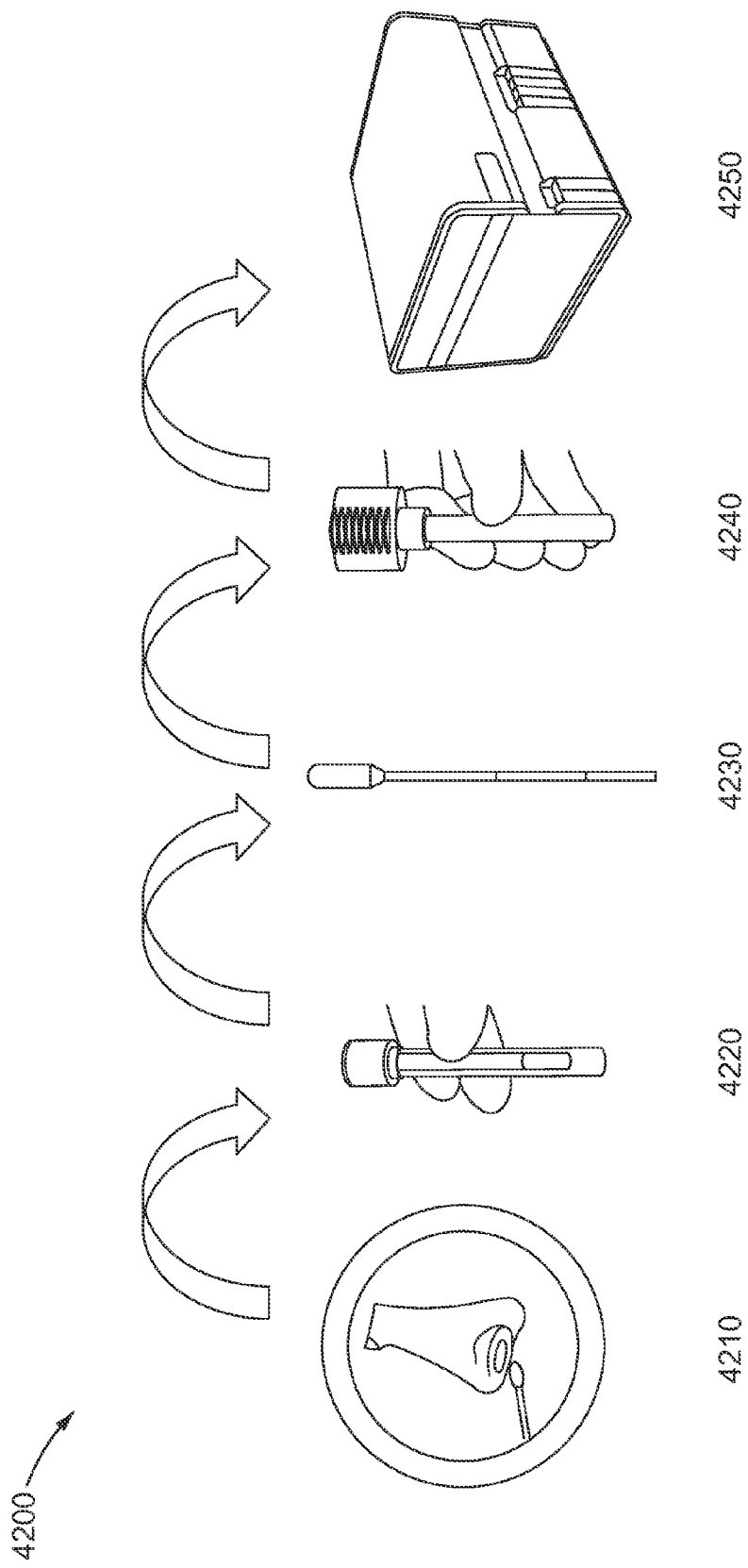
FIG. 21 is a schematic flow diagram of a method according to an embodiment.

FIG. 21 is a flow diagram illustrating a method 4200 for collecting, transporting, and testing a patient sample using the kit 4000 or any other devices shown and described herein. As shown at 4210, a patient sample is collected from a patient (e.g., via a nostril of the patient) using sample collector 4020. At 4220, the sample collector 4020 is placed into transport container assembly 4010 such that the patient sample is disposed within the transport volume 4016 of the transport chamber 4014. In particular, the sample collector 4020 is deposed within the transport volume 4016 such that the collection portion 4024 is disposed within any transport media within the transport chamber 4014. The transport cap 4012 is then coupled to the transport chamber 401, leaving the sample collector 4020 within the transport chamber 4014. In this manner, the patient sample can be communicated from the sample collector 4020 (e.g., from the collection portion 2024) to the transport volume 4016 and/or the transport media of the transport chamber 4014. In some embodiments, operations 4210 and 4220 can occur at a point of collection, such as, for example, a nurse station.

At 4230, at least a portion of the patient sample (e.g., that potentially includes the target bacteria) and the transport media can be communicated from the transport container assembly 4010 and/or the sample collector 4020 via transfer tool 4030 (e.g., a pipette) into the reaction chamber (e.g., the chamber 4732). In some instances, the transport cap 4012 is first separated from the transport chamber 4014. As such, the transfer tool 4030 can access a least a portion of the patient sample disposed within the transport chamber 4014. In this manner, a target bacterium is transferred from via transfer tool 4030 into the reaction chamber 4732 of container assembly 4700. Although shown as container assembly 4700, any suitable container assembly can be used (e.g., container assembly 1700, 2700, 3700, etc.).

At 4250, the container assembly 4700 containing target cells is disposed within a detection instrument (e.g., any instrument described herein and in the '461 application, which is incorporated herein by reference in its entirety). The container assembly 4700 is then subjected to the methods of detection described herein and in the '461 application.

Figure 22:
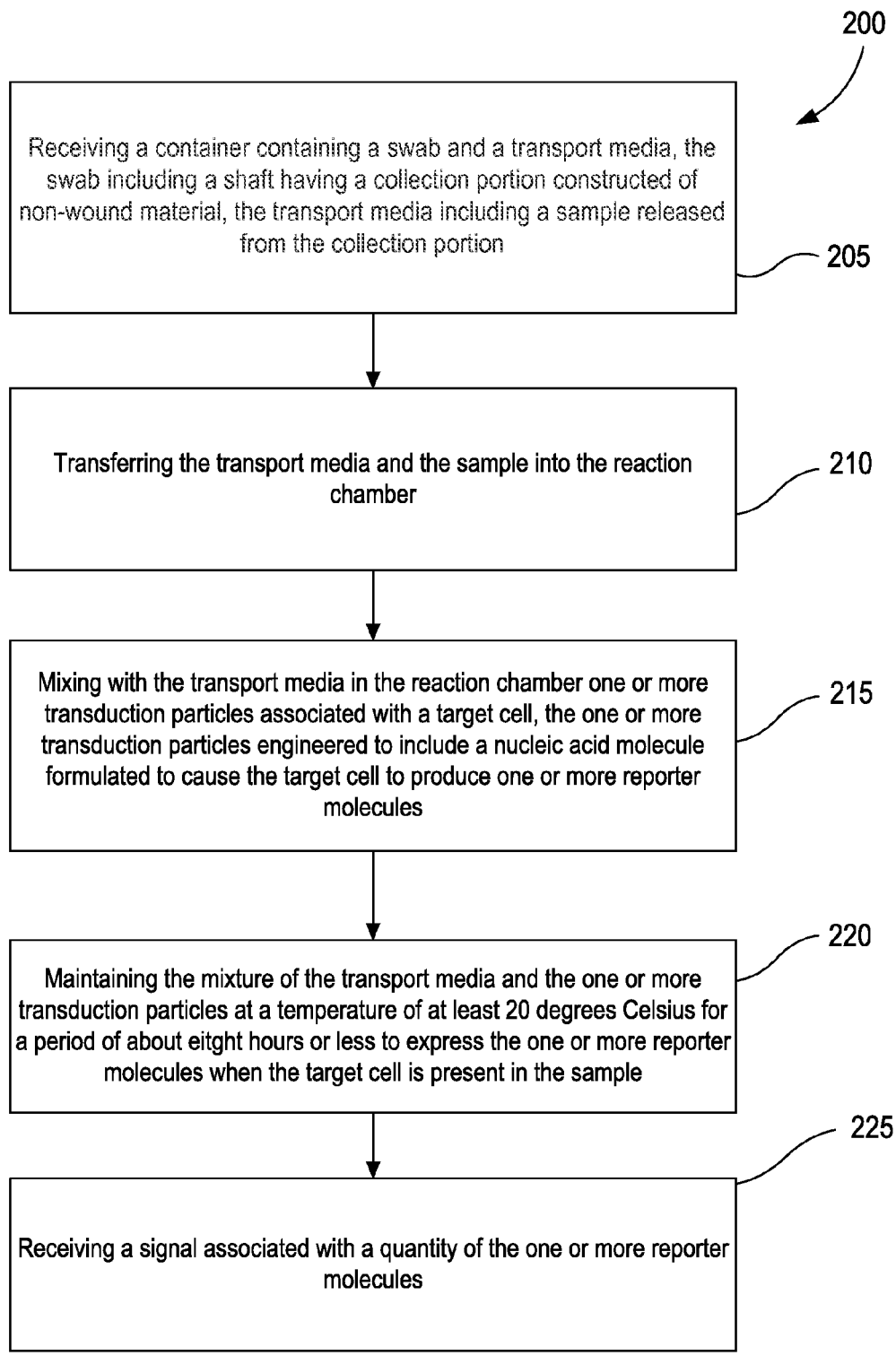
FIG. 22 is a flow chart of a method according to an embodiment.

In some embodiments, a method can involve using a sample collector formulated to maximize the sample collection efficiency and/or the efficiency of releasing the collected sample into a container assembly. For example, FIG. 22 is a flow chart of a method 200 according to an embodiment. As shown in FIG. 22, the method 200 includes receiving a container containing a swab and a transport media, at 205. The swab can be similar to the sample collectors described herein, and includes a shaft having a collection portion constructed from non-wound material. In some embodiments, the collection portion can be constructed from a material that is electrostatically assembled or otherwise flocked (i.e., a flocked swab) or a foam material, such as an open-cell foam-tipped swab. The transport media includes a sample released from the collection portion.

At 210, the transport media and the sample are transferred into a reaction chamber. The reaction chamber can be any reaction chamber described herein, such as the reaction chamber 4732. The transport media and the sample can be transferred via any suitable mechanism, such as via the transfer member 4030 (e.g., a pipette).

The transport media and one or more transduction particles associated with a target cell are mixed in the reaction chamber, at 215. The transduction particles can be any transduction particles described herein, and are engineered to include a nucleic acid molecule formulated to cause the target cell to produce one or more reporter molecules. In some embodiments, the one or more transduction particles can be non-replicative. In some embodiments, the one or more transduction particles can be devoid of a reporter molecule of the one or more reporter molecules. In yet further embodiments, the reporter molecule from the one or more reporter molecules can include one or more of a bacterial luciferase, an eukaryotic luciferase, a fluorescent protein, an enzyme suitable for colorimetric detection, a protein suitable for immunodetection, a peptide suitable for immunodetection or a nucleic acid that function as an aptamer or that exhibits enzymatic activity.

The transduction particles can be added to and/or mixed within the reaction chamber by any suitable mechanism. In some embodiments, the transduction particles can be included in the reagent container 4780 and/or the reagent container 4790 within the housing 4741 (or cap assembly) as described herein. In such embodiments, the transduction particles can be added to and/or mixed within the reaction chamber (e.g., the chamber 4732) by the application of a force to an actuator (e.g., the actuator 4750 and/or the actuator 4760), which thereby causes the transduction particles to be conveyed from the reagent container into the reaction chamber as described herein. In some embodiments, the transduction particles can be conveyed such that the dead volume within the cap assembly is between about 30 µL and about 50 µL. In some embodiments, the transduction particles can be conveyed such that the "dead volume" about 40 µL±9 µL. In some embodiments, the transduction particles can be conveyed such that the dispensed volume is about 285 µL with a coefficient of variation of about three percent. By limiting the dead volume and/or the part-to-part variation in the dead volume, the accuracy of delivery, and thus, the accuracy of the assay, can be improved.

In some embodiments, the transduction particles can be conveyed into the reaction chamber in a manner that reduces the turbulence generated therein. For example, in some embodiments, the transduction particles can be conveyed such that they impinge and/or contact the sidewall of the reaction chamber as described herein. In other embodiments, the transduction particles can be conveyed at a velocity and/or flow rate to promote mixing and/or reduce turbulence. For example, in some embodiments, the mixing of the transduction particles includes conveying the transduction particles into the reaction chamber by moving the actuator (e.g., the actuator 4750) linearly at a rate of between about 63 mm per second and about 81 mm per second. In some embodiments, the mixing of the transduction particles includes conveying the transduction particles into the reaction chamber by moving the actuator (e.g., the actuator 4750) linearly at a rate of about 72 mm per second.

In some embodiments, the reaction chamber can contain a reagent (e.g., in dried form including tablet form, and/or including an antibiotic, as described herein) formulated to mix with the transport media. The antibiotics can be selected and/or formulated to kill other non-targeted bacterial strains, for example, non-drug resistant strains, so that only the drug resistant strain survives. In this manner, the reporter molecules produced are necessarily produced by the remaining, targeted bacterial strains. In some embodiments, the antibiotic/series of antibiotics can be predisposed in the reaction chamber (for example, in the transport media, in a freeze-dried and/or lyophilized form or any other suitable form). In other embodiments, the antibiotic/series of antibiotics can be disposed in a separate compartment (e.g., in a reagent container, such as the reagent container 4790), and can be communicated into the sample solution on demand or at a predetermined time.

The mixture of the transport media and the one or more transduction particles is maintained at a temperature of at least 20 degrees Celsius for a period of about eight hours or less to express the one or more reporter molecules when the target cell is present in the sample, at 220. In some embodiments, the mixture can be maintained at about 37 degrees Celsius for about four hours. In yet other embodiments, the mixture can be maintained for about three hours or less, or about 2 hours or less. In yet other embodiments, the mixture can be maintained and at any suitable temperature, e.g., between the range of about 20 degrees Celsius and about 37 degrees Celsius.

A signal associated with a quantity of the one or more reporter molecules is received, at 225. The signal can be any suitable signal that is produced by certain reporter molecules, such as for example, an optical signal produced by a flash luminescence reaction. In some embodiments, the signal is associated with the quantity of reporter molecules within the sample. In some embodiments, the magnitude of the signal is independent from the quantity of the transduction particles above a predetermined quantity. Similarly stated, in some embodiments, the strength of the signal is substantially independent from the quantity of the transduction particles.

Although kit 4000 includes transport container assembly 4010, transfer tool 4030, and container assembly 4700, in other embodiments, a kit can include additional components and/or be devoid of any such components. For example, in some embodiments, a kit can be devoid of a transfer tool. In some embodiments, a kit can be devoid of a transfer tool and a transport chamber. In such embodiments, for example, a kit can include a transport cap (e.g., transport cap 4012, a sample collector (e.g., sample collector 4020), and a container assembly (e.g., container assembly 4700 or any other container assembly described herein). In this manner, a patient sample collected with and disposed on a sample collector can be placed within a reaction chamber (e.g., reaction chamber 4732 or any other reaction chamber described herein). In such embodiments, for example, the transport cap can be removably coupled to the reaction chamber. In this manner, the transport cap can be removed from the reaction chamber, and the reaction chamber can be removably coupled to a housing (e.g., housing 4741 or any other housing or cap assembly described herein). In yet further embodiments, a kit can include a transport cap (e.g., transport cap 4012), a sample collector (e.g., sample collector 4020), and a reaction chamber (e.g., reaction chamber 4732 or any other reaction chamber described herein).

Although FIG. 21 illustrates a method including transport container assembly 4010 and a separate reaction chamber, in other embodiments, a patient sample can be communicated from the sample collector 4020 directly to a reaction chamber (e.g., a reaction chamber 4732) without first being transferred to a transport container. In such embodiments, the patient sample can be communicated from the sample collector 4020 directly to the reaction chamber 4732, without the use of transfer tool 4030. In such embodiments, the patient sample can be collected at a collection site via sample collector 4020 (e.g., similar to operation 4210 described above). Next, the sample collector 4020 can be communicated to reaction chamber 4732, or any other reaction chamber disclosed herein. In this manner, the patient sample is communicated from the patient to the reaction chamber 4732. Once at least a portion of the patient sample and/or the sample collector 4020 are disposed within the reaction chamber 4732, transport cap 4012 can be removably coupled to the reaction chamber 4732. As such, the patient sample can be collectively contained and/or protected by the transport cap 4012, the reaction chamber 4732, and/or the sample collector 4020. In this manner, the patient sample can be stored, and/or transferred securely from the collection site to a testing and/or detection site. When desired (e.g., in preparation for target cell detection), the transport cap 4012 can be removed from the reaction chamber 4732, and the housing 4741 (or cap assembly) or any other housing described herein, can be removably coupled to the reaction chamber 4732 to complete the assay.

In some embodiments, the transport chamber 4014 and/or reaction chamber 4732 can contain a reagent or other composition formulated to mix with the sample to form an assay media or solution. Such reagent can be included within and/or a portion of the transport media, or alternatively, can be a separate composition. For example in some embodiments, the transport chamber 4014 and/or the reaction chamber 4732 can include a lyophilized tablet that is maintained separately from the transport media, and is mixed with the sample to form an assay media. For example, in some embodiments, the transport chamber 4014 and/or the reaction chamber 4732 can contain antibiotics (e.g. cefoxitin, oxacillin, cefotetan, amoxycillin, penicillin, erythromycin, azythromycin, cephalosporins, carbapenems, aminoglycosides, sulfonamides, quinolones, oxazolidinones, etc.). The inclusion of antibiotics can kill or otherwise prevent the expression and/or generation of a signal from reporter molecule from all drug-susceptible bacteria, e.g., in a bacteria cell viability and/or susceptibility assay of the types shown and described herein. The antibiotics can be selected and/or formulated to kill other non-targeted bacterial strains, for example, non-drug resistant strains, so that only the drug resistant strain survives. In this manner, the reporter molecules produced are necessarily produced by the remaining, targeted bacterial strains. In some embodiments, the antibiotic/series of antibiotics can be predisposed in the container (for example, in the solution, in a freeze-dried and/or lyophilized form or any other suitable form). In other embodiments, the antibiotic/series of antibiotics can be disposed in a separate compartment (e.g., in the body or cap of the container assembly), and can be communicated into the sample solution on demand or at a predetermined time.

In some embodiments, the reaction chamber can include colorant (e.g., a dye) along with any reagents disposed therein. Such dye can be used, for example, as a "process control" to ensure that the contents of the container (e.g., the reagents) were not disrupted and/or emptied before the sample was placed therein. In this manner, if during use, an instrument senses color in the sample mixture, a signal can be sent to indicate and/or confirm that the dried reagent substance was actually within the container. If no color is identified and/or detected, for example, the instrument can send an error signal indicating that the desired reagents were not, in fact, within the container during testing.

Figure 23:
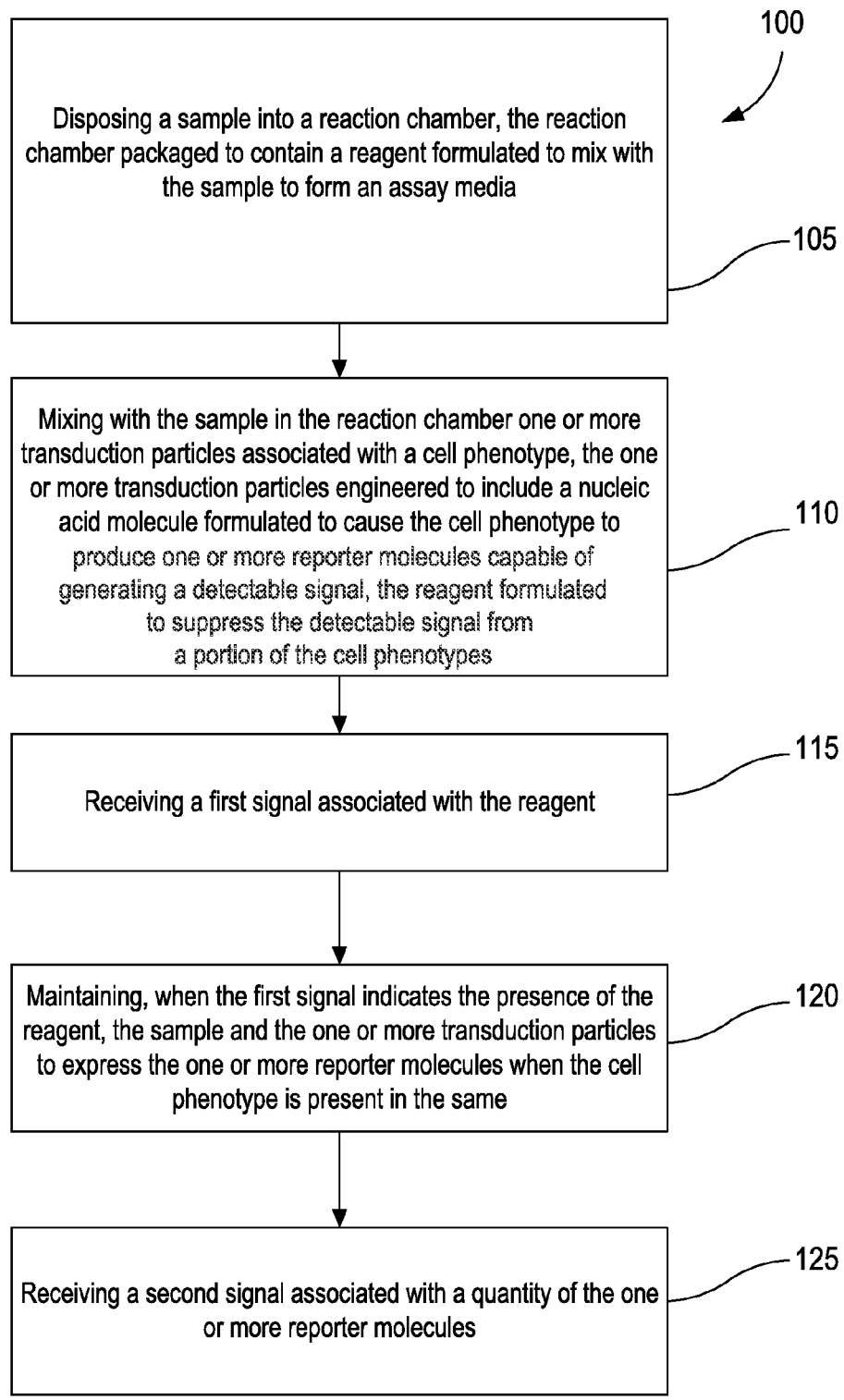
FIG. 23 is a flow chart of a method according to an embodiment.

In particular, FIG. 23 is a flow chart of a method 100 according to an embodiment. As shown in FIG. 23, the method 100 includes disposing a sample into a reaction chamber (any of the reaction chambers described herein, e.g., reaction chamber 4732), at 105. The reaction chamber is packaged to contain a reagent (e.g., a dried reagent, a lyophilized reagent) formulated to mix with the sample to form an assay media. In some embodiments, the reagent could be in pellet form. In other embodiments, the reagent can be dried in the tube (e.g., adhered to an inner surface of the reaction chamber 4732). Moreover, in some embodiments, the reagent can include an antibiotic and a colorant. In such embodiments, the antibiotic can be formulated to suppress production of the one or more reporter molecules in the portion of the cell phenotype, as described herein. In other embodiments, the reagent can include a substance formulated to suppress the transfer and/or conveyance of a detectable signal.

The sample in the reaction chamber is mixed with one or more transduction particles associated with a cell phenotype, at 110. The transduction particles can be contained in the reagent container 4780 and/or the reagent container 4790 and can be introduced into the sample as described herein. The one or more transduction particles are engineered to include a nucleic acid molecule formulated to cause the cell phenotype to produce one or more reporter molecules capable of generating and/or producing a detectable signal. In some embodiments, the detectable signal can be an optical signal produced by a flash luminescence reaction. In some embodiments, the transduction particles can be engineered to be incapable of lytic and/or lysogenic replication. In some embodiments, the one or more transduction particles can be derived from a bacteriophage. The reagent is formulated to suppress the detectable signal, either by suppressing production of compositions that produce the signal or by suppressing the conveyance and/or transmission of the signal. In some embodiments, for example, the reagent is formulated to suppress production of the one or more reporter molecules in at least a portion of the cell phenotype.

The transduction particles can be added to and/or mixed within the reaction chamber by any suitable mechanism. In some embodiments, the transduction particles can be included in the reagent container 4780 and/or the reagent container 4790 within the housing 4741 (or cap assembly) as described herein. In such embodiments, the transduction particles can be added to and/or mixed within the reaction chamber (e.g., the chamber 4732) by the application of a force to an actuator (e.g., the actuator 4750 and/or the actuator 4760), which thereby causes the transduction particles to be conveyed from the reagent container into the reaction container as described herein. In some embodiments, the transduction particles can be conveyed such that the dead volume within the cap assembly is between about 30 µL and about 50 µL. In some embodiments, the transduction particles can be conveyed such that the "dead volume" about 40 µL±9 µL. In some embodiments, the transduction particles can be conveyed such that the dispensed volume is about 285 µL with a coefficient of variation of about three percent. By limiting the dead volume and/or the part-to-part variation in the dead volume, the accuracy of delivery, and thus, the accuracy of the assay, can be improved.

In some embodiments, the transduction particles can be conveyed into the reaction chamber in a manner that reduces the turbulence generated therein. For example, in some embodiments, the transduction particles can be conveyed such that they impinge and/or contact the sidewall of the reaction chamber as described herein. In other embodiments, the transduction particles can be conveyed at a velocity and/or flow rate to promote mixing and/or reduce turbulence. For example, in some embodiments, the mixing of the transduction particles includes conveying the transduction particles into the reaction by moving the actuator (e.g., the actuator 4750) linearly at a rate of between about 63 mm per second and about 81 mm per second In some embodiments, the mixing of the transduction particles includes conveying the transduction particles into the reaction chamber by moving the actuator (e.g., the actuator 4750) linearly at a rate of about 72 mm per second.

A first signal associated with the reagent is received, at 115. In some embodiments, the first signal can be an optical signal associated with a colorant included within the reagent. In some embodiments, the first signal can be associated with a volume of the assay media within the reaction chamber. In this manner, the first signal can indicate the presence of the reagent. When the first signal indicates the presence of the reagent, the sample and the one or more transduction particles is maintained to express the one or more reporter molecules when the cell phenotype is present in the same, at 120.

A second signal associated with a quantity of the one or more reporter molecules is received, at 125. The second signal is the detectable signal, and can be any suitable signal that is produced by certain reporter molecules, such as for example, an optical signal produced by a flash luminescence reaction. In some embodiments, the second signal is associated with the quantity of reporter molecules within the sample. In some embodiments, the magnitude of the second signal is independent from the quantity of the transduction particles above a predetermined quantity. Similarly stated, in some embodiments, the strength of the second signal is substantially independent from the quantity of the transduction particles.

Moreover, in some embodiments, the portion of the cell phenotype can include a bacteria phenotype that is resistant to an antibiotic individually or in combination with another antibiotic. An antibiotic can include one or more of Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, or Mupirocin. In some embodiments, the portion of the cell phenotype can include a bacteria phenotype that are resistant to one or more of cefoxitin, vancomycin, teicoplainin, ampicillin/sulbactam, ciprofloxacin, meropenem, ceftazidime, ceftriaxone, piperacillin/tazobactam, or gentamicin.

In some embodiments, the method 100 can include disposing a substance into the sample. The substance is formulated to react with the one or more reporter molecules to enhance the second signal. For example, in some embodiments, the reporter molecule can be luciferase and the method 100 can employ the cap assembly and/or housing 4741 described above. In such embodiments, the reagent container 4780 and/or the reagent container 4790 can contain an aldehyde reagent formulated to trigger, initiate and/or catalyze a luminescence reaction that can be detected by the production of the signal. In some embodiments, the reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the assembly 4700 can be configured to maintain the additional reagent in fluidic isolation from the sample before being disposed into the sample. In this manner, the timing of the delivery of the additional reagent into the sample can be controlled. In some embodiments, the system can include a mechanism (e.g., mechanism for applying a force to the actuator 4750 and/or the actuator 4760 for adding the additional reagent at any suitable time and/or in any suitable manner to induce the detectable signal. For example, as described in more detail herein, in some embodiments, the system and/or the testing container can include a mechanism for conveying an additional reagent into the sample at a predetermined velocity (or flow rate) to promote the desired level of mixing.

For example, in some embodiments, the reagent and/or substrate can be conveyed such that it impinges and/or contacts the sidewall of the reaction chamber as described herein. In other embodiments, the reagent and/or substrate can be conveyed at a velocity and/or flow rate to promote mixing and/or reduce turbulence. A step in the luciferase reaction includes the first formation of a complex between luciferase and flavin mononucleotide. In the absence of a suitable aldehyde (i.e. the substrate), this complex is unable to proceed in the luminescence reaction. The luciferase reaction proceeds and emits light upon the addition of the aldehyde, and ideally, it is preferable that all complexed luciferases be triggered to emit photons simultaneously. This would result in a large flux of photons being emitted in a short period of time—i.e., a flash of light that can be readily detected. As supported by the test results presented herein, however, if the reagent and/or substrate is conveyed into the reaction chamber at a rate that is too high, the amount of light detected will decrease and/or the amount of light detected from replicates will exhibit increased variability resulting in an increase in the coefficient of variation associated with light detection. This reduction in performance is thought to be related to splashing and/or formation of bubbles in the solution that can result when the reagent and/or substrate is conveyed at a high velocity. Accordingly, the mixing of the reagent and/or substrate can be controlled to produce the desired light output performance. For example, in some embodiments, the mixing of the reagent and/or substrate includes conveying the reagent and/or substrate into the reaction chamber by moving the actuator (e.g., the actuator 4760) linearly at a rate of between about 63 mm per second and about 81 mm per second. In some embodiments, the mixing of the reagent and/or substrate includes conveying the reagent and/or substrate into the reaction chamber by moving the actuator (e.g., the actuator 4760) linearly at a rate of about 72 mm per second.

In some embodiments, a MRSA reporter assay can be developed and/or performed using any suitable system and method as described herein. In such embodiments, a non-replicative transduction particle is developed from a S. aureus-specific bacteriophage and the bacterial luciferase genes luxAB under the control of a constitutive promoter are incorporated. When this transduction particle introduces the reporter system into S. aureus, the constitutive promoter can express luxAB suitable for reporting on the presence of a viable S. aureus. If in addition, the antibiotic cefoxitin, or a similar anti-biotic, is also added prior to or simultaneously with mixing the transduction particles with S. aureus cells, if the cells do not contain and express the mecA gene, no luxAB will be expressed in the assay, thus indicating that there is no MRSA. If, however, the cells do contain and express the mecA gene, luxAB will be expressed in the assay, thus indicating that the cells are MRSA (i.e., resistant to inhibition by cefoxitin).

Figure 24:
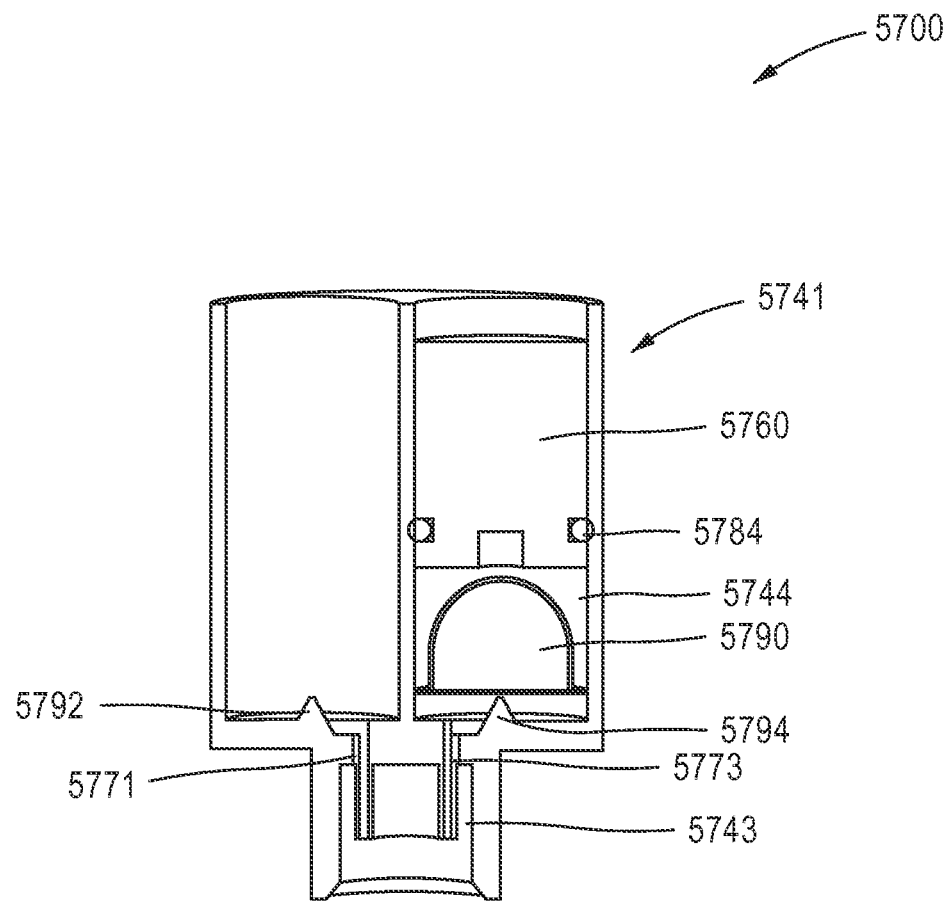
FIG. 24 is a cross-sectional view of a housing assembly according to an embodiment.

Although container assembly 4700 is shown as including a threaded coupling between the housing 4741 and the reaction chamber 4732, in other embodiments, a housing can be coupled to a reaction chamber via a press fit. For example, FIG. 24 shows a side, partial cross-sectional view of a container assembly 5700 according to an embodiment. The container assembly 5700 can be used with and manipulated by any of the instruments and/or any of the components described herein and in U.S. patent application Ser. No. 13/802,461, entitled "Systems and Methods for Detection of Cells using Engineered Transduction Particles," which is incorporated herein by reference in its entirety. In this manner, the container assembly 5700 and any of the container assemblies described herein can be used to detect and/or identify target cells (e.g., bacteria) within a sample according to any of the methods described herein or in the '461 application. For example, in some embodiments, the container assembly 5700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 5700 is used in methods of cell identification and/or detection that do not involve removal of contents from the container assembly 5700, separation of the contents within the container assembly 5700, washing of the contents within the container assembly 5700 and/or rinsing of the contents within the container assembly 5700.

The container assembly 5700 includes a housing 5741, a first actuator (not shown), a second actuator 5760, and a reaction chamber (not shown). The housing 5741 is can be removably coupled to the reaction chamber. For example, as shown in FIG. 24, the housing 5741 can be coupled to a proximal portion of the reaction chamber via a press fit portion 5743. Thus, the housing 5741 (and the components disposed therein) can be stored separately from and/or spaced apart from the reaction chamber 5732. In this manner, a user can then dispose a sample into the reaction chamber in accordance with the methods described herein (and in the '461 application, which is incorporated herein by reference in its entirety), and can then assemble the housing 5741 (or "cap assembly") to the reaction chamber (or "tube") and complete the steps for cell identification, as described herein.

The housing 5741 defines a first reagent volume (not identified) configured to receive a first reagent container (not shown) and a second reagent volume 5744 configured to receive a second reagent container 5790. The housing 5741 includes a first puncturer 5792, a second puncturer 5794, a first delivery pathway 5771, and a second delivery pathway

5773. The first puncturer 5792, the second puncturer 5794, the first delivery pathway 5771, and the second delivery pathway 5773 are similar to the corresponding structure of the housing 4741 described above, and are therefore not described in detail.

The press fit portion 5743 includes a recess or groove within which a portion of the reaction chamber can be securely disposed (i.e., to form a press or interference fit). In some embodiments, the press fit portion 5743 can include a seal member (e.g., an o-ring or the like) to define a substantially fluid-tight seal when the housing 5741 is coupled to the reaction chamber.

The second actuator 5760, as shown, is substantially solid, and has a width substantially similar to a width of the second reagent volume 5744. In this manner, undesirable "dead space" within the second reagent volume 5744 (and/or the first reagent volume, not identified) can be limited. In use, the container assembly 5700 can be actuated in a manner similar to that described above with respect to the housing 4741 and/or cap assembly. In particular, the second actuator 5760 can be manipulated within the second reagent volume 5760 to convey a reagent from the second reagent volume 5760 to the reaction chamber.

Figure 26:
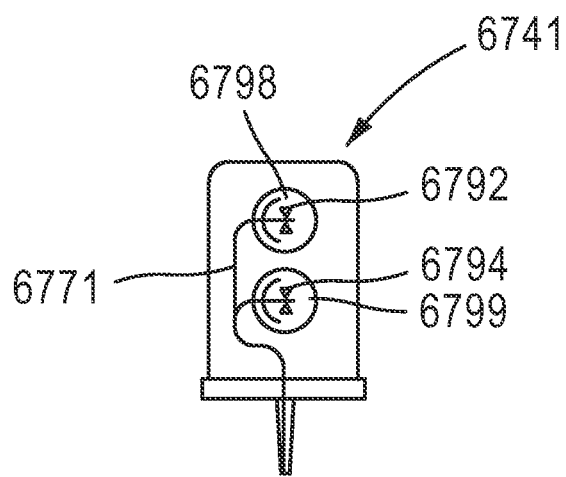
FIGS. 26 and 27 are front views of a housing assembly according to an embodiment
Figure 27:
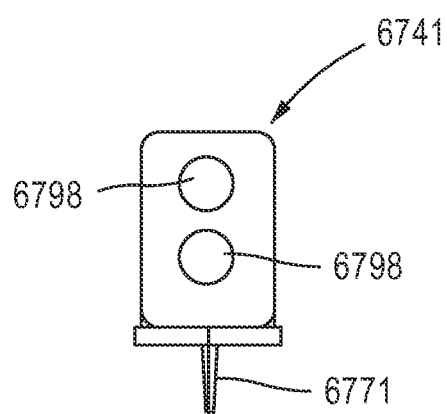

Although the reagent containers (e.g., reagent container 4780, reagent container 4790, reagent container 5780, reagent container 5790) have been described and illustrated in positions lateral to each other when disposed within a housing (e.g., housing 4741), in other embodiments, reagent containers can be disposed within a housing in any suitable manner or configuration, such as for example, in a vertical configuration. For example, FIGS. 25A-C, and FIGS. 26 and 27 show a housing 6741 (and "cap assembly") according to an embodiment. In particular, FIGS. 25A-C show the housing 6741 in a cross-sectional side view (FIG. 25A), a cross-sectional front view (FIG. 25B), and a bottom view (FIG. 25C). FIGS. 26 and 27 show the housing 6741 (without the reagent containers) in a cross-sectional front view (FIG. 26) and a front view (FIG. 27).

As shown, the housing 6741 defines a reagent volume 6742 (FIG. 25B) configured to receive a first reagent container 6780 and a second reagent container 6790. As shown in FIG. 26, the housing 6741 includes first rupture member 6798 and a second rupture member 6799. The first rupture member 6798 and the second rupture member 6799 include a first puncturer 6792 and a second puncturer 6794, respectively. The rupture member 6798 and the rupture member 6799 each define, at least in part, a delivery pathway 6771. The delivery pathway 6771 places the reagent volume 6742 in fluidic communication with a reaction chamber (not shown). In addition, as shown, the delivery pathway 6771 places the first rupture member 6798 and the second rupture member 6799 in fluidic communication with each other. In this manner, contents of the reagent container 6780 can communicate (e.g., mix) with contents of the reagent container 6790 before reaching the reaction chamber (not shown) or a portion thereof. Such an arrangement, in some embodiments, can promote mixing and/or minimize aeration, overspray and/or undesirable turbulence of the contents from the reagent container 6780 and/or the reagent container 6790.

Although shown to be in fluidic communication, in other embodiments, the first rupture member 6798 and the second rupture member 6799 can be maintained in fluidic isolation from each other. For example, in some embodiments, the first rupture member 6798 can define in part a first delivery pathway (not shown), and the second rupture member 6799 can define in part a second delivery pathway (not shown) such that the second delivery pathway that is distinct from and/or fluidic isolated from the first delivery pathway.

The rupturing of reagent container 6780 and reagent container 6790 can be initiated and/or caused at least in part by any suitable means. For example, in some embodiments, the housing 6741 can be manipulated such that a pressure within an interior portion of the housing 6741 is altered, resulting in the reagent container 6780 and/or the reagent container 6790 being urged against the first rupture member 6798 and the second rupture member 6799, respectively. In this manner, the puncturer 6792 of the first rupture member 6798 and/or the puncturer of the second rupture member 6799 can rupture the first reagent container 6780 and the second reagent container 6790, respectively. For example, in some embodiments the housing 6741 can include one or more actuators (similar to the actuator 4750).

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

Although the puncturers (e.g., puncturer 1792) are described herein as being substantially stationary (e.g., fixed) with respect to the housing (e.g., housing 1741), in other embodiments, a puncturer can be moveable (e.g., slideable, rotatable, etc.) with respect to the housing.

In use, any suitable container assembly (e.g., container assembly 1700, 2700, 3700, 4700, 5700, etc.) can receive a patient sample (e.g., bacteria) via any suitable method. For example, in some embodiments, the container assembly can be provided within a kit including additional components, for example, swabs for collecting patient samples. In such embodiments, the sample can be delivered to the testing container via the swab. In other embodiments, the sample can be delivered to the container assembly from a transportation container (e.g., via a pipette, syringe, etc.).

Although the reagent container 4780 and the reagent container 4790 are shown and described has having a specific shape and construction, any of the reagent containers (or blister packs) described herein can be constructed from any suitable material, for example, PVC, and/or from a combination of different materials (e.g., pharmaceutical-grade copolymer, cyclic olefin copolymer film, Tekniflex COC P12P, PCTFE film lamination, Tekniflex VA10200). In some embodiments, the reagent containers or blister packs described herein can be constructed of materials that are compatible with methods of bioburden reduction that include gamma irradiation.

Moreover, any of the blister packs described herein can be any suitable size or shape. For example, in some embodiments, a blister pack can include a linear portion (e.g., the skirt of the blister pack, a flat surface) and a non-linear portion (e.g., a rounded surface). In such embodiments, a blister pack can be configured to limit dead volume therein (e.g., empty space, a void, a cavity, an area without of reagent, etc.). In some embodiments, instead of or in addition to the linear portion, the blister pack can include a concave portion. In this manner, as the portion is ruptured (e.g., the foil begins to bulge), efficient and/or sufficient contact between the surface of the concave portion and the puncture member can be established. As such, dispensation of the contents of the blister pack can be maximized and/or reduced dead volume can be achieved.

Any of the reagent containers and/or blister packs described herein (e.g., the reagent container 4780 and/or the reagent container 4790) can contain a pre-determined amount of any suitable reagent (e.g., assay reagent, antibiotic reagent, transduction particles, substrate reagent, etc.). The pre-determined amount can be measured in any suitable manner, for example, by volume of specific concentrations. Moreover, any of the reagent containers and/or blister packs can include any of the transduction particles described herein and in U.S. Provisional Application Nos. 61/983,765, entitled "Reagent Cartridge for Detection of Cells," filed Apr. 24, 2014; 61/779,177, entitled "Non-Replicative Transduction Particles and Transduction Particle-Based Reporter Systems," filed Mar. 13, 2013; 61/939,126, entitled "Systems and Methods for Packaging Nucleic Acid Molecules into Non-Replicative Transduction Particles and Their Use as Cellular Reporters," filed Feb. 12, 2014; and 61/897,040, entitled "Transcript Detection Systems and Methods," filed Oct. 29, 2013, and International Patent Application No. PCT/US2014/026536, entitled "Non-Replicative Transduction Particles and Transduction Particle-Based Reporter Systems," filed Mar. 13, 2014, each of which is incorporated herein by reference in its entirety Although the container assemblies, systems and methods are described herein as being used to detect and/or identify target cells using non-replicative transduction particles, in other embodiments, any of the container assemblies and systems described herein can be used in conjunction with any suitable reagents to detect a target bacteria. For example, in some embodiments, the assemblies and systems described herein can be used in conjunction with replication-competent transduction particles, such as, for example, a traditional phage reporter.

For example, in some embodiments, a housing or "cap assembly" (e.g., the housing 4741) contains two reagent volumes (e.g., the volumes 4742 and 4744) and/or two reagent containers (e.g., the reagent containers 4780 and 4790). The first reagent volume and/or reagent container contains an engineered luciferase-reporter bacteriophage, such as for example the Nanoluc® luciferase produced by Promega Corp. The second reagent volume and/or second reagent container contains a substrate, such as furimazine. In some embodiments, the substrate can be formulated for specific compatibility with the luciferase-reporter bacteriophage (e.g., the Nanoluc®) contained within the first reagent volume.

In use, after the sample is added to the reaction chamber and the cap assembly is coupled thereto, the method includes adding the contents of the first reagent volume to the reaction chamber. The sample and the first reagent (e.g., the reporter phage, such as the Nanoluc® reporter phage) are maintained at or above a predetermined temperature for a predetermined time period (i.e., the sample is incubated). If the sample contains bacteria that the reporter phage is designed to target, then the reporter phage causes viable target bacteria to express the luciferase during the incubation period. After the incubation period, the contents of the second reagent volume are added to the reaction chamber providing the substrate (i.e., furimazine) that can react with any expressed luciferase and generate a luminescent signal thereby indicting the presence of the target bacteria in the sample. The light output produced during this assay (and any of the assays described herein) can be detected using any suitable instrument, such as the instruments described in the '461 application.

In some embodiments, a method includes using a luciferase reporter phage to identify the presence of antibiotic resistant bacteria. For example, in some embodiments, a reaction chamber (e.g., the reaction chamber 4732) can include an antibiotic, for example, as a dry reagent. Any antibiotics of the type described herein can be used. A housing or "cap assembly" (e.g., the housing 4741) is configured to be removably coupled to the reaction chamber and contains two reagent volumes (e.g., the volumes 4742 and 4744) and/or two reagent containers (e.g., the reagent containers 4780 and 4790). The first reagent volume and/or reagent container contains any suitable reporter phage. The second reagent volume and/or second reagent container contains a substrate, such as luciferin.

In use, after the sample is added to the reaction chamber and the cap assembly is coupled thereto, the method includes adding the contents of the first reagent volume to the reaction chamber. The sample and the first reagent (e.g., the reporter phage) are maintained at or above a predetermined temperature for a predetermined time period (i.e., the sample is incubated). In this manner, any bacteria present within the sample that are resistant to the antibiotic are able to propagate and express luciferase. Conversely, those bacteria within the sample that are sensitive to the antibiotic do not propagate and/or do not express luciferase and/or are otherwise unable to successfully mediate a luminescence reaction. After the incubation period, the contents of the second reagent volume are added to the reaction chamber providing the substrate that can react with any expressed luciferase to generate a luminescent signal thereby indicting the presence of the target bacteria in the sample. The light output produced during this assay (and any of the assays described herein) can be detected using any suitable instrument, such as the instruments described in the '461 application.

In other embodiments, a luciferase reporter assay can employ the bacterial luciferase genes luxAB as the first reagent, and its substrate, an aldehyde such as decanal, as the second reagent. In yet other embodiments, a luciferase reporter assay can employ the bacterial luciferase genes operon including the genes luxCDEAB, thus eliminating the need for the addition of a substrate (e.g., aldehyde) since the operon contains genes that enable the target bacteria to produce the aldehyde. In such embodiments, the cap assembly need only define one reagent volume or include one reagent container. Such methods can be used in conjunction with an antibiotic and/or antimicrobial compound, as described herein.

Although the container assemblies, systems and methods are described herein as being used to detect and/or identify target cells, such as bacteria, in other embodiments, any of the container assemblies, systems and methods described herein can be used in conjunction with any suitable homogenous assay. Moreover, although the container assemblies, systems and methods are described herein as being used to detect and/or identify target cells, such as bacteria, in other embodiments, any of the container assemblies, systems and methods described herein can be used in conjunction with any assay that incorporates a "switchable signal"—i.e., reporter system that enables a homogeneous assay where a specific signal can be generated and detected without the need for washing or separation steps. Similarly stated, any of the container assemblies, systems and methods described herein can be used in conjunction with any suitable assay in which a signal is not produced unless or until a reaction with an analyte occurs and/or in which no amount of a reporter is present in the sample until the conditions are such that the reporter is produced. Moreover, although the "switchable"

reporter molecules are described herein as being molecules that can be expressed from reporter genes encoding enzymes mediating luminescence reactions, in other embodiments a switchable reporter can be mediated by the direct addition of a molecule that is 'switched on' to produce a signal upon, for example, a conformational change mediated by the binding to a target analyte, such as for example, the switchable aptamer designed to detect S-adenosylmethionine consisting of an RNA termed Spinach and the fluorophore 3,5-difluoro-4-hydroxybenzylidene imidazolinone (DFHBI) designed to include a transducer element that binds to S-adenosylmethionine that causes as a conformational change that allows for fluorophore activation as described in "Fluorescence imaging of cellular metabolites with RNA, Science. March 2012, vol. 335, no. 6073, 9, pp. 1194." In yet other embodiments, a switchable reporter include anything that exhibits a first signal before reacting with an analyte and a second (different) signal after reacting with the analyte.

In some embodiments, the container assemblies and systems described herein can be used in a hygiene assay to determine the presence of living (or previously living) organisms by detecting the presence of adenosine triphosphate (ATP) within the sample. In such embodiments, a sample of unknown hygiene is added to a reaction chamber (e.g., the reaction chamber 4732). The method further includes attaching a housing or "cap assembly" (e.g., the housing 4741) to the reaction chamber. As described above, the housing contains two reagent volumes (e.g., the volumes 4742 and 4744) and/or two reagent containers (e.g., the reagent containers 4780 and 4790). The first reagent volume and/or reagent container contains a nutrient media formulated such that any organisms present in the sample will remain metabolically active. The nutrient media can be similar to and/or contain any of the nutrients or compositions of the transport media described herein. The second reagent volume and/or second reagent container contains a formulation including a eukaryotic luciferase enzyme, luciferin, and a lysis reagent. As described below, when ATP is present a light output is produced (i.e., via a luminescence reaction) that can be detected using any suitable instrument, such as the instruments described in the '461 application.

In use, after the sample is added to the reaction chamber and the cap assembly is coupled thereto, the method includes adding the contents of the first reagent volume to the reaction chamber to provide nutrients for any organisms in the sample to remain metabolically active. In some embodiments, the sample can be incubated for a time period to allow any organisms in the sample to grow. Such incubation can be performed using any of the instruments described in the '461 application for any suitable time and at any suitable temperature. The contents of second reagent volume can then be added to the reaction chamber. The lysis reagent (included within the second reagent chamber) is formulated to release adenosine triphosphate produced by viable organisms that may exist within the sample. If the sample contains any viable organisms then the luciferase and luciferin will react along with extracted adenosine triphosphate causing a luminescent reaction and thus indicating the presence of viable organisms in the reaction.

In other embodiments, a method of performing a hygiene assay need not include adding a nutrient medium, as indicated above. Thus, in some embodiments, the cap assembly can include only a single reagent volume, actuator and/or reagent container. In such embodiments, the method can include reporting on the presence of viable organisms directly from a sample without an incubation step.

In other embodiments, a method of performing a hygiene assay can include delivering a variety of different compositions using a cap assembly of the types described herein. In this manner, certain compositions used in the assay can be stored separately from and/or spaced apart from other compositions. For example, such methods that employ the cap assemblies described herein can facilitate separate storage of the lysis (or extraction) reagent, which can limit the likelihood that the lysis agent will negatively impact the performance of the luciferase enzyme and/or the luciferin. For example, in some embodiments, the luciferin and/or the luciferase can be incorporated into a dry reagent and placed into the reaction chamber. This arrangement also accommodates the use of luciferin and/or luciferase formulations that are not stable in liquid form. For example, in some embodiments, the luciferin can be included as a dried reagent within the reaction chamber, the first reagent volume (of the cap assembly) can include the lysis reagent, and the second reagent volume (of the cap assembly) can include the eukaryotic luciferase enzyme. In use, the lysis reagent can be added at a different time than the luciferase enzyme, thus allowing for a controlled lysis period prior to adding the luciferase enzyme. In other embodiments, the luciferase enzyme can be included as a dried reagent within the reaction chamber, the first reagent volume (of the cap assembly) can include the lysis reagent, and the second reagent volume (of the cap assembly) can include the luciferin. In yet other embodiments, both the luciferase enzyme and the luciferin can be included as a dried reagent within the reaction chamber and a reagent volume (of the cap assembly) can include the lysis reagent.

In some embodiments, a method of performing a hygiene assay can include exposing the sample to an antimicrobial compound. The antimicrobial compound can include any substance, such as for example, an antibiotic, formulated and/or selected to kill non-targeted organisms (e.g., bacterial strains or the like). In this manner, the method can be used to indicate the presence of viable organisms in the reaction that are insensitive or resistant to the antimicrobial compound. In such embodiments, the antimicrobial compound can be included within the reaction chamber, for example, in a dried form. Thus, in some embodiments, a method includes adding a sample of unknown hygiene to the reaction chamber containing the antimicrobial compound. A housing or "cap assembly" (e.g., the housing 4741) is attached to the reaction chamber. As described above, the housing contains two reagent volumes (e.g., the volumes 4742 and 4744) and/or two reagent containers (e.g., the reagent containers 4780 and 4790). The first reagent volume and/or reagent container contains a nutrient media formulated such that any organisms present in the sample will remain metabolically active. The nutrient media can be similar to and/or contain any of the nutrients or compositions of the transport media described herein. The second reagent volume and/or reagent container contains a formulation including a eukaryotic luciferase enzyme, luciferin, and a lysis reagent. As described below, when ATP is present a light output is produced (i.e., via a luminescence reaction) that can be detected using any suitable instrument, such as the instruments described in the '461 application.

After the sample is added to the reaction chamber and the cap assembly is coupled thereto, the contents of the first reagent volume can be added to the reaction chamber to provide nutrients for any organisms in the sample (that are resistant to the antimicrobial compound) to remain metabolically active. In some embodiments, the sample can be incubated for a time to allow any organisms that are resistant to the antimicrobial compound in the sample to grow. Such incubation can be performed using any of the instruments described in the '461 application for any suitable time and at any suitable temperature. The contents of second reagent volume can then be added to the reaction chamber. The lysis reagent (included within the second reagent chamber) is formulated to release adenosine triphosphate produced by viable organisms that may exist within the sample (i.e., those that are insensitive or resistant to the antimicrobial compound). If the sample contains any viable organisms then the luciferase and luciferin will react along with extracted adenosine triphosphate causing a luminescent reaction and thus indicating the presence of such viable organisms in the reaction.

In some embodiments, the container assemblies and systems described herein can be used to detect the presence of certain enzymes in a sample. In this manner, the function and/or characteristics of any organisms present within a sample can be determined. For example, in some embodiments, a method includes determining the presence of a betalactamase enzyme, which can be indicative of a bacteria that is resistant to certain antibiotics. In such embodiments, a reaction chamber (e.g., the reaction chamber 4732) can include a caged luciferase substrate (e.g., in a dried form), such as for example, a caged D-luciferin molecule such as those β-lactam-d-luciferin (Bluco) described in "Hequan Yao et al., A Bioluminogenic Substrate for In Vivo Imaging of Beta-Lactamase Activity, Angewandte Chemie International Edition, August 2007, vol. 46, pp. 7031-7034". The caged luciferase substrate can be designed and/or engineered to have limited or no reactivity as the luciferase substrate unless a betalactamase enzyme first reacts with the caged luciferase substrate such that it un-cages the substrate. A housing or "cap assembly" (e.g., the housing 4741) is configured to be removably coupled to the reaction chamber. The housing contains two reagent volumes (e.g., the volumes 4742 and 4744) and/or two reagent containers (e.g., the reagent containers 4780 and 4790). The first reagent volume and/or reagent container contains a cell lysis reagent. The second reagent volume and/or second reagent container contains a bioluminescent molecule such as Renilla luciferase.

After the sample is added to the reaction chamber and the cap assembly is coupled thereto, the method includes adding the contents of the first reagent volume to the reaction chamber. In this manner, any cells that may be present in the sample are lysed. If the sample contains target cells that express the betalactamase, such lysing of the cells releases the betalactamase and other intracellular molecules. The method then includes adding the contents of the second reagent volume to the reaction chamber. If betalactamase is present, it is able to un-cage the caged luciferin and allow the un-caged luciferase substrate to react with the luciferase (added from the second reagent volume, e.g., the Renilla luciferase) thereby producing a luminescence signal that is indicative of the presence of the betalactamase enzyme in the sample. The light output produced during this assay (and any of the assays described herein) can be detected using any suitable instrument, such as the instruments described in the '461 application.

In other embodiments, the caged luciferase substrate can be included in any suitable portion (or volume) of the container assembly and/or can be added at any suitable juncture of the method. For example, in some embodiments, a first reagent volume of a cap assembly can include a non-replicative transduction particle designed to express Renilla luciferase in the target cell. A second reagent volume can include a caged luciferase substrate designed to have limited or no reactivity as the luciferase substrate unless a betalactamase enzyme first reacts with the caged luciferase substrate such that it un-cages the substrate.

After the sample is added to the reaction chamber and the cap assembly is coupled thereto, the method includes adding the contents of the first reagent volume to the reaction chamber. The resulting solution is then maintained at or above a predetermined temperature for a time period (i.e., the solution is incubated). In this manner, if the sample contains target cells, the non-replicative transduction particle is able to cause the target cell to express Renilla luciferase. The method then includes adding the contents of the second reagent volume to the reaction chamber. If the target bacteria produces a betalactamase, the betalactamase is able to un-cage the caged luciferase substrate and allow the un-caged luciferase substrate to react with the luciferase thereby producing a luminescence signal that is indicative of the presence of the betalactamase enzyme in the sample. The light output produced during this assay (and any of the assays described herein) can be detected using any suitable instrument, such as the instruments described in the '461 application Although the methods are shown and described as determining the presence of a betalactamase enzyme, in other embodiments, methods and system can be used to determine the presence of any suitable enzyme. For example, in some embodiments, a method includes determining the presence of a carbapenemase enzyme. In such embodiments, a reaction chamber (e.g., the reaction chamber 4732) can include a dried carbapenemase substrate such as a carbapenem or cephamycin. A housing or "cap assembly" (e.g., the housing 4741) is configured to be removably coupled to the reaction chamber. The housing contains two reagent volumes (e.g., the volumes 4742 and 4744) and/or two reagent containers (e.g., the reagent containers 4780 and 4790). The first reagent volume and/or reagent container contains a cell lysis reagent. The second reagent volume and/or second reagent container contains a reagent containing pH indicator formulated such that when added to the sample, the reaction will change color when the pH of the reaction mixture is comprised between 6.4 and 8.4.

After the sample is added to the reaction chamber and the cap assembly is coupled thereto, the method includes adding the contents of the first reagent volume to the reaction chamber. In this manner, any cells that may be present in the sample are lysed. If the sample contains target cells that express the carbapenemase, such lysing of the cells releases the carbapenemase and other intracellular molecules. The method then includes adding the contents of the second reagent volume to the reaction chamber. If carbapenemase is present, it reacts with the carbapenemase substrate and causes a color change via the pH indicator wherein a color change indicates the presence of carbapenemase-producing bacteria in the sample. The color change produced during this assay (and any of the assays described herein) can be detected using any suitable instrument, such as the instruments described in the '461 application.

In some embodiments, the container assemblies and systems described herein can be used in a DNA sequencing assay. In such embodiments, a reaction chamber (e.g., the reaction chamber 4732) contains a composition of dried aptamer molecules and a dried fluorophore. The dried aptamer molecules are formulated, engineered and/or designed to bind to a target sequence of DNA. The dried fluorophore (also referred to as a dye) is designed to preferentially fluoresce when bound to a complex formed by the binding of the aptamer to the target DNA sequence. A housing or "cap assembly" (e.g., the housing 4741) is removably coupleable to the reaction chamber. As described above, the housing contains two reagent volumes (e.g., the volumes 4742 and 4744) and/or two reagent containers (e.g., the reagent containers 4780 and 4790). The first reagent volume and/or reagent container contains a buffer solution designed to produce and/or promote conditions that are favorable for aptamer/target DNA/fluorophore binding. The second reagent volume and/or second reagent container contains a formulation containing an oligonucleotide designed to bind to the target DNA molecule and displace (e.g., "out-compete") an aptamer that may already be bound to the target DNA molecule.

In use, after the sample is added to the reaction chamber and the cap assembly is coupled thereto, the method includes adding the contents of the first reagent volume to the reaction chamber. Because the addition of the first reagent produces conditions favorable for aptamer/target DNA/fluorophore binding, if the sample contains target DNA, then binding will occur and a fluorescence signal from the complexed fluorophore can be detected. In this manner, the aptamer molecules can be considered as a "switchable" aptamer. After time period has elapsed, the contents of the second reagent volume can be added to the reaction chamber. If the fluorescence signal is eliminated after the addition of the oligonucleotides introduced from the second reagent volume, then if the loss of signal is due to the displacement of the aptamer from the target DNA (and therefore displacement of the fluorophore from the now un-complexed aptamer) by the oligonucleotide. Such loss of signal serves as confirmation that the initial fluorescent signal was specifically due to the complexing of the aptamer to the target DNA. The light output produced during this assay (and any of the assays described herein) can be detected using any suitable instrument, such as the instruments described in the '461 application.

In some embodiments, DNA sequence detection systems and methods can include detection of DNA within live cells. For example, in some embodiments, the method described above can be modified such that the reaction chamber (e.g., the reaction chamber 4732) contains a dried fluorophore that is formulated and/or engineered such that it can enter live cells when a sample containing live cells is added to a reaction chamber. Moreover, the fluorophore is also designed to preferentially fluoresce when bound to a complex formed by the binding of the aptamer to the target DNA sequence. The housing or "cap assembly" (e.g., the housing 4741) used in conjunction with the method contains two reagent volumes (e.g., the volumes 4742 and 4744) and/or two reagent containers (e.g., the reagent containers 4780 and 4790). The first reagent volume and/or reagent container contains a liposome and an aptamer. The aptamer can be similar to those described above, and are formulated, engineered and/or designed to bind to a target sequence of DNA. The liposomes can carry the aptamers directly into the live cells, or can carry a DNA sequence designed to express the aptamers within the live cells. The second reagent volume and/or second reagent container contains a lysis reagent to release the molecules within the live cell and an oligonucleotide designed to displace the aptamer from the target DNA sequence (similar to that described above).

In use, after the sample is added to the reaction chamber and the cap assembly is coupled thereto, the contents of the first reagent volume can be added to the reaction chamber. After delivery of the aptamer into the reaction chamber, the aptamer is delivered into the cells via the liposome contained in the first reagent volume. In other embodiments, any other suitable mechanism for transporting the aptamers into the cells can be used. Moreover, in some embodiments, the liposomes can carry and/or transport the aptamers directly into the living cells, whereas in other embodiments, the liposomes can carry and/or transport a DNA sequence designed to express the aptamers within the live cells. After the aptamer is inside of the live cell, it can complex with a target DNA sequence allowing for the complex to bind the fluorophore and produce a fluorescent signal that is indicative of the aptamer binding to the target DNA sequence. After a time period, the contents of the second reagent volume can be added to the reaction chamber. The addition of the lysis reagent releases the molecules within the live cell and the oligonucleotide can thus displace the aptamer from the target DNA sequence. Accordingly, if the fluorescence signal is eliminated after the addition of the oligonucleotides introduced from the second reagent volume, then the loss of signal is due to the displacement of the aptamer from the target DNA (and therefore displacement of the fluorophore from the now un-complexed aptamer) by the oligonucleotide. This serves as confirmation that the initial fluorescent signal was specifically due to the complexing of the aptamer to the target DNA. The light output produced during this assay (and any of the assays described herein) can be detected using any suitable instrument, such as the instruments described in the '461 application.

In some embodiments, the container assemblies and systems described herein can be used in an assay to determine the transcription activity of a sample. In such embodiments, a sample can be disposed within a reaction chamber (e.g., the reaction chamber 4732). A housing or "cap assembly" (e.g., the housing 4741) is removably coupleable to the reaction chamber. The housing contains two reagent volumes (e.g., the volumes 4742 and 4744) and/or two reagent containers (e.g., the reagent containers 4780 and 4790). The first reagent volume and/or reagent container contains liposomes carrying molecular beacons designed to fluoresce when the beacon has bound to a target RNA transcript sequence. The second reagent volume and/or second reagent container contains a formulation containing a lysis reagent and oligonucleotides designed to preferentially bind to the target RNA sequence and displace a bound molecular beacon (e.g., "out-compete" the beacon).

After the sample is added to the reaction chamber and the cap assembly is coupled thereto, the method includes adding the contents of the first reagent volume to the reaction chamber. The liposomes added can deliver the molecular beacons into live cells that may be present in the sample. If the sample contains live cells of bacteria that are transcribing the target RNA, then the molecular beacons can bind to the target RNA sequence and produce a fluorescent signal. The fluorescent signal can be detected using any suitable instrument, such as the instruments described in the '461 application. The contents of the second reagent volume are then added to the reaction chamber. The addition of the lysis reagent releases the molecules within the live cell and the oligonucleotide can thus displace the molecular beacon from the target RNA sequence. Accordingly, if the fluorescence signal is eliminated after the addition of the oligonucleotides introduced from the second reagent volume, then the loss of signal is due to the displacement of the molecular beacon from the target RNA (and therefore the re-quenching of the displaced molecular beacon) by the oligonucleotide. This serves as confirmation that the initial fluorescent signal was due to the complexing of the molecular beacon to the target RNA. The light output and/or change in light output produced during this assay (and any of the assays described herein) can be detected using any suitable instrument, such as the instruments described in the '461 application.

In yet other embodiments, the cap assemblies, containers and methods described herein need not be used to determine the presence of cells or biologic activity. For example, in some embodiments, the container assemblies and systems described herein can be used in a titration assay to determine, for example, the pH of a sample. In such embodiments, a sample of unknown pH is added to a reaction chamber (e.g., the reaction chamber 4732) containing a dried pH indicator dye such as bromothymol blue. A housing or "cap assembly" (e.g., the housing 4741) is attached to the reaction chamber. As described above, the housing contains two reagent volumes (e.g., the volumes 4742 and 4744) and/or two reagent containers (e.g., the reagent containers 4780 and 4790). One of the reagent volumes and/or containers contains a known concentration of hydrochloric acid, and the other reagent volume and/or container contains a known concentration of sodium hydroxide.

In use, after adding the sample, the color of the solution in the reaction chamber can be determined (e.g., using any suitable instrument, such as the instruments described in the '461 application, which can contain a photodetector capable of determining the sample color). If the sample pH is neutral (6<pH<7.6), then the solution within the chamber (i.e., the solution of the sample and the dried reagent within the chamber) is green. If, however, the sample pH is >7.6 then the solution is blue. When the instrument detects the sample color as blue, the reagent in the first reagent volume (i.e., the known concentration of hydrochloric acid) can be added to the reaction chamber. The addition of the first reagent can be performed at any suitable rate and/or in any suitable amount. For example, in some embodiments, a predetermined amount of the first reagent (HCl) can be added. If the reaction turns from blue to yellow, then the sample contains at least an amount of hydroxyl ions that is equivalent to the concentration of hydrochloric acid in the first reagent volume. Thus, when the instrument detects a change in the color (e.g. from blue to yellow), an output indicating the pH and/or ion concentration can be produced.

If the pH is <6 then the reaction is yellow and the reagent in the second reagent volume (i.e., the known concentration of sodium hydroxide) can be added to the reaction chamber. If the reaction turns from yellow to blue, then the sample may contain at least an amount of hydrogen ions that is equivalent to the concentration of sodium hydroxide in the second reagent volume. Thus, when the instrument detects a change in the color (e.g. from yellow to blue), an output indicating the pH and/or ion concentration can be produced.

In yet other embodiments, any of the reagent volumes or reagent containers described herein can contain any suitable reagent to facilitate the use therein for any suitable assay. For example in some embodiments, a reagent volume or reagent container can include a variety of different dyes or indicators. Such dyes can include, for example, membrane dyes, lipophilic stains (e.g., "Nile red" or 9-diethylamino-5-benzo[α]phenoxazinone), a lipophilic cationic indocarbocyanine dye (e.g., "DiI" or (2Z)-2-[(E)-3-(3,3-dimethyl-1-octadecylindol-1-ium-2-yl)prop-2-enylidene]-3,3-dimethyl-1-octadecylindole; perchlorate) and/or a cell-permeant dye that can be used to determine cell viability (e.g., Calcein AM, produced by Life Technologies).

Although various embodiments have been described as having particular features and/or combinations of components, other embodiments are possible having a combination of any features and/or components from any of embodiments as discussed above. For example, in some embodiments, the actuator 4750 and/or the actuator 4760 of the cap assembly described above can include a concave engagement feature, such as the engagement portion 3754 described above with respect to the actuator 3750.

Analysis of the Collection Tool

The method 200 described above includes transferring the contents (e.g., transport media) disposed within the interior region of a transport container (e.g., the transport chamber 4014) to a reaction chamber (e.g., the reaction chamber 4732). Transferring the transport media includes transferring the patient sample (e.g., collected using a collection tool, such as a swab) from the transport chamber to the reaction chamber. In some embodiments, transferring the contents can include communicating the target bacteria released from the collection tool into the transport media, via a transfer tool (e.g., a pipette), to the reaction chamber. Thus, in some embodiments, methods can employ a collection tool that is effective for both (1) collecting a sample (e.g., from a nasal cavity of a patient) and (2) releasing the collected sample into the transport chamber, container assembly and/or reaction chamber. In particular, methods can employ a collection tool that is suitable for such methods in which the sample can include very low levels of the target bacteria (i.e., "low loads") and/or that employ limited incubation time. In this manner, method of detecting target cells can be effective even when the amount of target cells available for detection is limited.

For example, collection tools having a collection portion constructed from a wound material, such as wound Rayon or Dacron, may provide for patient comfort and/or efficient collection of the sample, but may not release a sufficient amount of the collected sample into the transport medium and/or transport chamber to be effective in the methods described herein. See, e.g., "Comparison of Rayon and Dacron Swabs in Amies Medium for *Bordetella pertussis* Transport," J. Stephen Thompson et al., ASM 99$^{th}$ General Meeting, May 1999; "Why Flocked Swabs are Superior to Fiber Wrapped Swabs and Foam Swabs and How They Can Improve Infectious Disease Diagnosis," Copan Innovation, Brescia, Italy, retrieved online at [http://www.mls.be/nieuwsbrieven/css/Why-Flocked-Swabs-are-Superior-to-Fiber-and-Foam.pdf] ("Copan Innovation"). Moreover, collection tools having a collection portion constructed from a foam material are consider has having poor absorption properties, and are thus often not used in bacterial assays. See Copan Innovation. Accordingly, tests were conducted to evaluate the collection tool (and more specifically the construction of the collection portion or "swab") to determine an appropriate collection tool for the assays and methods described herein.

Figure 28:
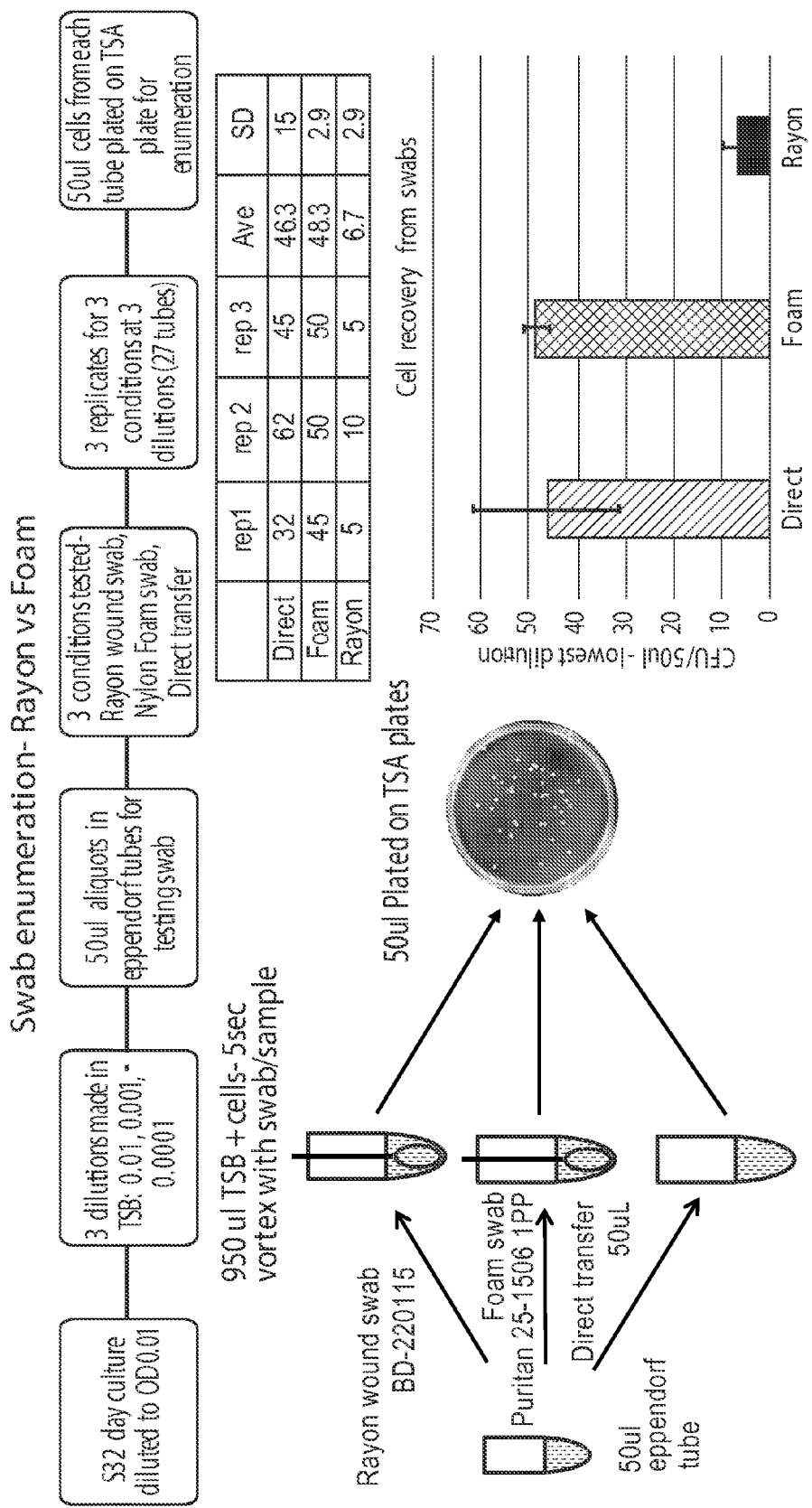
FIG. 28 is a schematic illustration of a test procedure, and the test results of a comparison of Rayon wound swabs vs. Nylon foam swabs.

A first test involved a comparison of cell recovery during transfer of cells using Rayon wound swabs (Becton Dickinson swab BD-220115), Nylon foam swabs (Puritan swab 25-1506 1PF) and a direct transfer of cells. A schematic illustration of the test procedure and the test results are shown in FIG. 28. As shown, the amount of cells released into the solution using foam swabs is approximately seven times greater than the amount of cells released using the wound swabs. In fact, the release or transfer efficiency of the foam swabs was comparable to that from a direct transfer of cells (e.g., via pipetting) into the solution. Accordingly, although wound swabs may provide for better liquid absorption (e.g., for use in collecting a sample), the release or transfer performance of wound swabs was inferior to that of foam swabs.

Figure 29:
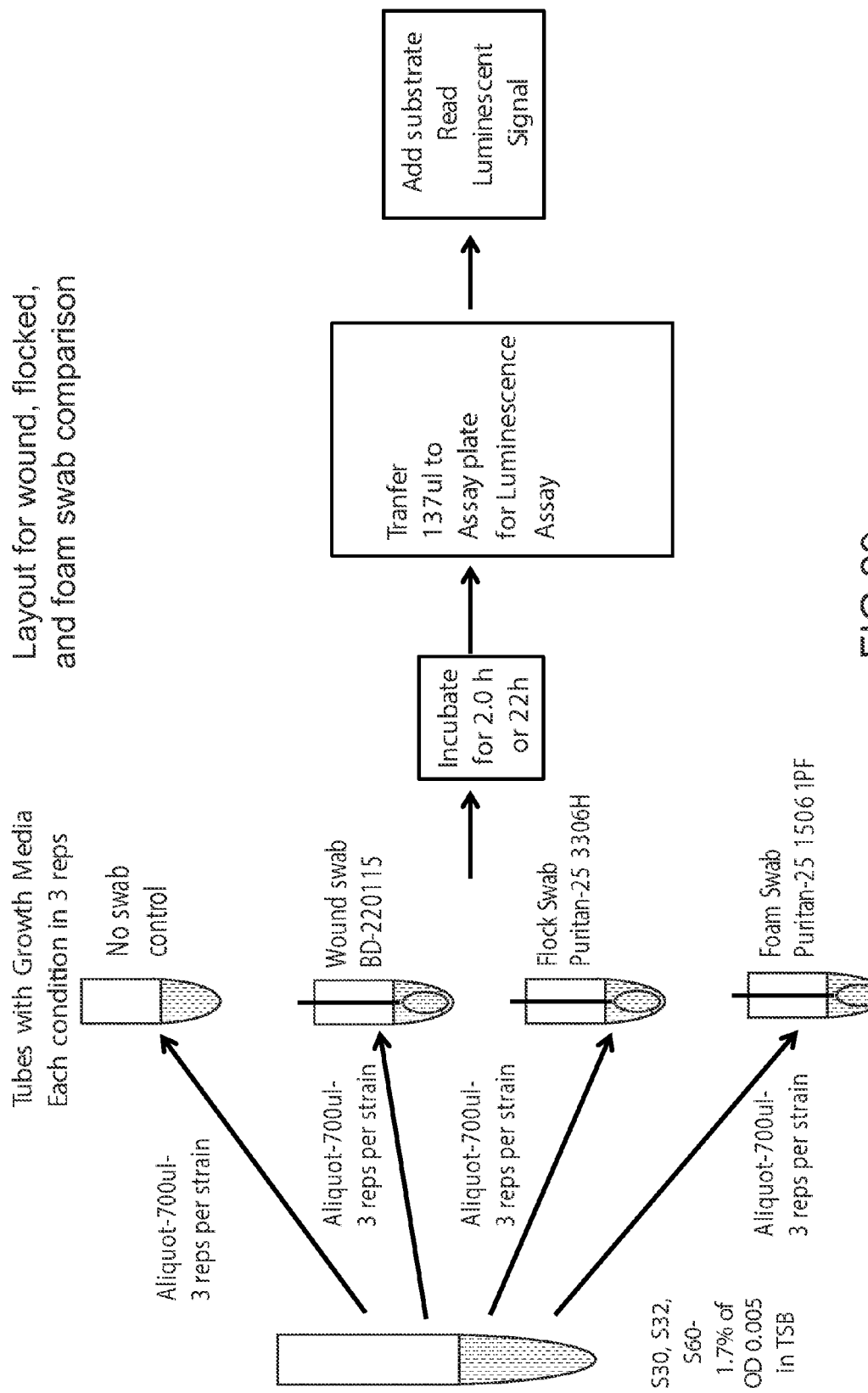
FIG. 29 is a schematic illustration of a test procedure comparing wound swabs, flock swabs and foam.

A second test involved comparing the signal output (i.e., Relative Light Units, or RLU) associated with a solution containing target cells transferred via a wound swab, a "flocked" swab and a foam swab. In this manner, by comparing the signal output, the second test was closely associated with the methods of detection described herein. As shown in FIG. 29, the second test included placing a swab into a known sample containing an amount of target cells. Each swab was then placed into a container containing amount of a transport media. In this manner, the container functions in a manner similar to any of the transport chambers described herein. In addition to the three different swabs, the test also included a "control" test, in which a portion of the sample was directly transferred into the container.

Each container was maintained in controlled conditions for a predetermined time or "incubation" period. The test included an incubation period of two hours and an incubation period of 20 hours. After completion of the incubation period, a controlled amount of the transport media was transferred to an assay plate for a manual assay. A reagent (i.e., a substrate) was added to the assay plate to react with the plurality of reporter molecules to enhance the luminescence signal. The luminescence signal was then recorded.

Figure 30A:
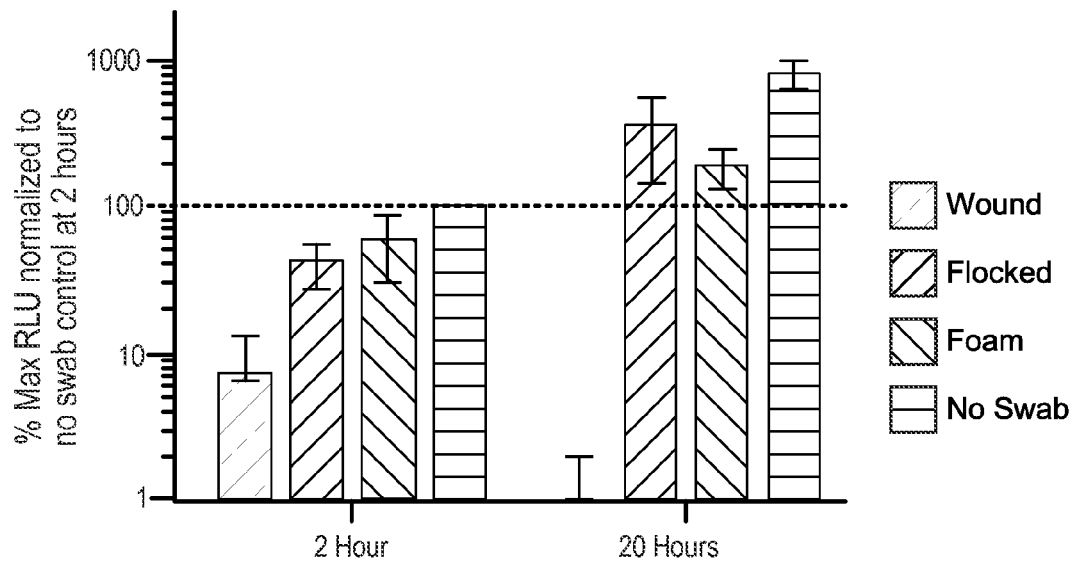
FIGS. 30A and 30B are bar charts showing the results from the test identified in FIG. 29.
Figure 30B:
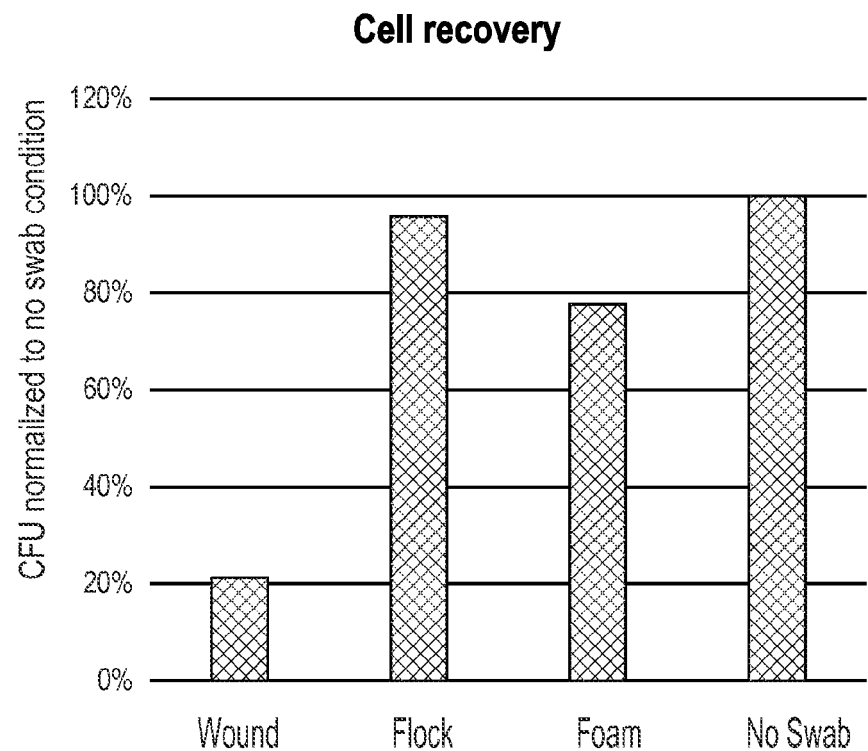

FIGS. 30A and 30B are graphs of the amount of light output (for both the two and 20 hour incubation times) and the amount of target cell recovery (in a percentage "colony forming units" resulting from the second test. FIG. 31A is a table showing the light output results for each individual test run (identified as tests S30, S32 and S60), and FIG. 31B is a graph of the data shown in the table in FIG. 31A. As the results of the second test show, for the two hour incubation time, the foam swab resulted in the production of more light output than did either the wound or flocked swab. Thus, although some assays are performed with wound swabs (for possible improved sample collection characteristics) or flocked swabs (for possible improved performance in sample collection and/or cell transfer), the surprising result is that the use of a collection tool having a collection portion constructed from a foam material can produce a greater signal. This advantage is particularly important where methods involve low cell loading and/or low nominal light outputs, which is the case with many of the methods described herein.

Similarly stated, these results demonstrate that at low sample levels (e.g., after a short time period), the performance of the foam swab is superior to that of a flocked swab. As such, in some embodiments, the methods described herein can include a collection tool selected specifically for use with incubation times that produce a low signal. In such embodiments, for example, a foam swab can be selected for a short incubation time and/or when there is limited amount of sample when it is determined that a foam swab performs adequately and/or performs better than other swab types at such short incubation times.

Because the second test indicated that under certain conditions the use of either a foam swab or a flocked swab was superior to the use of a wound swab, additional tests were conducted assess the performance of flocked swabs in different transport media. In particular, a third test was run comparing the signal output (i.e., Relative Light Units, or RLU) associated with a solution containing target cells and a "flocked" swab using two different types of transport media. The first media was identified as BSS M64 and the second media was identified as TSB Mod. The constituents of the two media are identified below in Table 1. First, the assay was run on the solution in the absence of any swab, and each solution produced a sufficient amount of light. Second, the assay was run with flocked swabs having been disposed within the solution. In this instance, the solution using the TSB Mod media failed to produce sufficient light output to complete the assay. Finally, the flocked swabs were soaked with the each of the two transport media and were then used to transfer cells to a conditioned media. In this instance, the swabs that were soaked in the TSB Mod solution failed to produce sufficient light output to complete the assay. Thus, although flocked swabs were shown in the second series of tests to be comparable to the foam swabs, the third series of tests showed that flocked swabs when used with the TSB Mod transport media did not perform adequately.

TABLE 1

| Components per liter of TSB | grams | Total amount |
|---|---|---|
| BSS M64 | | |
| Enzymatic Digest of Casein | 17 | 1.70% |
| Enzymatic Digest of Soybean Meal | 3 | 0.30% |
| Glucose | 2.5 | 0.30% |
| Dipotassium Phosphate | 2.5 | 0.30% |
| Sodium Chloride | 5 | 0.50% |
| TSB Mod | | |
| CaCl2 | 0.55 | 0.005M |
| MgCl2 | 0.952 | 0.01M |
| BGP | 12.96 | 0.06M |

Finally, a fourth series of tests was conducted assess the performance of flocked swabs and foam swabs when collecting a known sample via nasal sampling. The third test was run comparing the signal output (i.e., Relative Light Units, or RLU) associated with target cells collected from nasal samples. As indicated in Table 2 below, the use of a flocked swab recovered on average about 50,000 more CFU/ml of cells than did the use of a foam swab.

TABLE 2

| Sample # | Foam | Flocked | Flocked – Foam |
|---|---|---|---|
| 1 | 24,000 | 180,000 | 156,000 |
| 5 | 400 | 6,400 | 6,000 |
| 6 | 800 | 600 | (200) |
| 7 | 10,000 | 140,000 | 130,000 |
| 8 | 10,000 | 220,000 | 210,000 |
| 9 | 2,600 | 5,800 | 3,200 |
| 10 | 800 | 600 | (200) |
| 11 | 800 | 200 | (600) |
| 12 | 34,000 | 32,000 | (2,000) |
| 13 | 400 | 400 | — |
| | | Average | 50,220 |

Analysis of the Rate of Delivery of the Substrate

The methods described above include mixing a substrate with a sample at a predetermined rate. More particularly, in some embodiments, a bacterial luciferase reporter transduction particle can be employed. These reporters cause the expression of a bacterial luciferase such as that from the organism *V. fischeri*. Bacterial luciferase is comprised of the luxA and luxB genes encoding LuxA and LuxB proteins that combine to form the active luciferase enzyme. LuxAB catalyzes a luminescent reaction in the presence of oxygen, reduced flavin mononucleotide (FMNH2, supplied by the host cell), and an aldehyde such as tridecanal (supplied exogenously and which readily penetrates into viable bacterial cells).

Accordingly, during such methods or assays, bacterial luciferase is expressed and the luciferase molecules complex FMNH2 molecules. These complexes accumulate and when an aldehyde is added, the luminescence reaction proceeds. Ideally, it is preferable that all complexed luciferases are triggered to emit photons simultaneously. In this manner, a large flux of photons is emitted in a short period of time—i.e., a flash of light is produced that can be readily detected, especially when there is a low load of target cells. It is understood that if the complexed luciferases emit light in an un-synchronized manner, the photons are emitted over an extended period of time thereby not producing a flash.

Because the light emission kinetics is mediated by the availability of aldehyde (i.e., the substrate), under ideal conditions it is desirable to deliver the aldehyde instantaneously to an entire volume of a reaction. Injecting aldehyde into the reaction at a rapid speed can approach this ideal situation. Therefore, it can be reasoned that faster injection speeds will result in more optimal flash reactions. Indeed, a study that examined the effect of injection speed on light output found that increasing injection speed resulted in greater light output when measuring the peak value of light production. However, at a certain point, an increase in injection speed was found to result in lower light output and/or greater variability in the results. This phenomenon is attributed to splashing and bubble formation in the reaction that serves to perturb the detection of the light produced. Therefore, a desired range of injection speed (expressed as the speed of the actuator) was found where maximal light output is attained.

Figure 31:
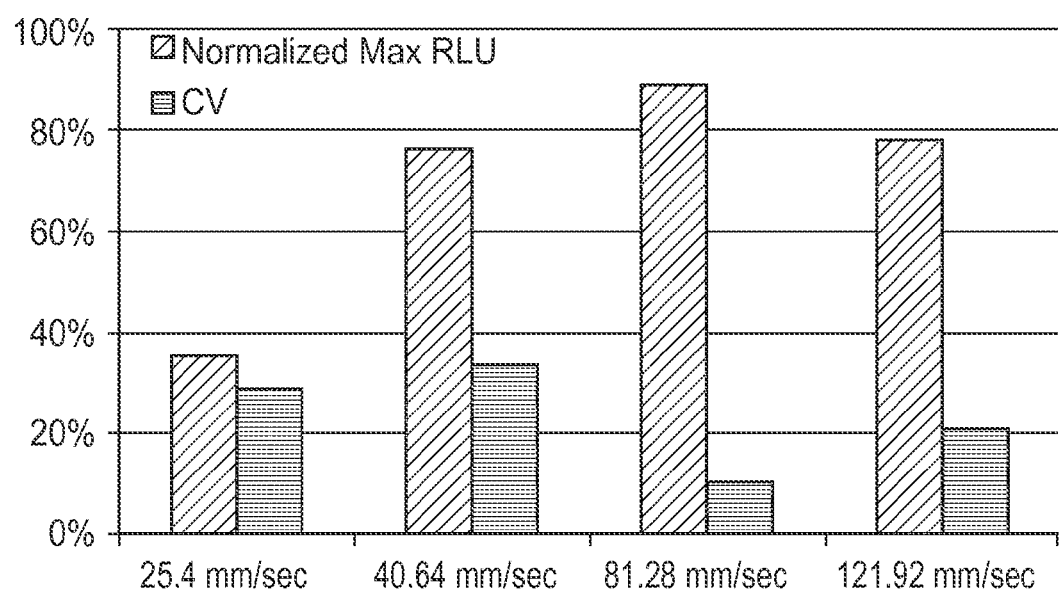
FIG. 31 is a bar graph of the results from a test comparing various different injection speeds of a substrate.

The test results are summarized in FIG. 31, which is a bar chart showing the average maximum RLU obtained from luciferase expressing cells after injecting aldehyde at varying speeds (the speeds are presented in steps per second, where one step is 0.0254 mm). Note that the RLU values are expressed as a percentage or the maximum RLU value obtained in this study. As shown, an optimum RLU output was observed at 3,200 steps/sec where the RLU values were maximum and the variability in light output (expressed as a coefficient of variation) was at a minimum. Further testing identified an optimal range of between about 2,500 steps/sec (63.5 mm/sec) and about 3,200 steps/sec (81.3 mm/sec). Thus, in some embodiments, the substrate is mixed by moving the actuator linearly at a rate of about 2,850 steps/sec (72.4 mm/sec).

What is claimed is:

1. An apparatus, comprising:
    a housing configured to be removably coupled to a reaction chamber, the housing defining a reagent volume configured to receive a reagent container, the housing including a puncturer defining a transfer pathway in fluid communication with the reagent volume, the puncturer and the housing being monolithically constructed, the housing including a delivery portion defining a delivery pathway between the transfer pathway and the reaction chamber when the housing is coupled to the reaction chamber; and
    an actuator having a plunger portion disposed within the reagent volume, an engagement portion of the actuator configured to be manipulated to move the plunger portion within the reagent volume to deform the reagent container, the puncturer configured to pierce a frangible portion of the reagent container to convey a reagent from the reagent container into the reaction chamber via the transfer pathway and the delivery pathway.

2. The apparatus of claim 1, wherein the transfer pathway is perpendicular to the frangible portion of the reagent container.

3. The apparatus of claim 1, wherein the puncturer defines a plurality of transfer pathways in fluid communication with the reagent volume and the delivery pathway, the transfer pathway being one of the plurality of transfer pathways.

4. The apparatus of claim 1, wherein a portion of the delivery pathway partially surrounds the puncturer.

5. The apparatus of claim 1, wherein an exit portion of the delivery pathway defines an exit axis that intersects a sidewall of the reaction chamber.

6. The apparatus of claim 1, further comprising:
    the reagent container disposed within the reagent volume, the reagent container including a skirt surrounding the frangible portion, the skirt and a surface of the delivery portion forming a substantially fluid-tight seal; and
    a lock member disposed within the reagent volume, the lock member configured to limit movement of the skirt relative to the housing when the reagent container is deformed to maintain the substantially fluid-tight seal between the skirt and the surface.

7. The apparatus of claim 1, further comprising:
    the reagent container disposed within the reagent volume, the reagent container including a skirt surrounding the frangible portion, a first portion of the skirt and a first surface of the delivery portion forming a substantially fluid-tight seal, a second portion of the skirt configured to engage a retention portion of the housing to limit movement of the skirt relative to the housing when the reagent container is deformed, the retention portion within the reagent volume.

8. The apparatus of claim 1, wherein the plunger portion of the actuator and a portion of the housing collectively define a seal to fluidically isolate the reagent volume from a volume outside of the housing.

9. The apparatus of claim 1, further comprising:
    the reagent container disposed within the reagent volume, the reagent container containing a plurality of transduction particles.

10. The apparatus of claim 9, wherein the plurality of transduction particles is engineered to be incapable of lytic replication.

11. The apparatus of claim 1, further comprising:
    the reagent container disposed within the reagent volume, the reagent container containing the reagent formulated to react with a plurality of reporter molecules in a sample to enhance production of a signal.

12. The apparatus of claim 1, further comprising:
    the reagent container disposed within the reagent volume, the reagent container containing at least one of a nutrient, an antibiotic, a lysis reagent or a sterilizing reagent.

13. The apparatus of claim 1, further comprising:
    the reagent container disposed within the reagent volume, the reagent container containing tridecanal.

14. The apparatus of claim 1, wherein the reagent is a first reagent, the apparatus further comprising:
    the reaction chamber containing a second reagent formulated to react with a sample within the reaction chamber.

15. An apparatus, comprising:
    a housing configured to be coupled to a reaction chamber, the housing defining a reagent volume configured to receive a reagent container, the housing including a puncturer having a sharp point configured to pierce a frangible portion of the reagent container, the puncturer defining a plurality of transfer pathways spaced circumferentially about the sharp point, each transfer pathway from the plurality of transfer pathways in fluid communication with an inner volume of the reaction chamber when the housing is coupled to the reaction chamber; and an actuator having a plunger portion disposed within the reagent volume, an engagement portion of the actuator configured to be manipulated to move the plunger portion within the reagent volume such that the sharp point pierces the frangible portion of the reagent container to convey a reagent from the reagent container into the reaction chamber via the plurality of transfer pathways.

16. The apparatus of claim 15, wherein the puncturer and the housing are monolithically constructed.

17. The apparatus of claim 15, wherein the plurality of transfer pathways produces a discontinuous cross-sectional shape within the puncturer at a cross-sectional position below the sharp point.

18. The apparatus of claim 15, wherein each transfer pathway from the plurality of transfer pathways is separate from the other transfer pathways from the plurality of transfer pathways.

19. The apparatus of claim 15, wherein each transfer pathway from the plurality of transfer pathways is spaced an equidistance from the sharp point.

20. The apparatus of claim 19, wherein the plurality of transfer pathways includes at least four separate transfer pathways.

21. The apparatus of claim 15, wherein the housing includes a delivery portion defining a delivery pathway that places the plurality of transfer pathways in fluid communication with the inner volume of the reaction chamber when the housing is coupled to the reaction chamber.

22. The apparatus of claim 21, wherein a portion of the delivery pathway partially surrounds the sharp point of the puncturer.

23. The apparatus of claim 21, wherein the reagent is a first reagent, the apparatus further comprising:
the reagent container disposed within the reagent volume, the reagent container containing the first reagent formulated to react with a plurality of reporter molecules in a sample to enhance production of a signal; and
the reaction chamber containing a second reagent formulated to react with the sample to limit production of the signal.

24. The apparatus of claim 23, wherein the second reagent contains an antibiotic in a solid form, the antibiotic formulated to limit production of the plurality of reporter molecules.

25. The apparatus of claim 21, further comprising:
the reagent container disposed within the reagent volume, the reagent container including a skirt surrounding the frangible portion, the skirt and a surface of the delivery portion forming a substantially fluid-tight seal; and
a lock member configured to limit movement of the skirt relative to the housing when the sharp point pierces the frangible portion of the reagent container to maintain the substantially fluid-tight seal between the skirt and the surface.

26. An apparatus, comprising:
a housing configured to be coupled to a reaction chamber, the housing defining a reagent volume configured to receive a reagent container, the housing including a puncturer configured to pierce a frangible portion of the reagent container, the puncturer defining a plurality of transfer pathways spaced apart along an outer surface of the puncturer, each transfer pathway from the plurality of transfer pathways in fluid communication with an inner volume of the reaction chamber when the housing is coupled to the reaction chamber; and
an actuator having a plunger portion disposed within the reagent volume, an engagement portion of the actuator configured to be manipulated to move the plunger portion within the reagent volume such that the puncturer pierces the frangible portion of the reagent container to convey a reagent from the reagent container into the reaction chamber via the plurality of transfer pathways.

27. The apparatus of claim 26, wherein each of the plurality of transfer pathways is perpendicular to the frangible portion of the reagent container.

28. The apparatus of claim 26, wherein the plurality of transfer pathways produces a discontinuous cross-sectional shape within the outer surface of the puncturer at a cross-sectional position below a sharp point of the puncturer.

29. The apparatus of claim 26, wherein each transfer pathway from the plurality of transfer pathways is separate from the other transfer pathways from the plurality of transfer pathways.

30. The apparatus of claim 26, wherein the plurality of transfer pathways includes at least four separate transfer pathways.

31. The apparatus of claim 26, wherein the housing includes a delivery portion defining a delivery pathway that places the plurality of transfer pathways in fluid communication with the inner volume of the reaction chamber when the housing is coupled to the reaction chamber.

32. The apparatus of claim 31, wherein a portion of the delivery pathway partially surrounds a sharp point of the puncturer.

33. The apparatus of claim 26, wherein the reagent is a first reagent, the apparatus further comprising:
the reagent container disposed within the reagent volume, the reagent container containing the first reagent formulated to react with a plurality of reporter molecules in a sample to enhance production of a signal; and
the reaction chamber containing a second reagent formulated to react with the sample to limit production of the signal.

34. The apparatus of claim 33, wherein the second reagent contains an antibiotic in a solid form, the antibiotic formulated to limit production of the plurality of reporter molecules.

35. The apparatus of claim 26, wherein the housing includes a threaded portion configured to be matingly coupled to a threaded portion of the reaction chamber.

36. The apparatus of claim 26, wherein the puncturer and the housing are monolithically constructed.

* * * * *